US012799103B2

(12) United States Patent
Lian et al.

(10) Patent No.: US 12,799,103 B2
(45) Date of Patent: Nov. 17, 2026

(54) ISOXAZOLINE OXIME FORMATE COMPOUND, PREPARATION METHOD THEREFOR, HERBICIDAL COMPOSITION AND USE THEREOF

(71) Applicant: QINGDAO KINGAGROOT CHEMICAL COMPOUND CO., LTD., Qingdao (CN)

(72) Inventors: Lei Lian, Qingdao (CN); Rongbao Hua, Qingdao (CN); Xuegang Peng, Qingdao (CN); De Zhao, Qingdao (CN); Qi Cui, Qingdao (CN)

(73) Assignee: QINGDAO KINGAGROOT CHEMICAL COMPOUND CO., LTD., Qingdao (CN)

( * ) Notice: Subject to any disclaimer, the term of this patent is extended or adjusted under 35 U.S.C. 154(b) by 1134 days.

(21) Appl. No.: 17/786,118

(22) PCT Filed: Dec. 17, 2020

(86) PCT No.: PCT/CN2020/137010

§ 371 (c)(1),
(2) Date: Jun. 16, 2022

(87) PCT Pub. No.: WO2021/139498

PCT Pub. Date: Jul. 15, 2021

(65) Prior Publication Data

US 2023/0072860 A1 Mar. 9, 2023

(30) Foreign Application Priority Data

Jan. 7, 2020 (CN) ......................... 202010014157.5

(51) Int. Cl.
*C07D 413/10* (2006.01)
*A01N 43/74* (2006.01)

(52) U.S. Cl.
CPC ........... *C07D 413/10* (2013.01); *A01N 43/74* (2013.01)

(58) Field of Classification Search
CPC .. C07D 413/10; C07D 413/04; C07D 413/14; A01N 43/74; A01N 43/80; A01P 13/00
See application file for complete search history.

(56) References Cited

U.S. PATENT DOCUMENTS 5,521,143 A * 5/1996 Loher .................... A01N 43/80 544/137
6,602,825 B1 8/2003 Menke et al.
2018/0230139 A1* 8/2018 Liu ...................... C07D 413/10

FOREIGN PATENT DOCUMENTS

CN 105753853 A 7/2016
CN 108570041 A 9/2018
CN 109864068 A 6/2019
CN 110150302 A 8/2019
CN 111961041 A * 11/2020 ........... C07D 413/10
WO WO 00/50409 A1 8/2000
WO WO 2016/095768 A1 6/2016

OTHER PUBLICATIONS

World Intellectual Property Organization, International Search Report and Written Opinion in counterpart International Patent Application No. PCT/CN2020/137010, mailed on Mar. 12, 2021.

(Continued)

*Primary Examiner* — Monica A Shin

(74) *Attorney, Agent, or Firm* — Leydig, Voit & Mayer, Ltd.

(57) ABSTRACT

The present invention belongs to the technical field of pesticides, and specifically relates to an isoxazoline oxime formate compound, a preparation method therefor, and a herbicidal composition and a use thereof. The isoxazoline oxime formate compound is shown in general formula I.

I

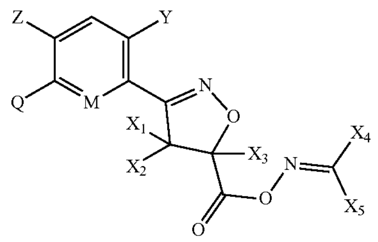

Wherein, Y represents halogen, haloalkyl, cyano, nitro or amino; Z represents hydrogen, halogen or hydroxyl; Q represents

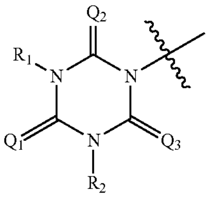

or

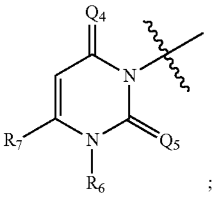

;

M represents CH or N; $X_1$, $X_2$ and $X_3$ each independently represent hydrogen, etc.; $X_4$ and $X_5$ each independently represent hydrogen, halogen, cyano or nitro, etc. The compound also has an excellent herbicidal activity against grassy weeds, broadleaf weeds, etc. at a low application rate, and has a high selectivity to crops.

15 Claims, No Drawings

(56) References Cited

OTHER PUBLICATIONS

Wang et al., "Discovery of Novel N-Isoxazolinylphenyltriazinones as Promising Protoporphyrinogen IX Oxidase Inhibitors", *Journal of Agricultural and Food Chemistry*, vol. 67, pp. 12382-12392 (2019).
Indian Patent Office; Office Action in corresponding Indian Application No. 202247037880, dated Jul. 1, 2026.
Santosh Kumar, S. C., et al., "A Convenient Practical Synthesis of Alkyl and Aryl Oxime Esters", SYNTHESIS 2014, 46, 1847-1852, Advanced online publication: 24.06.20140039-78811437-210X DOI: 10.1055/s-0034-1378350.

* cited by examiner

ISOXAZOLINE OXIME FORMATE COMPOUND, PREPARATION METHOD THEREFOR, HERBICIDAL COMPOSITION AND USE THEREOF

CROSS-REFERENCE TO RELATED APPLICATIONS

This patent application is the U.S. National Stage of International Patent Application No. PCT/CN2020/137010, filed Dec. 17, 2020, which claims the benefit of Chinese Patent Application No. 202010014157.5, filed Jan. 7, 2020, which are each incorporated by reference.

TECHNICAL FIELD

The present invention relates to the technical field of pesticides, and in particular a type of isoxazoline oxime formate compound, preparation method, herbicidal composition and use thereof.

TECHNICAL BACKGROUND

Weed control is one of the most important links in the course of achieving high-efficiency agriculture. Various herbicides are available in the market, for example, patents WO00/50409 etc. disclose the use of a compound of general formula 1-aryl-4-thiotriazine as a herbicide, and WO2016/095768A1 discloses an isoxazoline-containing uracil compound and the herbicidal use thereof. However, the herbicidal properties of these known compounds against harmful plants and their selectivities to crops are not completely satisfactory. And scientists still need to do continuously research and develop new herbicides with high efficacy, safety, economics and different modes of action due to problems such as the growing market, weed resistance, the service life and economics of pesticides as well as people's increasing concern on environment.

INVENTION CONTENTS

The present invention provides a type of isoxazoline oxime formate compound, preparation method, herbicidal composition and use thereof. The compound also has an excellent herbicidal activity against grassy weeds, broadleaf weeds, etc. at a low application rate, and has a high selectivity to crops.

The technical solution adopted by the invention is as follows:

An isoxazoline oxime formate compound, as shown in general formula I.

I

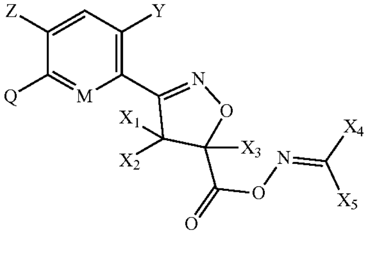

wherein,

Y represents halogen, halogenated alkyl, cyano, nitro or amino;

Z represents hydrogen, halogen or hydroxyl;

Q represents

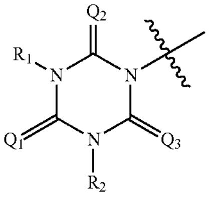

or

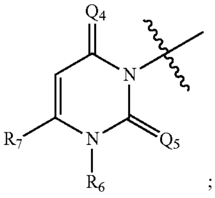

;

M represents CH or N;

$X_1$, $X_2$, $X_3$ each independently represent hydrogen, halogen, nitro, cyano, thiocyano, hydroxyl, sulfhydryl, carboxyl, sulfonic, formyl, halogenated formyl, azido, alkyl, alkenyl, alkynyl, cycloalkyl, cycloalkylalkyl, cycloalkenyl, cycloalkenylalkyl, $-PO(OR')_2$, $-(CO)O\text{-alkyl-}O-N=C(R')_2$, $-OR''$, $-(CO)R''$, $-SR''$, $-(SO)R''$, $-(SO_2)R''$, $-Si(R'')_3$, $-O(CO)R''$, $-O-(SO_2)R''$, $-S(CO)R''$, $-(SO_2)OR''$, $-(CO)OR''$, $-(CO)SR''$, $-(CS)OR''$, $-O(CO)OR''$, $-(CO)(CO)OR''$, $-(CO)O(CO)R''$, $-(CO)O(CO)OR''$, heterocyclyl, heterocyclylalkyl, aryl, arylalkyl, amino, aminoalkyl, aminocarbonyl, aminocarbonylalkyl, aminocarbonyloxyalkyl, aminothiocarbonyloxyalkyl, aminosulfonyl, or aminosulfonyloxyalkyl, or $X_1$ and $X_2$ together form $-CH_2CH_2CH_2-$, $-CH_2CH_2CH_2CH_2-$, $-CH_2CH_2CH_2CH_2CH_2-$, $-OCH_2CH_2-$, $-OCH_2O-$, $-OCH_2CH_2O-$, $-CH_2CH_2OCO-$ or $-CH=CH-CH=CH-$;

wherein, the "alkyl", "alkenyl" or "alkynyl" is each independently unsubstituted or substituted with at least one substituent selected from halogen, cyano, hydroxyl, sulfhydryl, carboxyl, $-OR''$, $-(CO)R''$, $-SR''$, $-(SO_2)R''$, $-O(CO)R''$, $-O-(SO_2)R''$, $-(CO)OR''$ or $-O(CO)OR''$;

the "amino", "aminoalkyl", "aminocarbonyl", "aminocarbonylalkyl", "aminocarbonyloxyalkyl", "aminothiocarbonyloxyalkyl", "aminosulfonyl" or "aminosulfonyloxyalkyl" is each independently unsubstituted or substituted with one or two substituents selected from $-R_{11}$, $-OR_{11}$, $-(CO)R_{11}$, $-(CO)OR_{11}$, $-O(CO)R_{11}$, $\text{-alkyl-}(CO)OR_{11}$, $-(SO_2)R_{11}$, $-(SO_2)OR_{11}$, $\text{-alkyl-}(SO_2)R_{11}$, $-(CO)N(R_{12})_2$ or $-(SO_2)N(R_{12})_2$;

the "cycloalkyl", "cycloalkylalkyl", "cycloalkenyl", "cycloalkenylalkyl", "heterocyclyl", "heterocyclylalkyl", "aryl" or "arylalkyl" is each independently unsubstituted or substituted with at least one substituent selected from oxo, halogen, cyano, nitro, alkyl, halogenated alkyl, benzyl, $-OR_{14}$, $-SR_{14}$, $-(CO)OR_{14}$, $-(SO_2)R_{14}$, $-N(R_{14})_2$ or $-O\text{-alkyl-}(CO)OR_{14}$;

the "$-CH_2CH_2CH_2-$", "$-CH_2CH_2CH_2CH_2-$", "$-CH_2CH_2CH_2CH_2CH_2-$", "$-CH_2OCH_2-$", "$-CH_2CH_2OCH_2CH_2-$", "$-OCH_2CH_2-$", "$-OCH_2O-$", "$-OCH_2CH_2O-$", "$-CH_2CH_2CO-$", "$-CH_2OCO-$", "$-CH_2OSO_2-$", "$-CH_2CH_2OCO-$", "$-CH=CHCOO-$", "$-CH=CH-CH=CH-$" or "$-CH_2CH_2OCO-$" is each independently unsubstituted or substituted with halogen;

$X_4$, $X_5$ each independently represent hydrogen, halogen, cyano, nitro, $\text{-(alkyl)}_n\text{-}OR_{15}$, $\text{-(alkyl)}_n\text{-}SR_{15}$, $\text{-(alkyl)}_n\text{-}(CO)R_{15}$, $\text{-(alkyl)}_n\text{-}O(CO)R_{15}$, $\text{-(alkyl)}_n\text{-}(CO)OR_{15}$, $\text{-(alkyl)}_n\text{-}(CO)SR_{15}$, aminocarbonyl, alkyl, alkenyl, alkynyl, cycloalkyl, cycloalkylalkyl, cycloalkenyl, cycloalkenylalkyl, aryl, arylalkyl, heterocyclyl or heterocyclylalkyl, or the $CX_4X_5$ group together forms ring structure; wherein, the "aminocarbonyl" is unsubstituted or substituted with one or two substituents selected from —$R_{11}$, —$OR_{11}$, —(CO)$R_{11}$, —(CO)$OR_{11}$, —O(CO)$R_{11}$, -alkyl-(CO)$OR_{11}$, —($SO_2$)$R_{11}$, —($SO_2$)$OR_{11}$, -alkyl-($SO_2$)$R_{11}$, —(CO)N($R_{12}$)$_2$ or —($SO_2$)N($R_{12}$)$_2$; the "alkyl", "alkenyl" or "alkynyl" is each independently unsubstituted or substituted with halogen; the "cycloalkyl", "cycloalkylalkyl", "cycloalkenyl", "cycloalkenylalkyl", "aryl", "arylalkyl", "heterocyclyl" or "heterocyclylalkyl" is each independently unsubstituted or substituted with at least one substituent selected from oxo, halogen, cyano, nitro, alkyl, halogenated alkyl, benzyl, —$OR_{14}$, —$SR_{14}$, —(CO)$OR_{14}$, —($SO_2$)$R_{14}$, —N($R_{14}$)$_2$ or —O-alkyl-(CO)$OR_{14}$, or two adjacent carbon atoms on the ring together with —$OCH_2CH_2$— or —$OCH_2O$— form a fused ring;

$Q_1$, $Q_2$, $Q_3$, $Q_4$, $Q_5$ each independently represent oxygen or sulphur;

$R_1$, $R_2$ each independently represent hydrogen, cyano, alkyl, alkenyl, alkynyl, formylalkyl, cyanoalkyl, amino, aminoalkyl, aminocarbonyl, aminocarbonylalkyl, aminosulfonyl, cycloalkyl, cycloalkylalkyl, cycloalkenyl, cycloalkenylalkyl, heterocyclyl, heterocyclylalkyl, aryl, arylalkyl, $R_4R_5$N—(CO)—$NR_3$—,

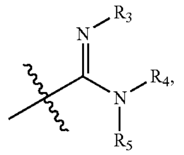

$R_3$—S(O)$_m$-(alkyl)$_n$-, $R_3$—O-(alkyl)$_n$-, $R_3$—(CO)-(alkyl)$_n$-, $R_3$—O-(alkyl)$_n$-(CO)—, $R_3$—(CO)—O-(alkyl)$_n$-, $R_3$—S—(CO)-(alkyl)$_n$-, $R_3$—O—(CO)-alkyl- or $R_3$—O—(CO)—O-alkyl-; wherein, the "alkyl", "alkenyl" or "alkynyl" is each independently unsubstituted or substituted with halogen;

the "amino", "aminoalkyl", "aminocarbonyl", "aminocarbonylalkyl" or "aminosulfonyl" is each independently unsubstituted or substituted with one or two substituents selected from —$R_{11}$, —$OR_{11}$, —(CO)$R_{11}$, —(CO)$OR_{11}$, —O(CO)$R_{11}$, -alkyl-(CO)$OR_{11}$, —($SO_2$)$R_{11}$, —($SO_2$)$OR_{11}$, -alkyl-($SO_2$)$R_{11}$, —(CO)N($R_{12}$)$_2$ or —($SO_2$)N($R_{12}$)$_2$;

the "cycloalkyl", "cycloalkylalkyl", "cycloalkenyl", "cycloalkenylalkyl", "heterocyclyl", "heterocyclylalkyl", "aryl" or "arylalkyl" is each independently unsubstituted or substituted with at least one substituent selected from oxo, halogen, cyano, nitro, alkyl, halogenated alkyl, benzyl, —$OR_{14}$, —$SR_{14}$, —(CO)$OR_{14}$, —($SO_2$)$R_{14}$, —N($R_{14}$)$_2$ or —O-alkyl-(CO)$OR_{14}$;

$R_6$, $R_7$ each independently represent hydrogen, alkyl or halogenated alkyl;

R' each independently represents hydrogen, halogen, alkoxy, alkoxyalkyl, alkyl, alkenyl, alkynyl, cycloalkyl, cycloalkylalkyl, cycloalkenyl, cycloalkenylalkyl, aryl, arylalkyl, heterocyclyl or heterocyclylalkyl, or the C(R')$_2$ group in —(CO)O-alkyl-O—N═C(R')$_2$ together forms ring structure; wherein, the "alkyl", "alkenyl" or "alkynyl" is each independently unsubstituted or substituted with halogen; the "cycloalkyl", "cycloalkylalkyl", "cycloalkenyl", "cycloalkenylalkyl", "aryl", "arylalkyl", "heterocyclyl" or "heterocyclylalkyl" is each independently unsubstituted or substituted with at least one substituent selected from oxo, halogen, cyano, nitro, alkyl, halogenated alkyl, benzyl, —$OR_{14}$, —$SR_{14}$, —(CO)$OR_{14}$, —($SO_2$)$R_{14}$, —N($R_{14}$)$_2$ or —O-alkyl-(CO)$OR_{14}$;

R" each independently represents alkyl, alkenyl, alkynyl, cycloalkyl, cycloalkylalkyl, cycloalkenyl, cycloalkenylalkyl, aryl, arylalkyl, arylalkenyl, heterocyclyl, heterocyclylalkyl or heterocyclylalkenyl; wherein, the "alkyl", "alkenyl" or "alkynyl" is each independently unsubstituted or substituted with at least one substituent selected from halogen, cyano, trialkylsilyl, —$OR_{13}$, —$SR_{13}$, —O(CO)$R_{13}$, —(CO)$R_{13}$, —(CO)$OR_{13}$ or —O(CO)$OR_{13}$; the "cycloalkyl", "cycloalkylalkyl", "cycloalkenyl", "cycloalkenylalkyl", "aryl", "arylalkyl", "arylalkenyl", "heterocyclyl", "heterocyclylalkyl" or "heterocyclylalkenyl" is each independently unsubstituted or substituted with at least one substituent selected from oxo, halogen, cyano, nitro, alkyl, halogenated alkyl, benzyl, —$OR_{14}$, —$SR_{14}$, —(CO)$OR_{14}$, —($SO_2$)$R_{14}$, —N($R_{14}$)$_2$ or —O-alkyl-(CO)$OR_{14}$;

$R_3$, $R_4$, $R_5$, $R_{15}$ each independently represent hydrogen, alkyl, alkenyl, alkynyl, cycloalkyl, cycloalkylalkyl, cycloalkenyl, cycloalkenylalkyl, heterocyclyl, heterocyclylalkyl, aryl or arylalkyl; wherein, the "alkyl", "alkenyl" or "alkynyl" is each independently unsubstituted or substituted with halogen; the "cycloalkyl", "cycloalkylalkyl", "cycloalkenyl", "cycloalkenylalkyl", "heterocyclyl", "heterocyclylalkyl", "aryl" or "arylalkyl" is each independently unsubstituted or substituted with at least one substituent selected from oxo, halogen, cyano, nitro, alkyl, halogenated alkyl, benzyl, —$OR_{14}$, —$SR_{14}$, —(CO)$OR_{14}$, —($SO_2$)$R_{14}$, —N($R_{14}$)$_2$ or —O-alkyl-(CO)$OR_{14}$;

$R_{11}$ each independently represents alkyl, alkenyl, alkynyl, cycloalkyl, cycloalkylalkyl, cycloalkenyl, cycloalkenylalkyl, phenyl or benzyl; wherein, the "alkyl", "alkenyl" or "alkynyl" is each independently unsubstituted or substituted with halogen; the "phenyl" or "benzyl" is each independently unsubstituted or substituted with at least one substituent selected from halogen, cyano, nitro, alkyl, halogenated alkyl, alkoxycarbonyl, alkylthio, alkylsulfonyl, alkoxy or halogenated alkoxy;

$R_{12}$ each independently represents hydrogen, alkyl, alkenyl, alkynyl, alkoxy, alkylsulfonyl, cycloalkyl, cycloalkylalkyl, cycloalkenyl or cycloalkenylalkyl; or the N($R_{12}$)$_2$ group in —(CO)N($R_{12}$)$_2$ or —($SO_2$)N($R_{12}$)$_2$ each independently represents heterocyclyl with nitrogen atom at 1-position;

$R_{13}$ each independently represents alkyl, alkenyl, alkynyl, cycloalkyl, phenyl or phenyl substituted with at least one substituent selected from halogen, cyano, nitro, alkyl, halogenated alkyl, alkoxy, halogenated alkoxy, alkoxycarbonyl, alkylthio, alkylsulfonyl or phenoxyl substituted with at least one substituent selected from halogen, cyano, nitro, alkyl, halogenated alkyl, alkoxy or halogenated alkoxy;

$R_{14}$ each independently represents hydrogen, alkyl, halogenated alkyl, phenyl or phenyl substituted with at least one substituent selected from halogen, cyano, nitro, alkyl, halogenated alkyl, alkoxycarbonyl, alkylthio, alkylsulfonyl, alkoxy or halogenated alkoxy;

m represents 0, 1 or 2; n independently represents 0 or 1.

Preferably, Y represents halogen, halogenated C1-C8 alkyl, cyano, nitro or amino;

More preferably, Y represents halogen, halogenated C1-C6 alkyl, cyano, nitro or amino;

Preferably, $X_1$, $X_2$, $X_3$ each independently represent hydrogen, halogen, nitro, cyano, thiocyano, hydroxyl, sulfhydryl, carboxyl, sulfonic, formyl, halogenated formyl, azido, C1-C8 alkyl, C2-C8 alkenyl, C2-C8 alkynyl, C3-C8 cycloalkyl, C3-C8 cycloalkyl C1-C8 alkyl, C3-C8 cycloalkenyl, C3-C8 cycloalkenyl C1-C8 alkyl, —PO(OR')$_2$, —(CO)O—(C1-C8 alkyl)-O—N═C(R')$_2$, —OR", —(CO)R", —SR", —(SO)R", —($SO_2$)R", —Si(R")$_3$, —O(CO)R", —O—($SO_2$)R", —S(CO)R", —($SO_2$)OR", —(CO)OR", —(CO)SR", —(CS)OR", —O(CO)OR", —(CO)(CO)OR", —(CO)O(CO)R", —(CO)O(CO)OR", heterocyclyl, heterocyclyl C1-C8 alkyl, aryl, aryl C1-C8 alkyl, amino, amino C1-C8 alkyl, aminocarbonyl, aminocarbonyl C1-C8 alkyl, aminocarbonyloxy C1-C8 alkyl, aminothiocarbonyloxy C1-C8 alkyl, aminosulfonyl, or aminosulfonyloxy C1-C8 alkyl, or $X_1$ and $X_2$ together form —$CH_2CH_2CH_2$—, —$CH_2CH_2CH_2CH_2$—, —$CH_2CH_2CH_2CH_2CH_2$—, —$OCH_2CH_2$—, —$OCH_2O$—, —$OCH_2CH_2O$—, —$CH_2CH_2OCO$— or —CH═CH—CH═CH—; wherein,

- the "C1-C8 alkyl", "C2-C8 alkenyl" or "C2-C8 alkynyl" is each independently unsubstituted or substituted with one to four substituents selected from halogen, cyano, hydroxyl, sulfhydryl, carboxyl, —OR", —(CO)R", —SR", —($SO_2$)R", —O(CO)R", —O—($SO_2$)R", —(CO)OR" or —O(CO)OR";
- the "amino", "amino C1-C8 alkyl", "aminocarbonyl", "aminocarbonyl C1-C8 alkyl", "aminocarbonyloxy C1-C8 alkyl", "aminothiocarbonyloxy C1-C8 alkyl", "aminosulfonyl" or "aminosulfonyloxy C1-C8 alkyl" is each independently unsubstituted or substituted with one or two substituents selected from —$R_{11}$, —$OR_{11}$, —(CO)$R_{11}$, —(CO)$OR_{11}$, —O(CO)$R_{11}$, —(C1-C8 alkyl)-(CO)$OR_{11}$, —($SO_2$)$R_{11}$, —($SO_2$)$OR_{11}$, —(C1-C8 alkyl)-($SO_2$)$R_{11}$, —(CO)N($R_{12}$)$_2$ or —($SO_2$)N($R_{12}$)$_2$;
- the "C3-C8 cycloalkyl", "C3-C8 cycloalkyl C1-C8 alkyl", "C3-C8 cycloalkenyl", "C3-C8 cycloalkenyl C1-C8 alkyl", "heterocyclyl", "heterocyclyl C1-C8 alkyl", "aryl" or "aryl C1-C8 alkyl" is each independently unsubstituted or substituted with one to four substituents selected from oxo, halogen, cyano, nitro, C1-C8 alkyl, halogenated C1-C8 alkyl, benzyl, —$OR_{14}$, —$SR_{14}$, —(CO)$OR_{14}$, —($SO_2$)$R_{14}$, —N($R_{14}$)$_2$ or —O—(C1-C8 alkyl)-(CO)$OR_{14}$;
- the "—$CH_2CH_2CH_2$—", "—$CH_2CH_2CH_2CH_2$—", "—$CH_2CH_2CH_2CH_2CH_2$—", "—$CH_2OCH_2$—", "—$CH_2CH_2OCH_2CH_2$—", "—$OCH_2CH_2$—", "—$OCH_2O$—", "—$OCH_2CH_2O$—", "—$CH_2CH_2CO$—", "—$CH_2OCO$—", "—$CH_2OSO_2$—", "—$CH_2CH_2OCO$—", "—CH═CHCOO—", "—CH═CH—CH═CH—" or "—$CH_2CH_2OCO$—" is each independently unsubstituted or substituted with halogen;

More preferably, $X_1$, $X_2$, $X_3$ each independently represent hydrogen, halogen, nitro, cyano, thiocyano, hydroxyl, sulfhydryl, carboxyl, sulfonic, formyl, halogenated formyl, azido, C1-C6 alkyl, C2-C6 alkenyl, C2-C6 alkynyl, C3-C6 cycloalkyl, C3-C6 cycloalkyl C1-C6 alkyl, C3-C6 cycloalkenyl, C3-C6 cycloalkenyl C1-C6 alkyl, —PO(OR')$_2$, —(CO)O—(C1-C6 alkyl)-O—N═C(R')$_2$, —OR", —(CO)R", —SR", —(SO)R", —($SO_2$)R", —Si(R")$_3$, —O(CO)R", —O—($SO_2$)R", —S(CO)R", —($SO_2$)OR", —(CO)OR", —(CO)SR", —(CS)OR", —O(CO)OR", —(CO)(CO)OR", —(CO)O(CO)R", —(CO)O(CO)OR", heterocyclyl, heterocyclyl C1-C6 alkyl, aryl, aryl C1-C6 alkyl, amino, amino C1-C6 alkyl, aminocarbonyl, aminocarbonyl C1-C6 alkyl, aminocarbonyloxy C1-C6 alkyl, aminothiocarbonyloxy C1-C6 alkyl, aminosulfonyl, or aminosulfonyloxy C1-C6 alkyl, or $X_1$ and $X_2$ together form —$CH_2CH_2CH_2$—, —$CH_2CH_2CH_2CH_2$—, —$CH_2CH_2CH_2CH_2CH_2$—, —$OCH_2CH_2$—, —$OCH_2O$—, —$OCH_2CH_2O$—, —$CH_2CH_2OCO$— or —CH═CH—CH═CH—; wherein,

- the "C1-C6 alkyl", "C2-C6 alkenyl" or "C2-C6 alkynyl" is each independently unsubstituted or substituted with one, two or three substituents selected from halogen, cyano, hydroxyl, sulfhydryl, carboxyl, —OR", —(CO)R", —SR", —($SO_2$)R", —O(CO)R", —O—($SO_2$)R", —(CO)OR" or —O(CO)OR";
- the "amino", "amino C1-C6 alkyl", "aminocarbonyl", "aminocarbonyl C1-C6 alkyl", "aminocarbonyloxy C1-C6 alkyl", "aminothiocarbonyloxy C1-C6 alkyl", "aminosulfonyl" or "aminosulfonyloxy C1-C6 alkyl" is each independently unsubstituted or substituted with one or two substituents selected from —$R_{11}$, —$OR_{11}$, —(CO)$R_{11}$, —(CO)$OR_{11}$, —O(CO)$R_{11}$, —(C1-C6 alkyl)-(CO)$OR_{11}$, —($SO_2$)$R_{11}$, —($SO_2$)$OR_{11}$, —(C1-C6 alkyl)-($SO_2$)$R_{11}$, —(CO)N($R_{12}$)$_2$ or —($SO_2$)N($R_{12}$)$_2$;
- the "C3-C6 cycloalkyl", "C3-C6 cycloalkyl C1-C6 alkyl", "C3-C6 cycloalkenyl", "C3-C6 cycloalkenyl C1-C6 alkyl", "heterocyclyl", "heterocyclyl C1-C6 alkyl", "aryl" or "aryl C1-C6 alkyl" is each independently unsubstituted or substituted with one, two or three substituents selected from oxo, halogen, cyano, nitro, C1-C6 alkyl, halogenated C1-C6 alkyl, benzyl, —$OR_{14}$, —$SR_{14}$, —(CO)$OR_{14}$, —($SO_2$)$R_{14}$, —N($R_{14}$)$_2$ or —O—(C1-C6 alkyl)-(CO)$OR_{14}$;
- the "—$CH_2CH_2CH_2$—", "—$CH_2CH_2CH_2CH_2$—", "—$CH_2CH_2CH_2CH_2CH_2$—", "—$CH_2OCH_2$—", "—$CH_2CH_2OCH_2CH_2$—", "—$OCH_2CH_2$—", "—$OCH_2O$—", "—$OCH_2CH_2O$—", "—$CH_2CH_2CO$—", "—$CH_2OCO$—", "—$CH_2OSO_2$—", "—$CH_2CH_2OCO$—", "—CH═CHCOO—", "—CH═CH—CH═CH—" or "—$CH_2CH_2OCO$—" is each independently unsubstituted or substituted with halogen;

Preferably, $X_4$, $X_5$ each independently represent hydrogen, halogen, cyano, nitro, —(C1-C8 alkyl)$_n$-$OR_{15}$, —(C1-C8 alkyl)$_n$-$SR_{15}$, —(C1-C8 alkyl)$_n$-(CO)$R_{15}$, —(C1-C8 alkyl)$_n$-O(CO)$R_{15}$, —(C1-C8 alkyl)$_n$-(CO)$OR_{15}$, —(C1-C8 alkyl)$_n$-(CO)$SR_{15}$, aminocarbonyl, C1-C8 alkyl, C2-C8 alkenyl, C2-C8 alkynyl, C3-C8 cycloalkyl, C3-C8 cycloalkyl C1-C8 alkyl, C3-C8 cycloalkenyl, C3-C8 cycloalkenyl C1-C8 alkyl, aryl, aryl C1-C8 alkyl, heterocyclyl or heterocyclyl C1-C8 alkyl, or the $CX_4X_5$ group together forms 5- to 8-membered carbocyclyl or oxygen-, sulfur- or nitrogen-containing heterocyclyl; wherein, the "aminocarbonyl" is unsubstituted or substituted with one or two substituents selected from —$R_{11}$, —$OR_{11}$, —(CO)$R_{11}$, —(CO)$OR_{11}$, —O(CO)$R_{11}$, —(C1-C8 alkyl)-(CO)$OR_{11}$, —($SO_2$)$R_{11}$, —($SO_2$)$OR_{11}$, —(C1-C8 alkyl)-($SO_2$)$R_{11}$, —(CO)N($R_{12}$)$_2$ or —($SO_2$)N($R_{12}$)$_2$; the "C1-C8 alkyl", "C2-C8 alkenyl" or "C2-C8 alkynyl" is each independently unsubstituted or substituted with halogen; the "C3-C8 cycloalkyl", "C3-C8 cycloalkyl C1-C8 alkyl", "C3-C8 cycloalkenyl", "C3-C8 cycloalkenyl C1-C8 alkyl", "aryl", "aryl C1-C8 alkyl", "heterocyclyl" or "heterocyclyl C1-C8 alkyl" is each independently unsubstituted or substituted with one to four substituents selected from oxo, halogen, cyano, nitro, C1-C8 alkyl, halogenated C1-C8 alkyl, benzyl, —$OR_{14}$, —$SR_{14}$, —(CO)$OR_{14}$, —($SO_2$)$R_{14}$, —N($R_{14}$)$_2$ or —O—(C1-C8 alkyl)-(CO)$OR_{14}$, or two adjacent carbon atoms on the ring together with —$OCH_2CH_2$— or —$OCH_2O$— form a fused ring; the "5- to 8-membered carbocyclyl or oxygen-, sulfur- or nitrogen-containing heterocyclyl" is unsubstituted or substituted with one to four substituents selected from C1-C8 alkyl, C1-C8 alkoxycarbonyl or benzyl, or forms a fused ring structure with aryl or heterocyclyl;

More preferably, $X_4$, $X_5$ each independently represent hydrogen, halogen, cyano, nitro, —(C1-C6 alkyl)$_n$-$OR_{15}$, —(C1-C6 alkyl)$_n$-$SR_{15}$, —(C1-C6 alkyl)$_n$-(CO)$R_{15}$, —(C1-C6 alkyl)$_n$-O(CO)$R_{15}$, —(C1-C6 alkyl)$_n$-(CO)$OR_{15}$, —(C1-C6 alkyl)$_n$-(CO)$SR_{15}$, aminocarbonyl, C1-C6 alkyl, C2-C6 alkenyl, C2-C6 alkynyl, C3-C6 cycloalkyl, C3-C6 cycloalkyl C1-C6 alkyl, C3-C6 cycloalkenyl, C3-C6 cycloalkenyl C1-C6 alkyl, aryl, aryl C1-C6 alkyl, heterocyclyl or heterocyclyl C1-C6 alkyl, or the $CX_4X_5$ group together forms 5- to 8-membered carbocyclyl or oxygen-, sulfur- or nitrogen-containing heterocyclyl; wherein, the "aminocarbonyl" is unsubstituted or substituted with one or two substituents selected from —$R_{11}$, —$OR_{11}$, —(CO)$R_{11}$, —(CO)$OR_{11}$, —O(CO)$R_{11}$, —(C1-C6 alkyl)-(CO)$OR_{11}$, —($SO_2$)$R_{11}$, —($SO_2$)$OR_{11}$, —(C1-C6 alkyl)-($SO_2$)$R_{11}$, —(CO)N($R_{12}$)$_2$ or —($SO_2$)N($R_{12}$)$_2$; the "C1-C6 alkyl", "C2-C6 alkenyl" or "C2-C6 alkynyl" is each independently unsubstituted or substituted with halogen; the "C3-C6 cycloalkyl", "C3-C6 cycloalkyl C1-C6 alkyl", "C3-C6 cycloalkenyl", "C3-C6 cycloalkenyl C1-C6 alkyl", "aryl", "aryl C1-C6 alkyl", "heterocyclyl" or "heterocyclyl C1-C6 alkyl" is each independently unsubstituted or substituted with one, two or three substituents selected from oxo, halogen, cyano, nitro, C1-C6 alkyl, halogenated C1-C6 alkyl, benzyl, —$OR_{14}$, —$SR_{14}$, —(CO)$OR_{14}$, —($SO_2$)$R_{14}$, —N($R_{14}$)$_2$ or —O—(C1-C6 alkyl)-(CO)$OR_{14}$, or two adjacent carbon atoms on the ring together with —$OCH_2CH_2$— or —$OCH_2O$— form a fused ring; the "5- to 8-membered carbocyclyl or oxygen-, sulfur- or nitrogen-containing heterocyclyl" is unsubstituted or substituted with one, two or three substituents selected from C1-C6 alkyl, C1-C6 alkoxycarbonyl or benzyl, or forms a fused ring structure with aryl or heterocyclyl;

Further preferably, $X_4$, $X_5$ each independently represent hydrogen, halogen, cyano, nitro, —(C1-C3 alkyl)$_n$-$OR_{15}$, —(C1-C3 alkyl)$_n$-$SR_{15}$, —(C1-C3 alkyl)$_n$-(CO)$R_{15}$, —(C1-C3 alkyl)$_n$-O(CO)$R_{15}$, —(C1-C3 alkyl)$_n$-(CO)$OR_{15}$, —(C1-C3 alkyl)$_n$-(CO)$SR_{15}$, aminocarbonyl, C1-C6 alkyl, C2-C6 alkenyl, C2-C6 alkynyl, C3-C6 cycloalkyl, C3-C6 cycloalkyl C1-C3 alkyl, C3-C6 cycloalkenyl, C3-C6 cycloalkenyl C1-C3 alkyl, aryl, aryl C1-C3 alkyl, heterocyclyl or heterocyclyl C1-C3 alkyl, or the $CX_4X_5$ group together forms a 5- to 8-membered saturated carbocyclyl,

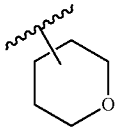 or 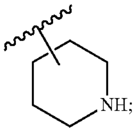

wherein, the "aminocarbonyl" is unsubstituted or substituted with one or two substituents selected from —$R_{11}$, —$OR_{11}$, —(CO)$R_{11}$, —(CO)$OR_{11}$, —O(CO)$R_{11}$, —(C1-C3 alkyl)-(CO)$OR_{11}$, —($SO_2$)$R_{11}$, —($SO_2$)$OR_{11}$, —(C1-C3 alkyl)-($SO_2$)$R_{11}$, —(CO)N($R_{12}$)$_2$ or —($SO_2$)N($R_{12}$)$_2$; the "C1-C6 alkyl", "C2-C6 alkenyl" or "C2-C6 alkynyl" is each independently unsubstituted or substituted with halogen; the "C3-C6 cycloalkyl", "C3-C6 cycloalkyl C1-C3 alkyl", "C3-C6 cycloalkenyl", "C3-C6 cycloalkenyl C1-C3 alkyl", "aryl", "aryl C1-C3 alkyl", "heterocyclyl" or "heterocyclyl C1-C3 alkyl" is each independently unsubstituted or substituted with one, two or three substituents selected from oxo, halogen, cyano, nitro, C1-C6 alkyl, halogenated C1-C6 alkyl, benzyl, —$OR_{14}$, —$SR_{14}$, —(CO)$OR_{14}$, —($SO_2$)$R_{14}$, —N($R_{14}$)$_2$ or —O—(C1-C3 alkyl)-(CO)$OR_{14}$, or two adjacent carbon atoms on the ring together with —$OCH_2CH_2$— or —$OCH_2O$— form a fused ring; the "5- to 8-membered saturated carbocyclyl,

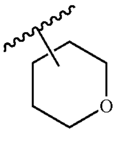 or 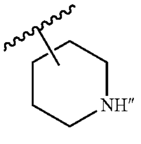

is unsubstituted or substituted with one, two or three substituents selected from C1-C6 alkyl, C1-C6 alkoxycarbonyl or benzyl, or forms a fused ring structure with aryl or thienyl;

Preferably, $R_1$, $R_2$ each independently represent hydrogen, cyano, C1-C8 alkyl, C2-C8 alkenyl, C2-C8 alkynyl, formyl C1-C8 alkyl, cyano C1-C8 alkyl, amino, amino C1-C8 alkyl, aminocarbonyl, aminocarbonyl C1-C8 alkyl, aminosulfonyl, C3-C8 cycloalkyl, C3-C8 cycloalkyl C1-C8 alkyl, C3-C8 cycloalkenyl, C3-C8 cycloalkenyl C1-C8 alkyl, heterocyclyl, heterocycyl C1-C8 alkyl, aryl, aryl C1-C8 alkyl, $R_4R_5$N—(CO)—$NR_3$—,

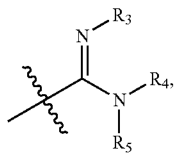

$R_3$—S(O)$_m$—(C1-C8 alkyl)$_n$-, $R_3$—O—(C1-C8 alkyl)$_n$-, $R_3$—(CO)—(C1-C8 alkyl)$_n$-, $R_3$—O—(C1-C8 alkyl)$_n$-(CO)—, $R_3$—(CO)—O—(C1-C8 alkyl)$_n$-, $R_3$—S—(CO)—(C1-C8 alkyl)$_n$-, $R_3$—O—(CO)—(C1-C8 alkyl)- or $R_3$—O—(CO)—O—(C1-C8 alkyl)-; wherein, the "C1-C8 alkyl", "C2-C8 alkenyl" or "C2-C8 alkynyl" is each independently unsubstituted or substituted with halogen;

the "amino", "amino C1-C8 alkyl", "aminocarbonyl", "aminocarbonyl C1-C8 alkyl" or "aminosulfonyl" is each independently unsubstituted or substituted with one or two substituents selected from —$R_{11}$, —$OR_{11}$, —(CO)$R_{11}$, —(CO)$OR_{11}$, —O(CO)$R_{11}$, —(C1-C8 alkyl)-(CO)$OR_{11}$, —($SO_2$)$R_{11}$, —($SO_2$)$OR_{11}$, —(C1-C8 alkyl)-($SO_2$)$R_{11}$, —(CO)N($R_{12}$)$_2$ or —($SO_2$)N($R_{12}$)$_2$;

the "C3-C8 cycloalkyl", "C3-C8 cycloalkyl C1-C8 alkyl", "C3-C8 cycloalkenyl", "C3-C8 cycloalkenyl C1-C8 alkyl", "heterocyclyl", "heterocyclyl C1-C8 alkyl", "aryl" or "aryl C1-C8 alkyl" is each independently unsubstituted or substituted with one to four substituents selected from oxo, halogen, cyano, nitro, C1-C8 alkyl, halogenated C1-C8 alkyl, benzyl, —$OR_{14}$, —$SR_{14}$, —(CO)$OR_{14}$, —($SO_2$)$R_{14}$, —N($R_{14}$)$_2$ or —O—(C1-C8 alkyl)-(CO)$OR_{14}$;

More preferably, $R_1$, $R_2$ each independently represent hydrogen, cyano, C1-C6 alkyl, C2-C6 alkenyl, C2-C6 alkynyl, formyl C1-C6 alkyl, cyano C1-C6 alkyl, amino, amino C1-C6 alkyl, aminocarbonyl, aminocarbonyl C1-C6 alkyl, aminosulfonyl, C3-C6 cycloalkyl, C3-C6 cycloalkyl C1-C6 alkyl, C3-C6 cycloalkenyl, C3-C6 cycloalkenyl C1-C6 alkyl, heterocyclyl, heterocyclyl C1-C6 alkyl, aryl, aryl C1-C6 alkyl, $R_4R_5N$—(CO)—$NR_3$—,

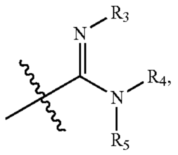

$R_3$—$S(O)_m$—$(C1\text{-}C6\ alkyl)_n$-, $R_3$—O—$(C1\text{-}C6\ alkyl)_n$-, $R_3$—(CO)—$(C1\text{-}C6\ alkyl)_n$-, $R_3$—O—$(C1\text{-}C6\ alkyl)_n$-(CO)—, $R_3$—(CO)—O—$(C1\text{-}C6\ alkyl)_n$-, $R_3$—S—(CO)—$(C1\text{-}C6\ alkyl)_n$-, $R_3$—O—(CO)—(C1-C6 alkyl)- or $R_3$—O—(CO)—O—(C1-C6 alkyl)-; wherein, the "C1-C6 alkyl", "C2-C6 alkenyl" or "C2-C6 alkynyl" is each independently unsubstituted or substituted with halogen;

the "amino", "amino C1-C6 alkyl", "aminocarbonyl", "aminocarbonyl C1-C6 alkyl" or "aminosulfonyl" is each independently unsubstituted or substituted with one or two substituents selected from —$R_{11}$, —$OR_{11}$, —(CO)$R_{11}$, —(CO)$OR_{11}$, —O(CO)$R_{11}$, —(C1-C6 alkyl)-(CO)$OR_{11}$, —$(SO_2)R_{11}$, —$(SO_2)OR_{11}$, —(C1-C6 alkyl)-$(SO_2)R_{11}$, —(CO)$N(R_{12})_2$ or —$(SO_2)N(R_{12})_2$;

the "C3-C6 cycloalkyl", "C3-C6 cycloalkyl C1-C6 alkyl", "C3-C6 cycloalkenyl", "C3-C6 cycloalkenyl C1-C6 alkyl", "heterocyclyl", "heterocyclyl C1-C6 alkyl", "aryl" or "aryl C1-C6 alkyl" is each independently unsubstituted or substituted with one, two or three substituents selected from oxo, halogen, cyano, nitro, C1-C6 alkyl, halogenated C1-C6 alkyl, benzyl, —$OR_{14}$, —$SR_{14}$, —(CO)$OR_{14}$, —$(SO_2)R_{14}$, —$N(R_{14})_2$ or —O—(C1-C6 alkyl)-(CO)$OR_{14}$;

Preferably, $R_6$, $R_7$ each independently represent hydrogen, C1-C8 alkyl or halogenated C1-C8 alkyl;

More preferably, $R_6$, $R_7$ each independently represent hydrogen, C1-C6 alkyl or halogenated C1-C6 alkyl;

Preferably, R' each independently represents hydrogen, halogen, C1-C8 alkoxy, C1-C8 alkoxy C1-C8 alkyl, C1-C8 alkyl, C2-C8 alkenyl, C2-C8 alkynyl, C3-C8 cycloalkyl, C3-C8 cycloalkyl C1-C8 alkyl, C3-C8 cycloalkenyl, C3-C8 cycloalkenyl C1-C8 alkyl, aryl, aryl C1-C8 alkyl, heterocyclyl or heterocyclyl C1-C8 alkyl, or the $C(R')_2$ group in —(CO)O—(C1-C8 alkyl)-O—N═$C(R')_2$ together forms a 5- to 6-membered saturated carbocyclyl; wherein, the "C1-C8 alkyl", "C2-C8 alkenyl" or "C2-C8 alkynyl" is each independently unsubstituted or substituted with halogen; the "C3-C8 cycloalkyl", "C3-C8 cycloalkyl C1-C8 alkyl", "C3-C8 cycloalkenyl", "C3-C8 cycloalkenyl C1-C8 alkyl", "aryl", "aryl C1-C8 alkyl", "heterocyclyl" or "heterocyclyl C1-C8 alkyl" is each independently unsubstituted or substituted with one to four substituents selected from oxo, halogen, cyano, nitro, C1-C8 alkyl, halogenated C1-C8 alkyl, benzyl, —$OR_{14}$, —$SR_{14}$, —(CO)$OR_{14}$, —$(SO_2)R_{14}$, —$N(R_{14})_2$ or —O—(C1-C8 alkyl)-(CO)$OR_{14}$;

More preferably, R' each independently represents hydrogen, halogen, C1-C6 alkoxy, C1-C6 alkoxy C1-C6 alkyl, C1-C6 alkyl, C2-C6 alkenyl, C2-C6 alkynyl, C3-C6 cycloalkyl, C3-C6 cycloalkyl C1-C6 alkyl, C3-C6 cycloalkenyl, C3-C6 cycloalkenyl C1-C6 alkyl, aryl, aryl C1-C6 alkyl, heterocyclyl or heterocyclyl C1-C6 alkyl, or the $C(R')_2$ group in —(CO)O—(C1-C6 alkyl)-O—N═$C(R')_2$ together forms a 5- to 6-membered saturated carbocyclyl; wherein, the "C1-C6 alkyl", "C2-C6 alkenyl" or "C2-C6 alkynyl" is each independently unsubstituted or substituted with halogen; the "C3-C6 cycloalkyl", "C3-C6 cycloalkyl C1-C6 alkyl", "C3-C6 cycloalkenyl", "C3-C6 cycloalkenyl C1-C6 alkyl", "aryl", "aryl C1-C6 alkyl", "heterocyclyl" or "heterocyclyl C1-C6 alkyl" is each independently unsubstituted or substituted with one, two or three substituents selected from oxo, halogen, cyano, nitro, C1-C6 alkyl, halogenated C1-C6 alkyl, benzyl, —$OR_{14}$, —$SR_{14}$, —(CO)$OR_{14}$, —$(SO_2)R_{14}$, —$N(R_{14})_2$ or —O—(C1-C6 alkyl)-(CO)$OR_{14}$;

Preferably, R" each independently represents C1-C8 alkyl, C2-C8 alkenyl, C2-C8 alkynyl, C3-C8 cycloalkyl, C3-C8 cycloalkyl C1-C8 alkyl, C3-C8 cycloalkenyl, C3-C8 cycloalkenyl C1-C8 alkyl, aryl, aryl C1-C8 alkyl, aryl C2-C8 alkenyl, heterocyclyl, heterocyclyl C1-C8 alkyl or heterocyclyl C2-C8 alkenyl; wherein, the "C1-C8 alkyl", "C2-C8 alkenyl" or "C2-C8 alkynyl" is each independently unsubstituted or substituted with one to three substituents selected from halogen, cyano, tri-C1-C8 alkylsilyl, —$OR_{13}$, —$SR_{13}$, —O(CO)$R_{13}$, —(CO)$R_{13}$, —(CO)$OR_{13}$ or —O(CO)$OR_{13}$; the "C3-C8 cycloalkyl", "C3-C8 cycloalkyl C1-C8 alkyl", "C3-C8 cycloalkenyl", "C3-C8 cycloalkenyl C1-C8 alkyl", "aryl", "aryl C1-C8 alkyl", "aryl C2-C8 alkenyl", "heterocyclyl", "heterocyclyl C1-C8 alkyl" or "heterocyclyl C2-C8 alkenyl" is each independently unsubstituted or substituted with one to four substituents selected from oxo, halogen, cyano, nitro, C1-C8 alkyl, halogenated C1-C8 alkyl, benzyl, —$OR_{14}$, —$SR_{14}$, —(CO)$OR_{14}$, —$(SO_2)R_{14}$, —$N(R_{14})_2$ or —O—(C1-C8 alkyl)-(CO)$OR_{14}$;

More preferably, R" each independently represents C1-C6 alkyl, C2-C6 alkenyl, C2-C6 alkynyl, C3-C6 cycloalkyl, C3-C6 cycloalkyl C1-C6 alkyl, C3-C6 cycloalkenyl, C3-C6 cycloalkenyl C1-C6 alkyl, aryl, aryl C1-C6 alkyl, aryl C2-C6 alkenyl, heterocyclyl, heterocyclyl C1-C6 alkyl or heterocyclyl C2-C6 alkenyl; wherein, the "C1-C6 alkyl", "C2-C6 alkenyl" or "C2-C6 alkynyl" is each independently unsubstituted or substituted with one, two or three substituents selected from halogen, cyano, tri-C1-C8 alkylsilyl, —$OR_{13}$, —$SR_{13}$, —O(CO)$R_{13}$, —(CO)$R_{13}$, —(CO)$OR_{13}$ or —O(CO)$OR_{13}$; the "C3-C6 cycloalkyl", "C3-C6 cycloalkyl C1-C6 alkyl", "C3-C6 cycloalkenyl", "C3-C6 cycloalkenyl C1-C6 alkyl", "aryl", "aryl C1-C6 alkyl", "aryl C2-C6 alkenyl", "heterocyclyl", "heterocyclyl C1-C6 alkyl" or "heterocyclyl C2-C6 alkenyl" is each independently unsubstituted or substituted with one, two or three substituents selected from oxo, halogen, cyano, nitro, C1-C6 alkyl, halogenated C1-C6 alkyl, benzyl, —$OR_{14}$, —$SR_{14}$, —(CO)$OR_{14}$, —$(SO_2)R_{14}$, —$N(R_{14})_2$ or —O—(C1-C6 alkyl)-(CO)$OR_{14}$;

Preferably, $R_3$, $R_4$, $R_5$, $R_{15}$ each independently represent hydrogen, C1-C8 alkyl, C2-C8 alkenyl, C2-C8 alkynyl, C3-C8 cycloalkyl, C3-C8 cycloalkyl C1-C8 alkyl, C3-C8 cycloalkenyl, C3-C8 cycloalkenyl C1-C8 alkyl, heterocyclyl, heterocyclyl C1-C8 alkyl, aryl or aryl C1-C8 alkyl; wherein, the "C1-C8 alkyl", "C2-C8 alkenyl" or "C2-C8 alkynyl" is each independently unsubstituted or substituted with halogen; the "C3-C8 cycloalkyl", "C3-C8 cycloalkyl C1-C8 alkyl", "C3-C8 cycloalkenyl", "C3-C8 cycloalkenyl C1-C8 alkyl", "heterocyclyl", "heterocyclyl C1-C8 alkyl", "aryl" or "aryl C1-C8 alkyl" is each independently unsubstituted or substituted with one to four substituents selected from oxo, halogen, cyano, nitro, C1-C8 alkyl, halogenated C1-C8 alkyl, benzyl, —$OR_{14}$, —$SR_{14}$, —(CO)$OR_{14}$, —($SO_2$)$R_{14}$, —N($R_{14}$)$_2$ or —O—(C1-C8 alkyl)-(CO)$OR_{14}$;

More preferably, $R_3$, $R_4$, $R_5$, $R_{15}$ each independently represent hydrogen, C1-C6 alkyl, C2-C6 alkenyl, C2-C6 alkynyl, C3-C6 cycloalkyl, C3-C6 cycloalkyl C1-C6 alkyl, C3-C6 cycloalkenyl, C3-C6 cycloalkenyl C1-C6 alkyl, heterocyclyl, heterocyclyl C1-C6 alkyl, aryl or aryl C1-C6 alkyl; wherein, the "C1-C6 alkyl", "C2-C6 alkenyl" or "C2-C6 alkynyl" is each independently unsubstituted or substituted with halogen; the "C3-C6 cycloalkyl", "C3-C6 cycloalkyl C1-C6 alkyl", "C3-C6 cycloalkenyl", "C3-C6 cycloalkenyl C1-C6 alkyl", "heterocyclyl", "heterocyclyl C1-C6 alkyl", "aryl" or "aryl C1-C6 alkyl" is each independently unsubstituted or substituted with one, two or three substituents selected from oxo, halogen, cyano, nitro, C1-C6 alkyl, halogenated C1-C6 alkyl, benzyl, —$OR_{14}$, —$SR_{14}$, —(CO)$OR_{14}$, —($SO_2$)$R_{14}$, —N($R_{14}$)$_2$ or —O—(C1-C6 alkyl)-(CO)$OR_{14}$;

Further preferably, $R_{15}$ each independently represents hydrogen, C1-C6 alkyl, C2-C6 alkenyl, C2-C6 alkynyl, C3-C6 cycloalkyl, C3-C6 cycloalkyl C1-C3 alkyl, C3-C6 cycloalkenyl, C3-C6 cycloalkenyl C1-C3 alkyl, heterocyclyl, heterocyclyl C1-C3 alkyl, aryl or aryl C1-C3 alkyl; wherein, the "C1-C6 alkyl", "C2-C6 alkenyl" or "C2-C6 alkynyl" is each independently unsubstituted or substituted with halogen; the "C3-C6 cycloalkyl", "C3-C6 cycloalkyl C1-C3 alkyl", "C3-C6 cycloalkenyl", "C3-C6 cycloalkenyl C1-C3 alkyl", "heterocyclyl", "heterocyclyl C1-C3 alkyl", "aryl" or "aryl C1-C3 alkyl" is each independently unsubstituted or substituted with one, two or three substituents selected from oxo, halogen, cyano, nitro, C1-C6 alkyl, halogenated C1-C6 alkyl, benzyl, —$OR_{14}$, —$SR_{14}$, —(CO)$OR_{14}$, —($SO_2$)$R_{14}$, —N($R_{14}$)$_2$ or —O—(C1-C3 alkyl)-(CO)$OR_{14}$;

Preferably, Rn each independently represents C1-C8 alkyl, C2-C8 alkenyl, C2-C8 alkynyl, C3-C8 cycloalkyl, C3-C8 cycloalkyl C1-C8 alkyl, C3-C8 cycloalkenyl, C3-C8 cycloalkenyl C1-C8 alkyl, phenyl or benzyl; wherein, the "C1-C8 alkyl", "C2-C8 alkenyl" or "C2-C8 alkynyl" is each independently unsubstituted or substituted with halogen; the "phenyl" or "benzyl" is each independently unsubstituted or substituted with one to four substituents selected from halogen, cyano, nitro, C1-C8 alkyl, halogenated C1-C8 alkyl, C1-C8 alkoxycarbonyl, C1-C8 alkylthio, C1-C8 alkylsulfonyl, C1-C8 alkoxy or halogenated C1-C8 alkoxy;

More preferably, $R_{11}$ each independently represents C1-C6 alkyl, C2-C6 alkenyl, C2-C6 alkynyl, C3-C6 cycloalkyl, C3-C6 cycloalkyl C1-C6 alkyl, C3-C6 cycloalkenyl, C3-C6 cycloalkenyl C1-C6 alkyl, phenyl or benzyl; wherein, the "C1-C6 alkyl", "C2-C6 alkenyl" or "C2-C6 alkynyl" is each independently unsubstituted or substituted with halogen; the "phenyl" or "benzyl" is each independently unsubstituted or substituted with one, two or three substituents selected from halogen, cyano, nitro, C1-C6 alkyl, halogenated C1-C6 alkyl, C1-C6 alkoxycarbonyl, C1-C6 alkylthio, C1-C6 alkylsulfonyl, C1-C6 alkoxy or halogenated C1-C6 alkoxy;

Further preferably, $R_{11}$ each independently represents C1-C6 alkyl, C2-C6 alkenyl, C2-C6 alkynyl, C3-C6 cycloalkyl, C3-C6 cycloalkyl C1-C3 alkyl, C3-C6 cycloalkenyl, C3-C6 cycloalkenyl C1-C3 alkyl, phenyl or benzyl; wherein, the "C1-C6 alkyl", "C2-C6 alkenyl" or "C2-C6 alkynyl" is each independently unsubstituted or substituted with halogen; the "phenyl" or "benzyl" is each independently unsubstituted or substituted with one, two or three substituents selected from halogen, cyano, nitro, C1-C6 alkyl, halogenated C1-C6 alkyl, C1-C6 alkoxycarbonyl, C1-C6 alkylthio, C1-C6 alkylsulfonyl, C1-C6 alkoxy or halogenated C1-C6 alkoxy;

Preferably, $R_{12}$ each independently represents hydrogen, C1-C8 alkyl, C2-C8 alkenyl, C2-C8 alkynyl, C1-C8 alkoxy, C1-C8 alkylsulfonyl, C3-C8 cycloalkyl, C3-C8 cycloalkyl C1-C8 alkyl, C3-C8 cycloalkenyl or C3-C8 cycloalkenyl C1-C8 alkyl; or the N($R_{12}$)$_2$ group in —(CO)N($R_{12}$)$_2$ or —($SO_2$)N($R_{12}$)$_2$ each independently represents heterocyclyl

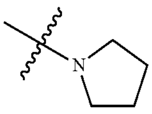, 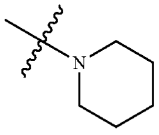 or 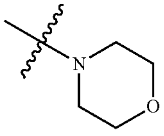

with nitrogen atom at 1-position;

More preferably, $R_{12}$ each independently represents hydrogen, C1-C6 alkyl, C2-C6 alkenyl, C2-C6 alkynyl, C1-C6 alkoxy, C1-C6 alkylsulfonyl, C3-C6 cycloalkyl, C3-C6 cycloalkyl C1-C6 alkyl, C3-C6 cycloalkenyl or C3-C6 cycloalkenyl C1-C6 alkyl; or the N($R_{12}$)$_2$ group in —(CO)N($R_{12}$)$_2$ or —($SO_2$)N($R_{12}$)$_2$ each independently represents heterocyclyl

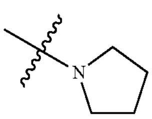, 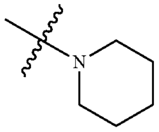 or 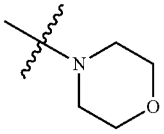

with nitrogen atom at 1-position;

Further preferably, $R_{12}$ each independently represents hydrogen, C1-C6 alkyl, C2-C6 alkenyl, C2-C6 alkynyl, C1-C6 alkoxy, C1-C6 alkylsulfonyl, C3-C6 cycloalkyl, C3-C6 cycloalkyl C1-C3 alkyl, C3-C6 cycloalkenyl or C3-C6 cycloalkenyl C1-C3 alkyl; or the N($R_{12}$)$_2$ group in —(CO)N($R_{12}$)$_2$ or —($SO_2$)N($R_{12}$)$_2$ each independently represents heterocyclyl

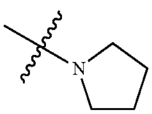, 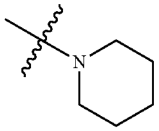 or 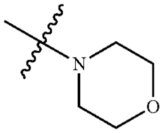

with nitrogen atom at 1-position;

Preferably, $R_{13}$ each independently represents C1-C8 alkyl, C2-C8 alkenyl, C2-C8 alkynyl, C3-C8 cycloalkyl, phenyl or phenyl substituted with one to four substituents selected from halogen, cyano, nitro, C1-C8 alkyl, halogenated C1-C8 alkyl, C1-C8 alkoxy, halogenated C1-C8 alkoxy, C1-C8 alkoxycarbonyl, C1-C8 alkylthio, C1-C8 alkylsulfonyl or phenoxyl substituted with one to four substituents selected from halogen, cyano, nitro, C1-C8 alkyl, halogenated C1-C8 alkyl, C1-C8 alkoxy or halogenated C1-C8 alkoxy;

More preferably, $R_{13}$ each independently represents C1-C6 alkyl, C2-C6 alkenyl, C2-C6 alkynyl, C3-C6 cycloalkyl, phenyl or phenyl substituted with one, two or three substituents selected from halogen, cyano, nitro, C1-C6 alkyl, halogenated C1-C6 alkyl, C1-C6 alkoxy, halogenated C1-C6 alkoxy, C1-C6 alkoxycarbonyl, C1-C6 alkylthio, C1-C6 alkylsulfonyl or phenoxyl substituted with one, two or three substituents selected from halogen, cyano, nitro, C1-C6 alkyl, halogenated C1-C6 alkyl, C1-C6 alkoxy or halogenated C1-C6 alkoxy;

Preferably, $R_{14}$ each independently represents hydrogen, C1-C8 alkyl, halogenated C1-C8 alkyl, phenyl or phenyl substituted with one to four substituents selected from halogen, cyano, nitro, C1-C8 alkyl, halogenated C1-C8 alkyl, C1-C8 alkoxycarbonyl, C1-C8 alkylthio, C1-C8 alkylsulfonyl, C1-C8 alkoxy or halogenated C1-C8 alkoxy;

More preferably, $R_{14}$ each independently represents hydrogen, C1-C6 alkyl, halogenated C1-C6 alkyl, phenyl or phenyl substituted with one, two or three substituents selected from halogen, cyano, nitro, C1-C6 alkyl, halogenated C1-C6 alkyl, C1-C6 alkoxycarbonyl, C1-C6 alkylthio, C1-C6 alkylsulfonyl, C1-C6 alkoxy or halogenated C1-C6 alkoxy;

Further preferably, $R_{14}$ each independently represents hydrogen, C1-C6 alkyl, halogenated C1-C6 alkyl, phenyl or phenyl substituted with one, two or three substituents selected from halogen, cyano, nitro, C1-C6 alkyl, halogenated C1-C6 alkyl, C1-C6 alkoxycarbonyl, C1-C6 alkylthio, C1-C6 alkylsulfonyl, C1-C6 alkoxy or halogenated C1-C6 alkoxy;

Further preferably, Y represents chlorine;

Z represents fluorine;

$X_1$, $X_2$, $X_3$ each independently represent hydrogen or C1-C6 alkyl;

$X_4$, $X_5$ each independently represent hydrogen, —(C1-C3 alkyl)$_n$-$OR_{15}$, —(CO)$OR_{15}$, C1-C6 alkyl, C3-C6 cycloalkyl, phenyl or heterocyclyl, or the $CX_4X_5$ group together forms a 5- to 6-membered saturated carbocyclyl; wherein, the "C3-C6 cycloalkyl", "phenyl" or "heterocyclyl" is each independently unsubstituted or substituted with one, two or three substituents selected from C1-C6 alkyl; the "heterocyclyl" is selected from

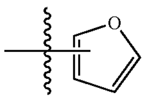 or 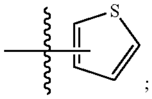 ;

$Q_1$, $Q_2$, $Q_3$ each independently represent oxygen or sulphur;

$R_1$, $R_2$ each independently represent C1-C6 alkyl;

$R_6$ represents C1-C6 alkyl;

$R_7$ represents halogenated C1-C6 alkyl (preferably trifluoromethyl);

$R_{15}$ each independently represents C1-C6 alkyl;

Further preferably, Q represents

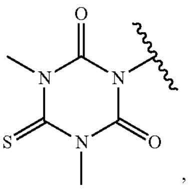 , 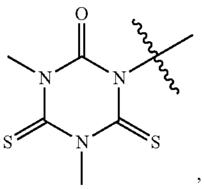 ,

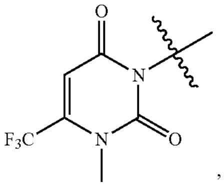 , 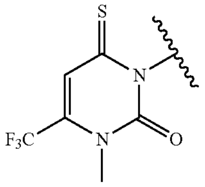 or

-continued

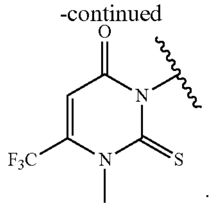 .

In the definition of the compound represented by the above Formula and all of the following structural formulas, the technical terms used, whether used alone or used in compound word, represent the following substituents: an alkyl having more than two carbon atoms may be linear or branched. For example, the alkyl in the compound word "-alkyl-(CO)$OR_{11}$" may be —$CH_2$—, —$CH_2CH_2$—, —CH($CH_3$)—, —C$(CH_3)_2$—, and the like. The alkyl is, for example, $C_1$ alkyl: methyl; $C_2$ alkyl: ethyl; $C_3$ alkyl: propyl such as n-propyl or isopropyl; $C_4$ alkyl: butyl such as n-butyl, isobutyl, tert-butyl or 2-butyl; $C_5$ alkyl: pentyl such as n-pentyl; $C_6$ alkyl: hexyl such as n-hexyl, isohexyl and 1,3-dimethylbutyl. Similarly, the alkenyl is, for example, vinyl, allyl, 1-methylprop-2-en-1-yl, 2-methylprop-2-en-1-yl, but-2-en-1-yl, butyl-3-en-1-yl, 1-methylbut-3-en-1-yl and 1-methylbut-2-en-1-yl. The alkynyl is, for example, ethynyl, propargyl, but-2-yn-1-yl, but-3-yn-1-yl, 1-methyl-but-3-yn-1-yl. The multiple bond(s) may be placed at any position of each unsaturated group. The cycloalkyl is a carbocyclic saturated ring system having, for example, three to six carbon atoms, such as cyclopropyl, cyclobutyl, cyclopentyl or cyclohexyl. Similarly, the cycloalkenyl is monocycloalkenyl having, for example, three to six carbon ring members, such as cyclopropenyl, cyclobutenyl, cyclopentenyl, and cyclohexenyl, wherein double bond can be at any position. Halogen is fluorine, chlorine, bromine or iodine.

Unless otherwise specified, the "aryl" of the present invention includes, but is not limited to, phenyl, naphthyl,

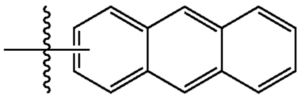 , or

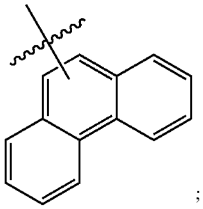 ;

the "heterocyclyl" not only includes, but is not limited to, saturated or unsaturated non-aromatic cyclic group,

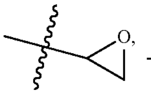 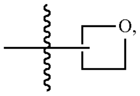 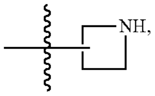

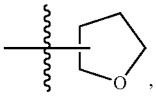 , 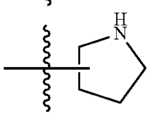 , 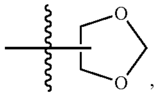 ,

-continued
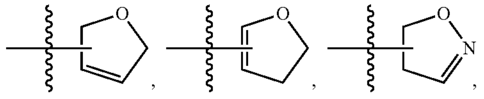
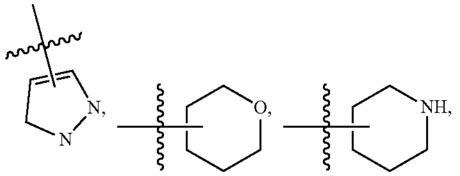
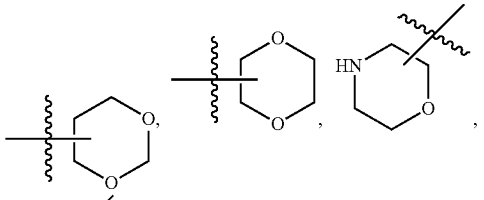
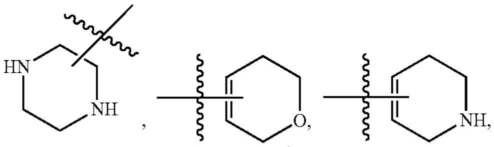
or
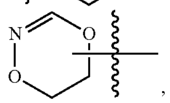
etc., but also includes, but is not limited to, “heteroaryl”, which is an aromatic cyclic group having, for example, 3 to 6 ring atoms and optionally being fused with a benzo ring, and 1 to 4 (for example, 1, 2, 3 or 4) heteroatoms of the ring are selected from the group consisting of oxygen, nitrogen and sulfur. For example
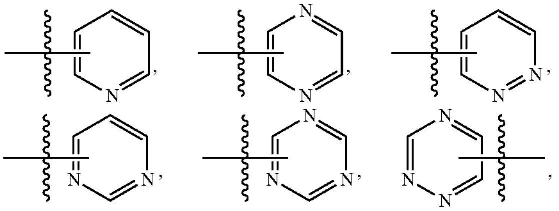
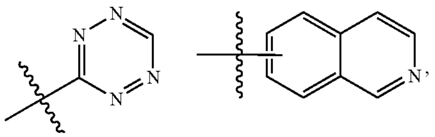
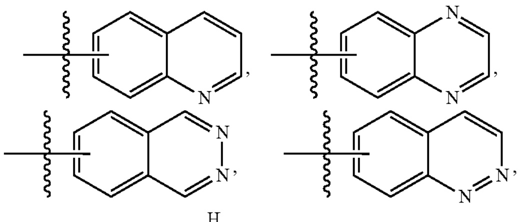
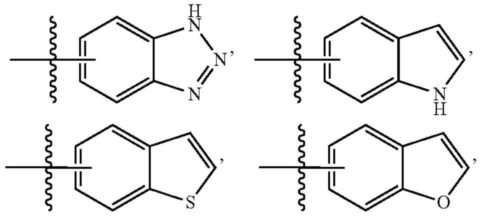
-continued
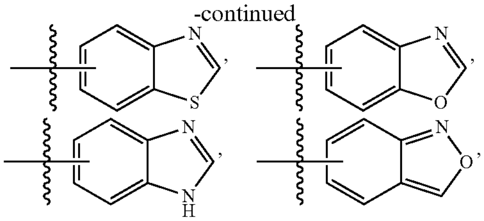
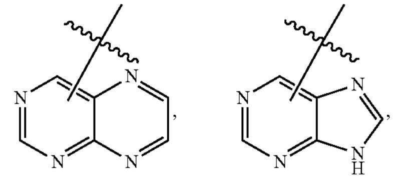
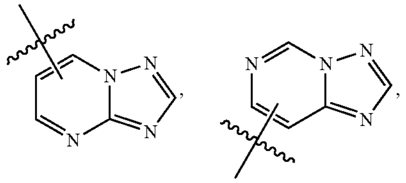
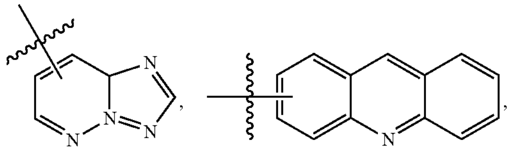
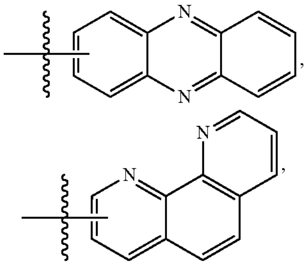
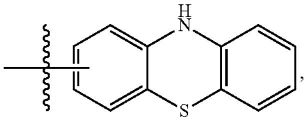
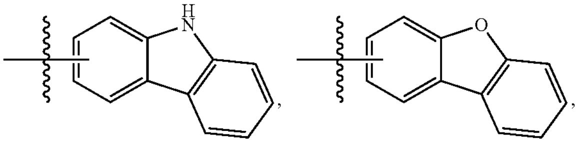
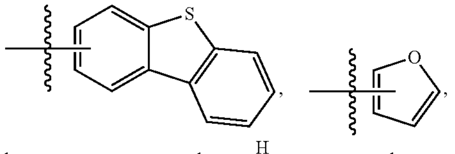
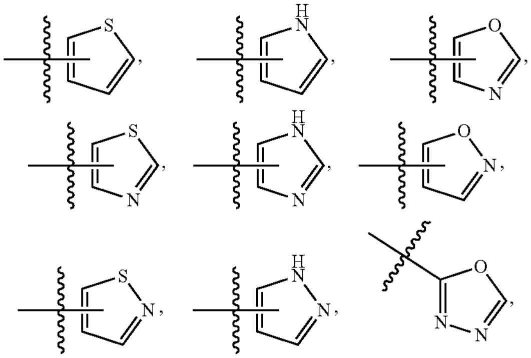

-continued

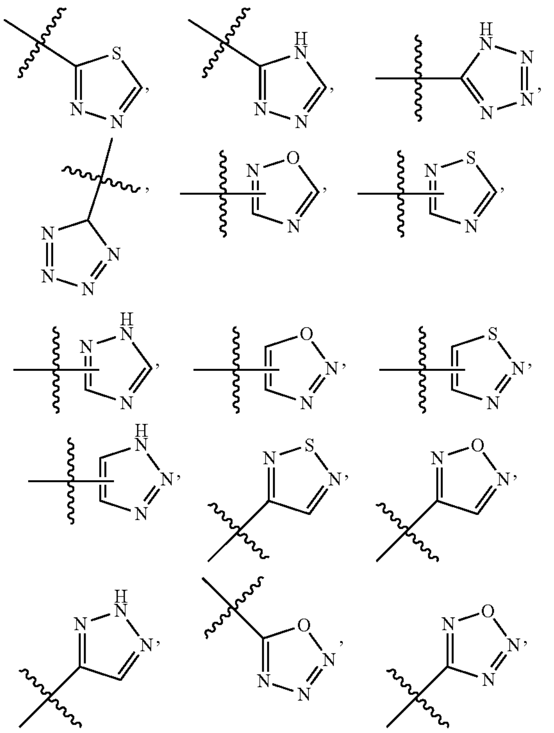

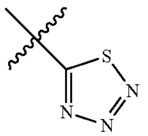

or

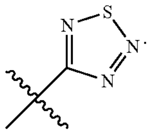

If a group is substituted by a group, which should be understood to mean that the group is substituted by one or more groups, which are same or different groups, selected from the mentioned groups. In addition, the same or different substitution characters contained in the same or different substituents are independently selected, and may be the same or different. This is also applicable to ring systems formed with different atoms and units. Meanwhile, the scope of the claims will exclude those compounds chemically unstable under standard conditions known to those skilled in the art.

In addition, unless specifically defined, a group (including heterocyclyl, aryl, etc.) without being specified a linking site may be attached at any site, including a C or N site; if it is substituted, the substituent may be substituted at any site as long as it comply with the valence bond theory. For example, if the heteroaryl

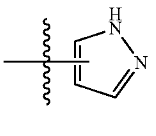

is substituted with one methyl, it can be

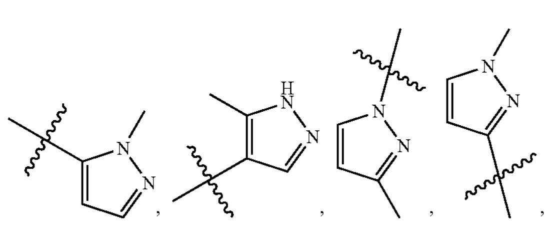

etc..

Depending on the property of substituents and the linkage manner thereof, the compound of Formula I and its derivatives may exist as a stereoisomer. For example, if a compound has one or more asymmetric carbon atoms, it may has enantiomers and diastereomers. The stereoisomer can be obtained from the mixtures obtained in the preparation by conventional separation methods, for example by chromatographic separation. The stereoisomer may also be prepared selectively by using stereoselective reactions and using optically active starting materials and/or auxiliaries. The present invention also relates to all stereoisomers and mixtures thereof which are included in the general Formula I but are not specifically defined.

A method for preparing the isoxazoline oxime formate compound comprises the following steps:

subjecting a compound as shown in general formula II and a compound as shown in general formula III to condensation reaction to obtain a compound as shown in general formula I, with the chemical reaction equation shown as follows:

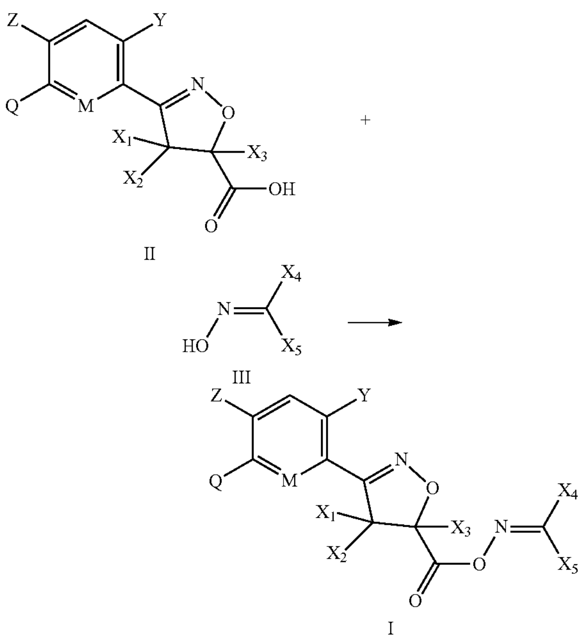

wherein, the substituents Q, Y, Z, $X_1$, $X_2$, $X_3$, $X_4$ and $X_5$ are as defined above.

The reaction is carried out under the action of base and condensing agent in the present of aprotic solvent.

The base is one or more selected from triethylamine, trimethylamine, DIPEA and DBU.

The condensing agent is PyBop, HATU or HOBt-EDCI.

The solvent is one or more mixed solvents selected from dichloromethane, dichlorethane, acetonitrile, N,N-dimethylformamide, N,N-dimethylacetamide, dimethylsulfoxide, tetrahydrofuran, toluene and xylene.

Wherein, the compound as shown in general formula II according to the present invention can be prepared by standard methods of organic chemistry. These methods are described in particular in patents WO00/50409, CN105753853A, U.S. Pat. No. 5,679,791, WO2012/041789, WO2019/101551, etc.

An herbicidal composition, which comprises at least one of the isoxazoline oxime formate compound in a herbicidally effective amount; preferably, further comprises a formulation auxiliary.

A method for controlling a weed, which comprises applying at least one of the isoxazoline oxime formate compound or the herbicidal composition in a herbicidally effective amount on a plant or a weed area.

Use of at least one of the isoxazoline oxime formate compound or the herbicidal composition for controlling a weed; preferably, the isoxazoline oxime formate compound is used to control a weed in a useful crop, the useful crop is a transgenic crop or a crop treated by genome editing technique.

The compounds of the formula I according to the invention have an outstanding herbicidal activity against a broad spectrum of economically important monocotyledonous and dicotyledonous harmful plants. The active compounds also act efficiently on perennial weeds which produce shoots from rhizomes, root stocks or other perennial organs and which are difficult to control. In this context, it is generally immaterial whether the substances are applied pre-sowing, pre-emergence or post-emergence. Specifically, examples may be mentioned of some representatives of the monocotyledonous and dicotyledonous weed flora which can be controlled by the compounds according to the invention, without these being a restriction to certain species. Examples of weed species on which the active compounds act efficiently are, from amongst the monocotyledons, *Avena, Lolium, Alopecurus, Phalaris, Echinochloa, Digitaria, Setaria* and also *Cyperus* species from the annual sector and from amongst the perennial species *Agropyron, Cynodon, Imperata* and Sorghum, and also perennial *Cyperus* species.

In the case of the dicotyledonous weed species, the spectrum of action extends to species such as, for example, *Galium, Viola, Veronica, Lamium, Stellaria, Amaranthus, Sinapis, Ipomoea, Sida, Matricaria* and *Abutilon* from amongst the annuals, and *Convolvulus, Cirsium, Rumex* and *Artemisia* in the case of the perennial weeds. The active compounds according to the invention also effect outstanding control of harmful plants which occur under the specific conditions of rice growing such as, for example, *Echinochloa, Sagittaria, Alisma, Eleocharis, Scirpus* and *Cyperus*. If the compounds according to the invention are applied to the soil surface prior to germination, then the weed seedlings are either prevented completely from emerging, or the weeds grow until they have reached the cotyledon stage but then their growth stops, and, eventually, after three to four weeks have elapsed, they die completely. In particular, the compounds according to the invention exhibit excellent activity against *Apera* spica venti, *Chenopodium album, Lamium purpureum, Polygonum convulvulus, Stellaria media, Veronica hederifolia, Veronica persica*, Viola tricolor and against *Amaranthus, Galium* and *Kochia* species.

Although the compounds according to the invention have an excellent herbicidal activity against monocotyledonous and dicotyledonous weeds, crop plants of economically important crops such as, for example, wheat, barley, rye, rice, corn, sugarbeet, cotton and soya, are not damaged at all, or only to a negligible extent. In particular, they have excellent compatibility in cereals, such as wheat, barley and corn, in particular wheat. For these reasons, the present compounds are highly suitable for selectively controlling undesirable plant growth in plantings for agricultural use or in plantings of ornamentals.

Owing to their herbicidal properties, these active compounds can also be employed for controlling harmful plants in crops of known or still to be developed genetically engineered plants. The transgenic plants generally have particularly advantageous properties, for example resistance to certain pesticides, in particular certain herbicides, resistance to plant diseases or causative organisms of plant diseases, such as certain insects or microorganisms such as fungi, bacteria or viruses. Other particular properties relate, for example, to the quantity, quality, storage-stability, composition and to specific ingredients of the harvested product. Thus, transgenic plants having an increased starch content or a modified quality of the starch or those having a different fatty acid composition of the harvested produce are known.

The use of the compounds of the formula I according to the invention or their salts in economically important transgenic crops of useful and ornamental plants, for example of cereal, such as wheat, barley, rye, oats, millet, rice, maniok and corn, or else in crops of sugarbeet, cotton, soya, rapeseed, potato, tomato, pea and other vegetable species is preferred. The compounds of the formula I can preferably be used as herbicides in crops of useful plants which are resistant or which have been made resistant by genetic engineering toward the phytotoxic effects of the herbicides.

Conventional ways for preparing novel plants which have modified properties compared to known plants comprise, for example, traditional breeding methods and the generation of mutants. Alternatively, novel plants having modified properties can be generated with the aid of genetic engineering methods (see, for example, EP-A 0 221 044, EP-A 0 131 624). For example, there have been described several cases of:

- genetically engineered changes in crop plants in order to modify the starch synthesized in the plants (for example WO 92/11376, WO 92/14827, WO 91/19806),
- transgenic crop plants which are resistant to certain herbicides of the glufosinate-(cf, for example, EP-A 0 242 236, EP-A 0 242 246) or glyphosate-type (WO 92/00377), or of the sulfonylurea-type (EP-A 0 257 993, U.S. Pat. No. 5,013,659A),
- transgenic crop plants, for example cotton, having the ability to produce *Bacillus thuringiensis* toxins (Bt toxins) which impart resistance to certain pests to the plants (EP-A 0 142 924, EP-A 0 193 259),
- transgenic crop plants having a modified fatty acid composition (WO 91/13972).

Numerous molecular biological techniques which allow the preparation of novel transgenic plants having modified properties are known in principle; see, for example, Sambrook et al., 1989, Molecular Cloning, A Laboratory Manual, 2nd ed. Cold Spring Harbor Laboratory Press, Cold Spring Harbor, N.Y.; or Winnacker "Gene und Klone" [Genes and Clones], VCH Weinheim, 2nd edition 1996, or Christou, "Trends in Plant Science" 1 (1996) 423-431). In order to carry out such genetic engineering manipulations, it is possible to introduce nucleic acid molecules into plasmids which allow a mutagenesis or a change in the sequence to occur by recombination of DNA sequences. Using the abovementioned standard processes it is possible, for example, to exchange bases, to remove partial sequences or to add natural or synthetic sequences. To link the DNA fragments with each other, it is possible to attach adaptors or linkers to the fragments.

Plant cells having a reduced activity of a gene product can be prepared, for example, by expressing at least one appropriate antisense-RNA, a sense-RNA to achieve a cosuppression effect, or by expressing at least one appropriately constructed ribozyme which specifically cleaves transcripts of the above-mentioned gene product.

To this end it is possible to employ both DNA molecules which comprise the entire coding sequence of a gene product including any flanking sequences that may be present, and DNA molecules which comprise only parts of the coding sequence, it being necessary for these parts to be long enough to cause an antisense effect in the cells. It is also possible to use DNA sequences which have a high degree of homology to the coding sequences of a gene product but which are not entirely identical.

When expressing nucleic acid molecules in plants, the synthesized protein can be localized in any desired compartment of the plant cells. However, to achieve localization in a certain compartment, it is, for example, possible to link the coding region with DNA sequences which ensure localization in a certain compartment. Such sequences are known to the person skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated to whole plants using known techniques. The transgenic plants can in principle be plants of any desired plant species, i.e. both monocotyledonous and dicotyledonous plants. In this manner, it is possible to obtain transgenic plants which have modified properties by overexpression, suppression or inhibition of homologous (=natural) genes or gene sequences or by expression of heterologous (=foreign) genes or gene sequences.

When using the active compounds according to the invention in transgenic crops, in addition to the effects against harmful plants which can be observed in other crops, there are frequently effects which are specific for the application in the respective transgenic crop, for example a modified or specifically broadened spectrum of weeds which can be controlled, modified application rates which can be used for the application, preferably good combinability with the herbicides to which the transgenic crops are resistant, and an effect on the growth and the yield of the transgenic crop plants. The invention therefore also provides for the use of the compounds according to the invention as herbicides for controlling harmful plants in transgenic crop plants.

In addition, the substances according to the invention have outstanding growth-regulating properties in crop plants. They engage in the plant metabolism in a regulating manner and can this be employed for the targeted control of plant constituents and for facilitating harvesting, for example by provoking desiccation and stunted growth. Furthermore, they are also suitable for generally regulating and inhibiting undesirable vegetative growth, without destroying the plants in the process. Inhibition of vegetative growth plays an important role in many monocotyledon and dicotyledon crops because lodging can be reduced hereby, or prevented completely.

The compounds according to the invention can be applied in the customary formulations in the form of wettable powders, emulsifiable concentrates, sprayable solutions, dusts or granules. The invention therefore also provides herbicidal compositions comprising compounds of the formula I. The compounds of the formula I can be formulated in various ways depending on the prevailing biological and/or chemico-physical parameters. Examples of suitable formulation options are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil dispersions (OD), oil- or water-based dispersions, oil-miscible solutions, dusts (DP), capsule suspensions (CS), seed-dressing compositions, granules for broadcasting and soil application, granules (GR) in the form of microgranules, spray granules, coating granules and adsorption granules, water-dispersible granules (WG), water-soluble granules (SG), ULV formulations, microcapsules and waxes. These individual formulation types are known in principle and are described, for example, in Winnacker-Küchler, "Chemische Technologie" [Chemical Technology], Volume 7, C. Hauser Verlag Munich, 4th. Edition 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation auxiliaries, such as inert materials, surfactants, solvents and other additives, are likewise known and are described, for example, in Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schonfeldt, "Grenzflüchenaktive Äthylenoxidaddkte" [Surface-active ethylene oxide adducts], Wiss. Verlagagesell. Stuttgart 1976; Winnacker-Küchler, "Chemische Technologie" [Chemical Technology], Volume 7, C. Hauser Verlag Munich, 4th Edition 1986.

Wettable powders are preparations which are uniformly dispersible in water and which contain, in addition to the active compound and as well as a diluent or inert substance, surfactants of ionic and/or nonionic type (wetting agents, dispersants), for example polyethoxylated alkyl phenols, polyethoxylated fatty alcohols, polyethoxylated fatty amines, fatty alcohol polyglycol ethersulfates, alkanesulfonates, alkylbenzenesulfonates, sodium ligninsulfonate, sodium 2,2'-dinaphthylmethane-6,6'-disulfonate, sodium dibutyinaphthalenesulfona-te or else sodium oleoylmethyltaurinate. To prepare the wettable powders, the herbicidally active compounds are finely ground, for example in customary apparatus such as hammer mills, fan mills and air-jet mills, and are mixed simultaneously or subsequently with the formulation auxiliaries.

Emulsifiable concentrates are prepared by dissolving the active compound in an organic solvent, for example butanol, cyclohexanone, dimethylformamide, xylene or else relatively high-boiling aromatic compounds or hydrocarbons or mixtures of the solvents, with the addition of one or more surfactants of ionic and/or nonionic type (emulsifiers). Examples of emulsifiers which can be used are calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters or polyoxyethylene sorbitan esters, for example polyoxyethylene sorbitan fatty acid esters.

Dusts are obtained by grinding the active compound with finely divided solid substances, for example talc, natural clays, such as kaolin, bentonite and pyrophyllite, or diatomaceous earth. Suspension concentrates can be water- or oil-based. They can be prepared, for example, by wet milling using commercially customary bead mills, with or without the addition of surfactants as already mentioned above, for example, in the case of the other formulation types.

Emulsions, for example oil-in-water emulsions (EW), can be prepared for example by means of stirrers, colloid mills and/or static mixers using aqueous organic solvents and, if desired, surfactants as already mentioned above, for example, in the case of the other formulation types.

Granules can be prepared either by spraying the active compound onto adsorptive, granulated inert material or by applying active-compound concentrates to the surface of carriers such as sand, kaolinites or granulated inert material, by means of adhesive binders, for example polyvinyl alcohol, sodium polyacrylate or else mineral oils. Suitable active compounds can also be granulated in the manner which is customary for the preparation of fertilizer granules, if desired as a mixture with fertilizers. Water-dispersible granules are generally prepared by the customary processes, such as spray-drying, fluidized-bed granulation, disk granulation, mixing using high-speed mixers, and extrusion without solid inert material.

For the preparation of disk, fluidized-bed, extruder and spray granules, see for example processes in "Spray-Drying Handbook" 3rd ed. 1979, G. Goodwin Ltd., London; J. E. Browning, "Agglomeration", Chemical and Engineering 1967, pages 147 ff.; "Perry's Chemical Engineer's Handbook", 5th Ed., McGraw-Hill, New York 1973, pp. 8-57. For further details on the formulation of crop protection products, see for example G. C. Klingman, "Weed Control as a Science", John Wiley and Sons Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations generally contain from 0.1 to 99% by weight, in particular from 0.1 to 95% by weight, of active compound of the formula I. In wettable powders the concentration of active compound is, for example, from about 10 to 99% by weight, the remainder to 100% by weight consisting of customary formulation constituents. In emulsifiable concentrates the concentration of active compound can be from about 1 to 90%, preferably from 5 to 80%, by weight. Formulations in the form of dusts contain from 1 to 30% by weight of active compound, preferably most commonly from 5 to 20% by weight of active compound, while sprayable solutions contain from about 0.05 to 80%, preferably from 2 to 50%, by weight of active compound. In the case of water-dispersible granules the content of active compound depends partly on whether the active compound is in liquid or solid form and on the granulation auxiliaries, fillers, etc. that are used. In water-dispersible granules the content of active compound, for example, is between 1 and 95% by weight, preferably between 10 and 80% by weight.

In addition, the formulations of active compound may comprise the tackifiers, wetting agents, dispersants, emulsifiers, penetrants, preservatives, antifreeze agents, solvents, fillers, carriers, colorants, antifoams, evaporation inhibitors and pH and viscosity regulators which are customary in each case.

Based on these formulations it is also possible to produce combinations with other pesticidally active substances, for example insecticides, acaricides, herbicides and fungicides, and also with safeners, fertilizers and/or growth regulators, for example in the form of a ready-mix or tank mix.

Suitable active compounds which can be combined with the active compounds according to the invention in mixed formulations or in a tank mix are, for example, known active compounds as described in for example World Herbicide New Product Technology Handbook, China Agricultural Science and Farming Techniques Press, 2010.9 and in the literature cited therein. For example the following active compounds may be mentioned as herbicides which can be combined with the compounds of the formula I (note: the compounds are either named by the "common name" in accordance with the International Organization for Standardization (ISO) or by the chemical names, if appropriate together with a customary code number): acetochlor, butachlor, alachlor, propisochlor, metolachlor, s-metolachlor, pretilachlor, propachlor, ethachlor, napropamide, R-left handed napropamide, propanil, mefenacet, diphenamid, diflufenican, ethaprochlor, beflubutamid, bromobutide, dimethenamid, dimethenamid-P, etobenzanid, flufenacet, thenylchlor, metazachlor, isoxaben, flamprop-M-methyl, flamprop-M-propyl, allidochlor, pethoxamid, chloranocryl, cyprazine, mefluidide, monalide, delachlor, prynachlor, terbuchlor, xylachlor, dimethachlor, cisanilide, trimexachlor, clomeprop, propyzamide, pentanochlor, carbetamide, benzoylprop-ethyl, cyprazole, butenachlor, tebutam, benzipram, quinonamid, dichlofluanid, naproanilide, diethatyl-ethyl, naptalam, TO 2, EL-177, benzadox, chlorthiamid, chlorophthalimide, isocarbamide, picolinafen, atrazine, simazine, prometryn, cyanatryn, simetryn, ametryn, propazine, dipropetryn, SSH-108, terbutryn, terbuthylazine, triaziflam, cyprazine, proglinazine, trietazine, prometon, simetone, aziprotryne, desmetryn, dimethametryn, procyazine, mesoprazine, sebuthylazine, secbumeton, terbumeton, methoprotryne, cyanatryn, ipazine, chlorazine, atraton, pendimethalin, eglinazine, cyanuric acid, indaziflam, chlorsulfuron, metsulfuron-methyl, bensulfuron methyl, chlorimuron-ethyl, tribenuron-methyl, thifensulfuron-methyl, pyrazosulfuron-ethyl, mesosulfuron, iodosulfuron-methyl sodium, foramsulfuron, cinosulfuron, triasulfuron, sulfometuron methyl, nicosulfuron, ethametsulfuron-methyl, amidosulfuron, ethoxysulfuron, cyclosulfamuron, rimsulfuron, azimsulfuron, flazasulfuron, monosulfuron, monosulfuron-ester, flucarbazone-sodium, flupyrsulfuron-methyl, halosulfuron-methyl, oxasulfuron, imazosulfuron, primisulfuron, propoxycarbazone, prosulfuron, sulfosulfuron, trifloxysulfuron, triflusulfuron-methyl, tritosulfuron, sodium metsulfuron methyl, flucetosulfuron, HNPC-C, orthosulfamuron, propyrisulfuron, metazosulfuron, acifluorfen, fomesafen, lactofen, fluoroglycofen, oxyfluorfen, chlornitrofen, aclonifen, ethoxyfen-ethyl, bifenox, nitrofluorfen, chlomethoxyfen, fluorodifen, fluoronitrofen, furyloxyfen, nitrofen, TOPE, DMNP, PPG1013, AKH-7088, halosafen, chlortoluron, isoproturon, linuron, diuron, dymron, fluometuron, benzthiazuron, methabenzthiazuron, cumyluron, ethidimuron, isouron, tebuthiuron, buturon, chlorbromuron, methyldymron, phenobenzuron, SK-85, metobromuron, metoxuron, afesin, monuron, siduron, fenuron, fluothiuron, neburon, chloroxuron, noruron, isonoruron, 3-cyclooctyl-1, thiazfluron, tebuthiuron, difenoxuron, parafluron, methylamine tribunil, karbutilate, trimeturon, dimefuron, monisouron, anisuron, methiuron, chloreturon, tetrafluron, phenmedipham, phenmedipham-ethyl, desmedipham, asulam, terbucarb, barban, propham, chlorpropham, dichlomate, swep, chlorbufam, carboxazole, chlorprocarb, fenasulam, BCPC, CPPC, carbasulam, butylate, benthiocarb, vernolate, molinate, triallate, dimepiperate, esprocarb, pyributicarb, cycloate, avadex, EPTC, ethiolate, orbencarb, pebulate, prosulfocarb, tiocarbazil, CDEC, dimexano, isopolinate, methiobencarb, 2,4-D butyl ester, MCPA-Na, 2,4-D isooctyl ester, MCPA isooctyl ester, 2,4-D sodium salt, 2,4-D dimethylamine salt, MCPA-thioethyl, MCPA, 2,4-D propionic acid, high 2,4-D propionic acid salt, 2,4-D butyric acid, MCPA propionic acid, MCPA propionic acid salt, MCPA butyric acid, 2,4,5-D, 2,4,5-D propionic acid, 2,4,5-D butyric acid, MCPA amine salt, dicamba, erbon, chlorfenac, disul, TBA, chloramben, methoxy-TBA, diclofop-methyl, fluazifop-butyl, fluazifop-p-butyl, haloxyfop-methyl, haloxyfop-P, quizalofop-ethyl, quizalofop-p-ethyl, fenoxaprop-ethy, fenoxaprop-p-ethyl, propaquizafop, cyhalofop-butyl, metamifop, clodinafop-propargyl, fenthiaprop-ethyl, chloroazifop-propynyl, poppenate-methyl, trifopsime, isoxapyrifop, paraquat, diquat, oryzalin, ethalfluralin, isopropalin, nitralin, profluralin, prodinamine, benfluralin, fluchloraline, dinitramina, dipropalin, chlornidine, methalpropalin, dinoprop, glyphosate, anilofos, glufosinate ammonium, amiprophos-methyl, sulphosate, piperophos, bialaphos-sodium, bensulide, butamifos, phocarb, 2,4-DEP, H-9201, zytron, imazapyr, imazethapyr, imazaquin, imazamox, imazamox ammonium salt, imazapic, imazamethabenz-methyl, fluroxypyr, fluroxypyr isooctyl ester, clopyralid, picloram, trichlopyr, dithiopyr, haloxydine, 3,5,6-trichloro-2-pyridinol, thiazopyr, fluridone, aminopyralid, diflufenzopyr, triclopyr-butotyl, Cliodinate, sethoxydim, clethodim, cycloxydim, alloxydim, clefoxydim, butroxydim, tralkoxydim, tepraloxydim, buthidazole, metribuzin, hexazinone, metamitron, ethiozin, ametridione, amibuzin, bromoxynil, bromoxynil octanoate, ioxynil octanoate, ioxynil, dichlobenil, diphenatrile, pyraclonil, chloroxynil, iodobonil, flumetsulam, florasulam, penoxsulam, metosulam, cloransulam-methyl, diclosulam, pyroxsulam, benzofluor, bispyribac-sodium, pyribenzoxim, pyriftalid, pyriminobac-methyl, pyrithiobac-sodium, benzobicylon, mesotrione, sulcotrione, tembotrione, tefuryltrione, bicyclopyrone, ketodpiradox, isoxaflutole, isoxachlortole, fenoxasulfone, methiozolin, fluazolate, pyraflufen-ethyl, pyrazolynate, difenzoquat, pyrazoxyfen, benzofenap, nipyraclofen, pyrasulfotole, topramezone, pyroxasulfone, cafenstrole, flupoxam, aminotriazole, amicarbazone, azafenidin, carfentrazone-ethyl, sulfentrazone, bencarbazone, benzfendizone, butafenacil, bromacil, isocil, lenacil, terbacil, flupropacil, cinidon-ethyl, flumiclorac-pentyl, flumioxazin, propyzamide, MK-129, flumezin, pentachlorophenol, dinoseb, dinoterb, dinoterb acetate, dinosam, DNOC, chloronitrophene, medinoterb acetate, dinofenate, oxadiargyl, oxadiazon, pentoxazone, profluazol, fluthiacet-methyl, fentrazamide, flufenpyr-ethyl, pyrazon, brompyrazon, metflurazon, kusakira, dimidazon, oxapyrazon, norflurazon, pyridafol, quinclorac, quinmerac, bentazone, pyridate, oxaziclomefone, benazolin, clomazone, cinmethylin, ZJ0702, pyribambenz-propyl, indanofan, sodium chlorate, dalapon, trichloroacetic acid, monochloroacetic acid, hexachloroacetone, flupropanate, cyperquat, bromofenoxim, epronaz, methazole, flurtamone, benfuresate, ethofumesate, tioclorim, chlorthal, fluorochloridone, tavron, acrolein, bentranil, tridiphane, chlorfenpropmethyl, thidiarizonaimin, phenisopham, busoxinone, methoxyphenone, saflufenacil, clacyfos, chloropon, alorac, diethamquat, etnipromid, iprymidam, ipfencarbazone, thiencarbazone-methyl, pyrimisulfan, chlorflurazole, tripropindan, sulglycapin, prosulfalin, cambendichlor, aminocyclopyrachlor, rodethanil, benoxacor, fenclorim, flurazole, fenchlorazole-ethyl, cloquintocet-mexyl, oxabetrinil, MG 191, cyometrinil, DKA-24, mefenpyr-diethyl, furilazole, fluxofenim, isoxadifen-ethyl, dichlormid, halauxifen-methyl, DOW florpyrauxifen, UBH-509, D489, LS 82-556, KPP-300, NC-324, NC-330, KH-218, DPX-N8189, SC-0744, DOWCO535, DK-8910, V-53482, PP-600, MBH-001, KIH-9201, ET-751, KIH-6127 and KIH-2023.

For use, the formulations which are present in commercially available form are, if appropriate, diluted in the customary manner, for example using water in the case of wettable powders, emulsifiable concentrates, dispersions and water-dispersible granules. Products in the form of dusts, granules for soil application or broadcasting and sprayable solutions are usually not further diluted with other inert substances prior to use. The application rate of the compounds of the formula I required varies with the external conditions, such as temperature, humidity, the nature of the herbicide used and the like. It can vary within wide limits, for example between 0.001 and 1.0 kg a.i./ha or more of active substance, but it is preferably between 0.005 and 750 g a.i./ha, especially between 0.005 and 250 g a.i./ha.

SPECIFIC MODE FOR CARRYING OUT THE INVENTION

The following embodiments are used to illustrate the present invention in detail and should not be taken as any limit to the present invention. The scope of the invention would be explained through the Claims.

In view of economics and variety of a compound, we preferably synthesized several compounds, part of which are listed in the following Table 1. The structure and information of a certain compound are shown in Table 1. The compounds in Table 1 are listed for further explication of the present invention, other than any limit therefor. The subject of the present invention should not be interpreted by those skilled in the art as being limited to the following compounds.

TABLE 1
Structures and $^1$H NMR data of compounds
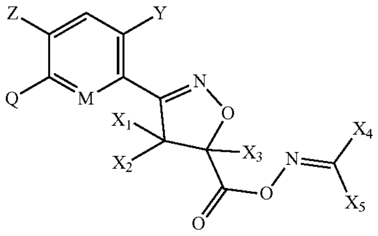
I
| NO. | Q | 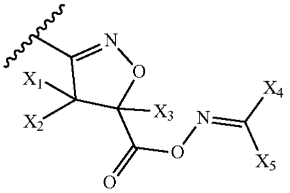 | Y | Z | M | $^1$H NMR |
|---|---|---|---|---|---|---|
| 1 | 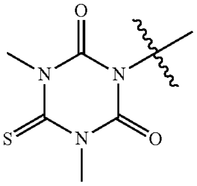 [SMILES: *n1c(=O)n(C)c(=S)n(C)c1=O] | 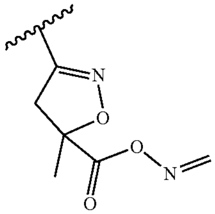 [SMILES: *C1=NOC(C)(C(=O)ON=C)C1] | Cl | F | CH | |
| 2 | 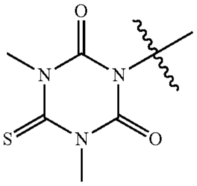 [SMILES: *n1c(=O)n(C)c(=S)n(C)c1=O] | 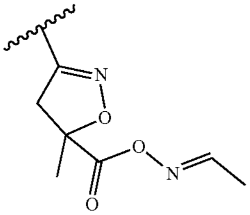 [SMILES: *C1=NOC(C)(C(=O)O/N=C/C)C1] | Cl | F | CH | $^1$H NMR (500 MHz, DMSO-$d_6$) δ 8.03-7.90 (m, 3H), 3.98 (d, J = 17.5 Hz, 1H), 3.64 (s, 6H), 3.57 (d, J = 17.5 Hz, 1H), 1.98 (d, J = 6.0 Hz, 3H), 1.70 (s, 3H). |
| 3 | 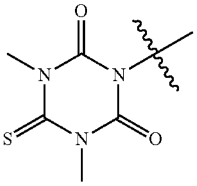 [SMILES: *n1c(=O)n(C)c(=S)n(C)c1=O] | 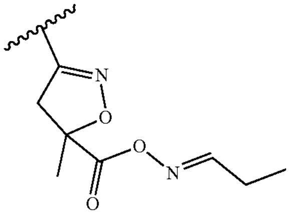 [SMILES: *C1=NOC(C)(C(=O)O/N=C/CC)C1] | Cl | F | CH | |
| 4 | 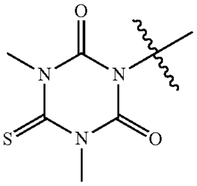 [SMILES: *n1c(=O)n(C)c(=S)n(C)c1=O] | 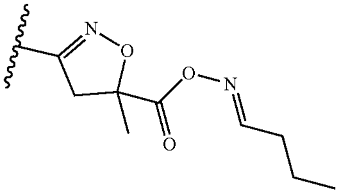 [SMILES: *C1=NOC(C)(C(=O)O/N=C/CCC)C1] | Cl | F | CH | |
| 5 | 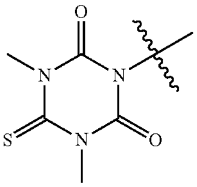 [SMILES: *n1c(=O)n(C)c(=S)n(C)c1=O] | 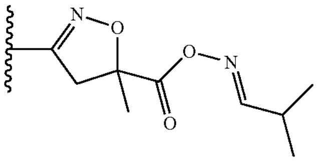 [SMILES: *C1=NOC(C)(C(=O)O/N=C/C(C)C)C1] | Cl | F | CH | |

TABLE 1-continued
Structures and $^1H$ NMR data of compounds
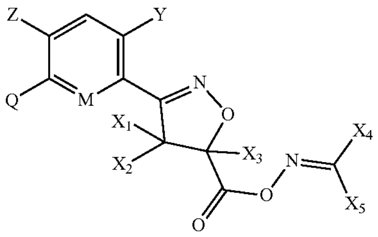
I
| NO. | Q | 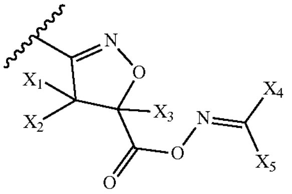 | Y | Z | M | $^1H$ NMR |
|---|---|---|---|---|---|---|
| 6 | 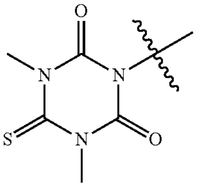 [SMILES: *n1c(=O)n(C)c(=S)n(C)c1=O] | 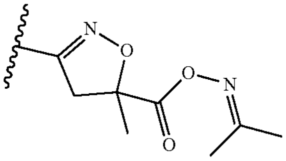 [SMILES: *C1=NOC(C)(C(=O)ON=C(C)C)C1] | $CF_3$ | F | CH | |
| 7 | 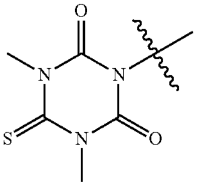 [SMILES: *n1c(=O)n(C)c(=S)n(C)c1=O] | 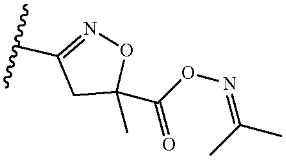 [SMILES: *C1=NOC(C)(C(=O)ON=C(C)C)C1] | Br | F | CH | |
| 8 | 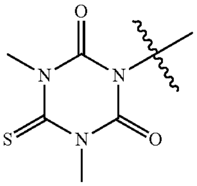 [SMILES: *n1c(=O)n(C)c(=S)n(C)c1=O] | 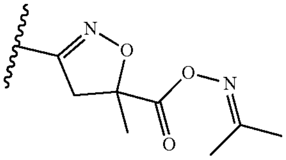 [SMILES: *C1=NOC(C)(C(=O)ON=C(C)C)C1] | Cl | H | CH | |
| 9 | 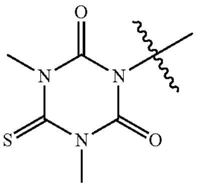 [SMILES: *n1c(=O)n(C)c(=S)n(C)c1=O] | 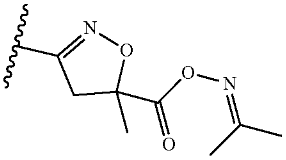 [SMILES: *C1=NOC(C)(C(=O)ON=C(C)C)C1] | Cl | Cl | CH | |
| 10 | 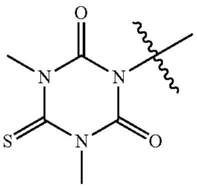 [SMILES: *n1c(=O)n(C)c(=S)n(C)c1=O] | 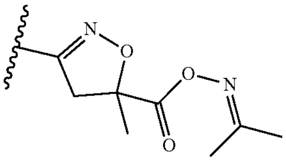 [SMILES: *C1=NOC(C)(C(=O)ON=C(C)C)C1] | Cl | F | CH | $^1H$ NMR (500 MHz, DMSO-d6) δ 7.95 (d, J = 7.5 Hz, 1H), 7.90 (d, J = 9.5 Hz, 1H), 3.96 (d, J = 17.5 Hz, 1H), 3.63 (s, 6H), 3.59 (d, J = 17.5 Hz, 1H), 1.98 (s, 3H), 1.96 (s, 3H), 1.62 (s, 3H) |

TABLE 1-continued
Structures and $^1$H NMR data of compounds
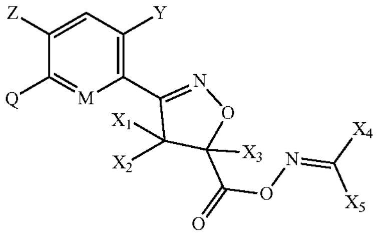
I
| NO. | Q | 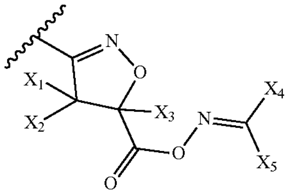 | Y | Z | M | $^1$H NMR |
|---|---|---|---|---|---|---|
| 11 | 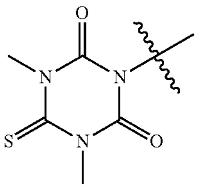 [SMILES: *n1c(=O)n(C)c(=S)n(C)c1=O] | 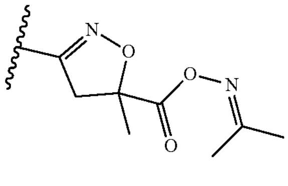 [SMILES: *C1=NOC(C)(C(=O)ON=C(C)C)C1] | Cl | OH | CH | |
| 12 | 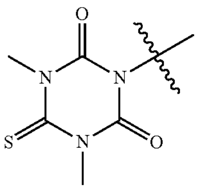 [SMILES: *n1c(=O)n(C)c(=S)n(C)c1=O] | 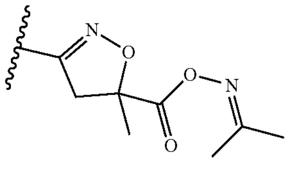 [SMILES: *C1=NOC(C)(C(=O)ON=C(C)C)C1] | CN | H | CH | |
| 13 | 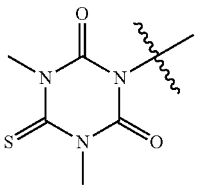 [SMILES: *n1c(=O)n(C)c(=S)n(C)c1=O] | 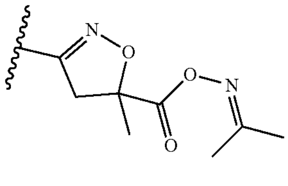 [SMILES: *C1=NOC(C)(C(=O)ON=C(C)C)C1] | CN | F | CH | |
| 14 | 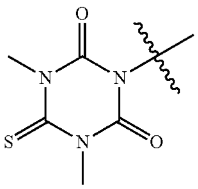 [SMILES: *n1c(=O)n(C)c(=S)n(C)c1=O] | 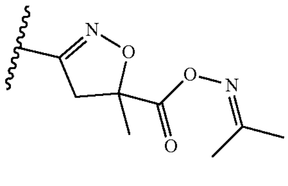 [SMILES: *C1=NOC(C)(C(=O)ON=C(C)C)C1] | $NO_2$ | F | CH | |
| 15 | 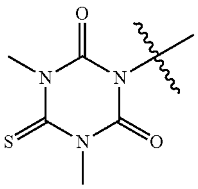 [SMILES: *n1c(=O)n(C)c(=S)n(C)c1=O] | 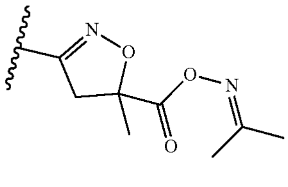 [SMILES: *C1=NOC(C)(C(=O)ON=C(C)C)C1] | $NH_2$ | F | CH | |

TABLE 1-continued
Structures and $^{1}H$ NMR data of compounds
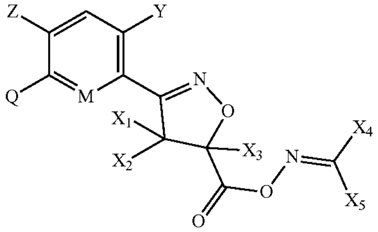
I
| NO. | Q | 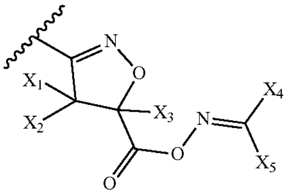 | Y | Z | M | $^{1}H$ NMR |
|---|---|---|---|---|---|---|
| 16 | 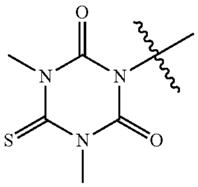 [SMILES: *n1c(=O)n(C)c(=S)n(C)c1=O] | 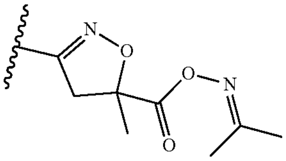 [SMILES: *C1=NOC(C)(C(=O)ON=C(C)C)C1] | Cl | F | N | $^{1}H$ NMR (500 MHz, Chloroform-d) δ 7.61 (d, J = 8.0 Hz, 1H), 3.81 (s, 6H), 3.41 (d, J = 18.0 Hz, 1H), 2.87 (d, J = 18.0 Hz, 1H), 2.64 (s, 6H), 1.54 (s, 3H). |
| 17 | 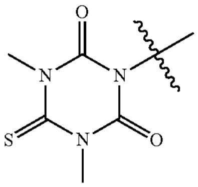 [SMILES: *n1c(=O)n(C)c(=S)n(C)c1=O] | 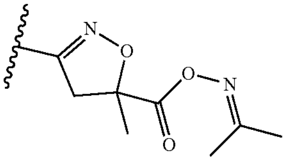 [SMILES: *C1=NOC(C)(C(=O)ON=C(C)C)C1] | Cl | H | N | |
| 18 | 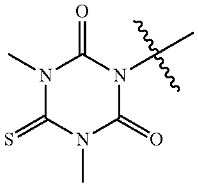 [SMILES: *n1c(=O)n(C)c(=S)n(C)c1=O] | 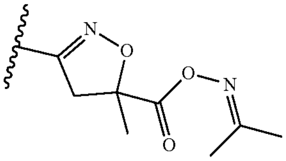 [SMILES: *C1=NOC(C)(C(=O)ON=C(C)C)C1] | CN | H | N | |
| 19 | 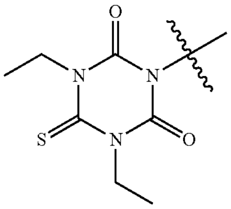 [SMILES: *n1c(=O)n(CC)c(=S)n(CC)c1=O] | 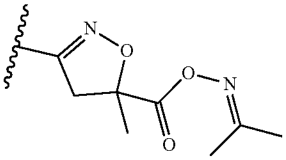 [SMILES: *C1=NOC(C)(C(=O)ON=C(C)C)C1] | Cl | F | CH | |
| 20 | 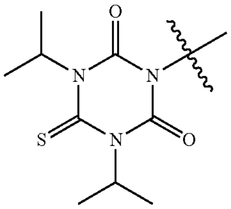 [SMILES: *n1c(=O)n(C(C)C)c(=S)n(C(C)C)c1=O] | 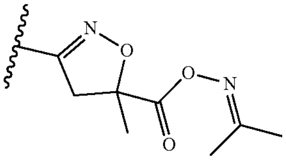 [SMILES: *C1=NOC(C)(C(=O)ON=C(C)C)C1] | Cl | F | CH | |

TABLE 1-continued
Structures and $^1$H NMR data of compounds
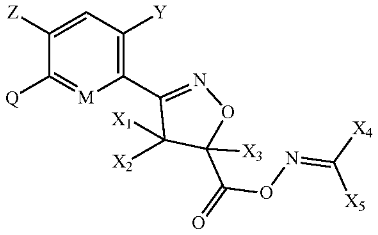
I
| NO. | Q | 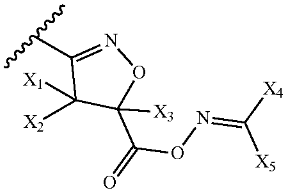 | Y | Z | M | $^1$H NMR |
|---|---|---|---|---|---|---|
| 21 | 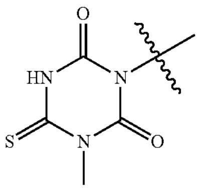 [SMILES: *n1c(=O)[nH]c(=S)n(C)c1=O] | 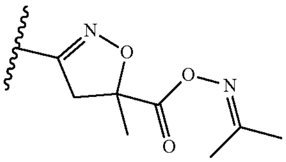 [SMILES: *C1=NOC(C)(C(=O)ON=C(C)C)C1] | Cl | F | CH | |
| 22 | 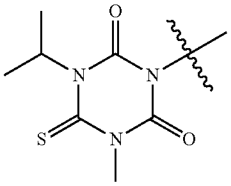 [SMILES: *n1c(=O)n(C)c(=S)n(C(C)C)c1=O] | 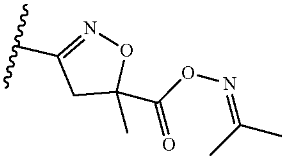 [SMILES: *C1=NOC(C)(C(=O)ON=C(C)C)C1] | Cl | F | CH | |
| 23 | 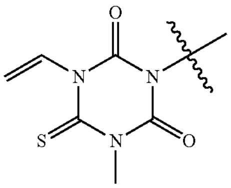 [SMILES: *n1c(=O)n(C)c(=S)n(C=C)c1=O] | 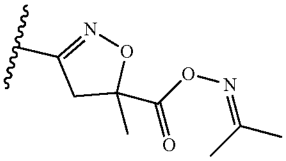 [SMILES: *C1=NOC(C)(C(=O)ON=C(C)C)C1] | Cl | F | CH | |
| 24 | 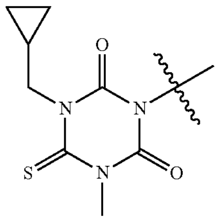 [SMILES: *n1c(=O)n(C)c(=S)n(CC2CC2)c1=O] | 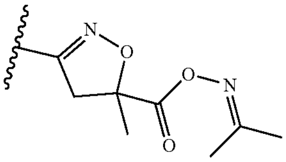 [SMILES: *C1=NOC(C)(C(=O)ON=C(C)C)C1] | Cl | F | CH | |
| 25 | 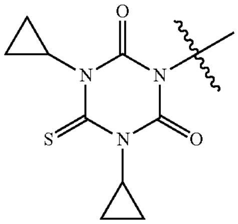 [SMILES: *n1c(=O)n(C2CC2)c(=S)n(C2CC2)c1=O] | 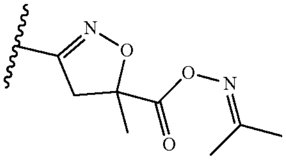 [SMILES: *C1=NOC(C)(C(=O)ON=C(C)C)C1] | Cl | F | CH | |

TABLE 1-continued
Structures and $^1$H NMR data of compounds
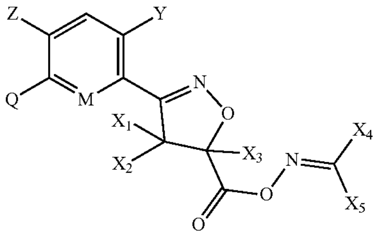
I
| NO. | Q | 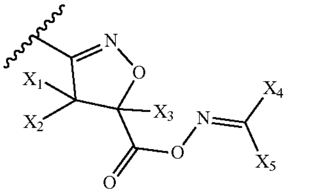 | Y | Z | M | $^1$H NMR |
|---|---|---|---|---|---|---|
| 26 | 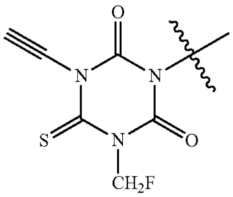 | 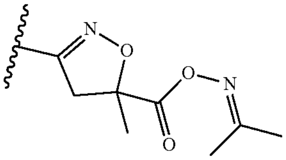 [SMILES: *C1=NOC(C)(C(=O)ON=C(C)C)C1] | Cl | F | CH | |
| 27 | 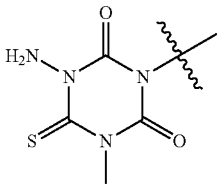 [SMILES: *n1c(=O)n(C)c(=S)n(N)c1=O] | 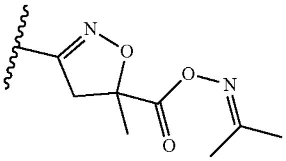 [SMILES: *C1=NOC(C)(C(=O)ON=C(C)C)C1] | Cl | F | CH | |
| 28 | 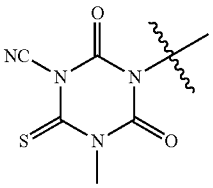 [SMILES: *n1c(=O)n(C)c(=S)n(C#N)c1=O] | 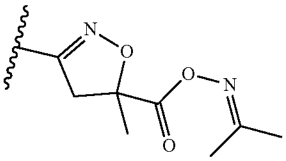 [SMILES: *C1=NOC(C)(C(=O)ON=C(C)C)C1] | Cl | F | CH | |
| 29 | 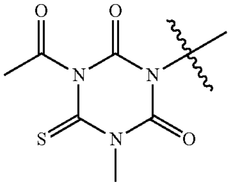 [SMILES: *n1c(=O)n(C)c(=S)n(C(C)=O)c1=O] | 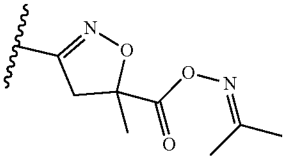 [SMILES: *C1=NOC(C)(C(=O)ON=C(C)C)C1] | Cl | F | CH | |
| 30 | 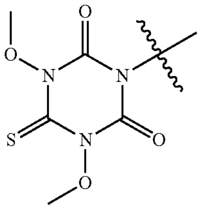 [SMILES: *n1c(=O)n(OC)c(=S)n(OC)c1=O] | 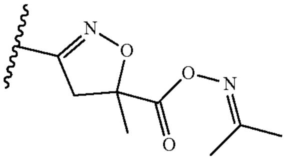 [SMILES: *C1=NOC(C)(C(=O)ON=C(C)C)C1] | Cl | F | CH | |

TABLE 1-continued
Structures and $^1$H NMR data of compounds
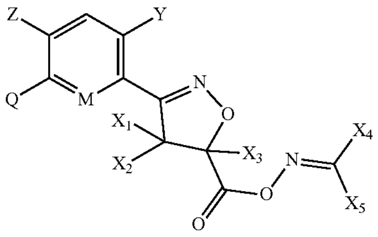
I
| NO. | Q | 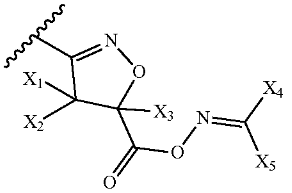 | Y | Z | M | $^1$H NMR |
|---|---|---|---|---|---|---|
| 31 | 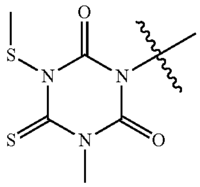 [SMILES: *n1c(=O)n(C)c(=S)n(SC)c1=O] | 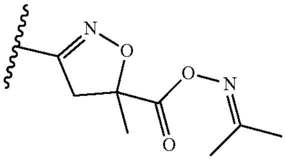 [SMILES: *C1=NOC(C)(C(=O)ON=C(C)C)C1] | Cl | F | CH | |
| 32 | 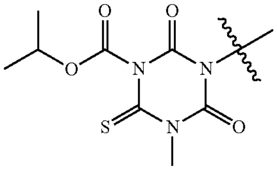 [SMILES: *n1c(=O)n(C)c(=S)n(C(=O)OC(C)C)c1=O] | 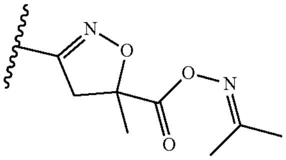 [SMILES: *C1=NOC(C)(C(=O)ON=C(C)C)C1] | Cl | F | CH | |
| 33 | 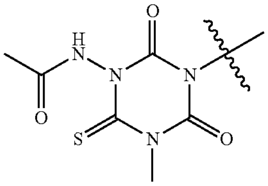 [SMILES: *n1c(=O)n(C)c(=S)n(NC(C)=O)c1=O] | 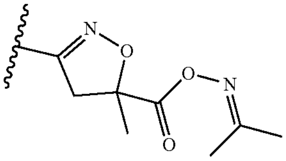 [SMILES: *C1=NOC(C)(C(=O)ON=C(C)C)C1] | Cl | F | CH | |
| 34 | 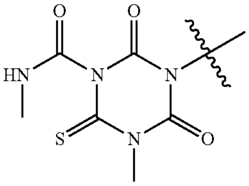 [SMILES: *n1c(=O)n(C)c(=S)n(C(=O)NC)c1=O] | 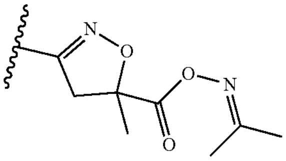 [SMILES: *C1=NOC(C)(C(=O)ON=C(C)C)C1] | Cl | F | CH | |
| 35 | 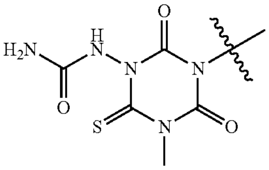 [SMILES: *n1c(=O)n(C)c(=S)n(NC(N)=O)c1=O] | 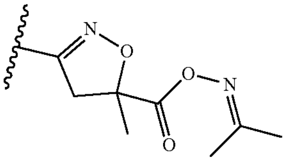 [SMILES: *C1=NOC(C)(C(=O)ON=C(C)C)C1] | Cl | F | CH | |
| 36 | 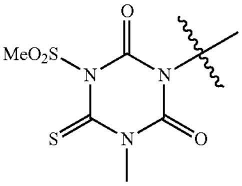 [SMILES: *n1c(=O)n(C)c(=S)n(S(C)(=O)=O)c1=O] | 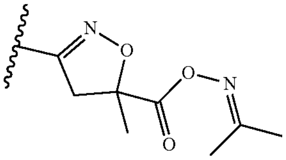 [SMILES: *C1=NOC(C)(C(=O)ON=C(C)C)C1] | Cl | F | CH | |

TABLE 1-continued
Structures and $^1$H NMR data of compounds
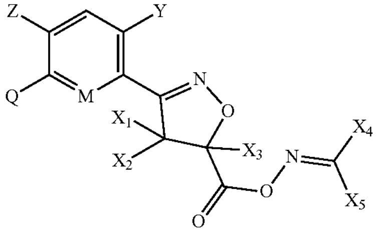
I
| NO. | Q | 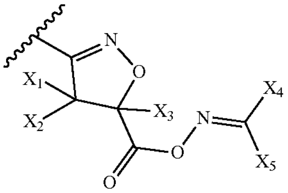 | Y | Z | M | $^1$H NMR |
|---|---|---|---|---|---|---|
| 37 | 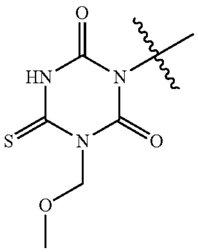 [SMILES: *n1c(=O)[nH]c(=S)n(COC)c1=O] | 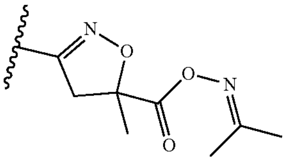 [SMILES: *C1=NOC(C)(C(=O)ON=C(C)C)C1] | Cl | F | CH | |
| 38 | 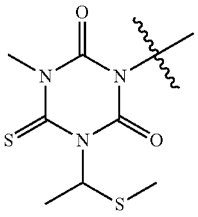 [SMILES: *n1c(=O)n(C)c(=S)n(C(C)SC)c1=O] | 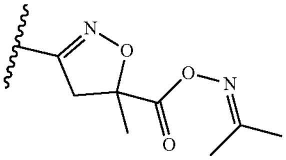 [SMILES: *C1=NOC(C)(C(=O)ON=C(C)C)C1] | Cl | F | CH | |
| 39 | 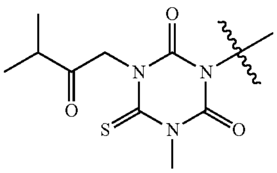 [SMILES: *n1c(=O)n(C)c(=S)n(CC(=O)C(C)C)c1=O] | 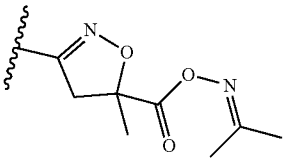 [SMILES: *C1=NOC(C)(C(=O)ON=C(C)C)C1] | Cl | F | CH | |
| 40 | 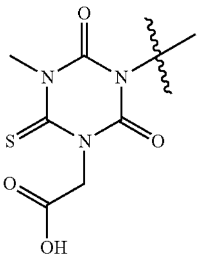 [SMILES: *n1c(=O)n(C)c(=S)n(CC(=O)O)c1=O] | 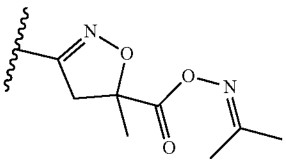 [SMILES: *C1=NOC(C)(C(=O)ON=C(C)C)C1] | Cl | F | CH | |

TABLE 1-continued
Structures and $^1$H NMR data of compounds
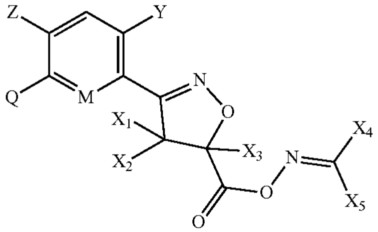
I
| NO. | Q | 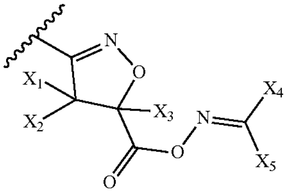 | Y | Z | M | $^1$H NMR |
|---|---|---|---|---|---|---|
| 41 | 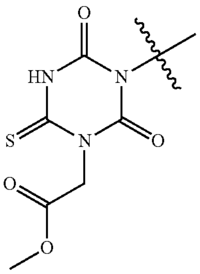 [SMILES: *n1c(=O)[nH]c(=S)n(CC(=O)OC)c1=O] | 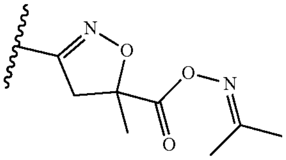 [SMILES: *C1=NOC(C)(C(=O)ON=C(C)C)C1] | Cl | F | CH | |
| 42 | 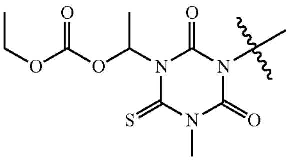 [SMILES: *n1c(=O)n(C)c(=S)n(C(C)OC(=O)OCC)c1=O] | 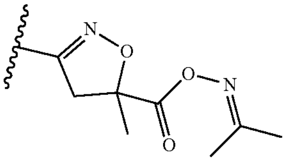 [SMILES: *C1=NOC(C)(C(=O)ON=C(C)C)C1] | Cl | F | CH | |
| 43 | 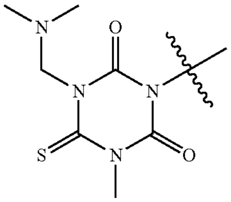 [SMILES: *n1c(=O)n(C)c(=S)n(CN(C)C)c1=O] | 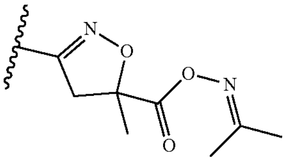 [SMILES: *C1=NOC(C)(C(=O)ON=C(C)C)C1] | Cl | F | CH | |
| 44 | 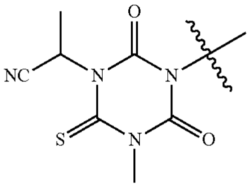 [SMILES: *n1c(=O)n(C)c(=S)n(C(C)C#N)c1=O] | 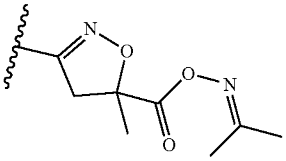 [SMILES: *C1=NOC(C)(C(=O)ON=C(C)C)C1] | Cl | F | CH | |
| 45 | 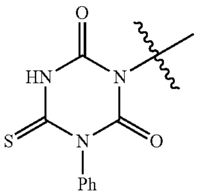 [SMILES: *n1c(=O)[nH]c(=S)n(-c2ccccc2)c1=O] | 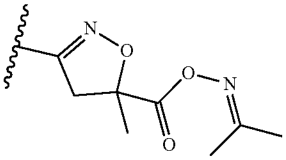 [SMILES: *C1=NOC(C)(C(=O)ON=C(C)C)C1] | Cl | F | CH | |

TABLE 1-continued
Structures and $^{1}H$ NMR data of compounds
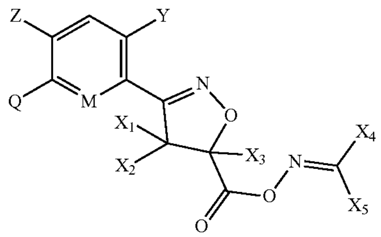
I
| NO. | Q | 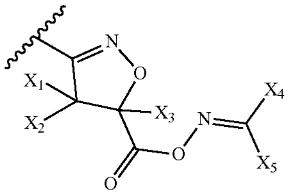 | Y | Z | M | $^{1}H$ NMR |
|---|---|---|---|---|---|---|
| 46 | 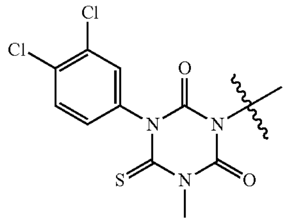 [SMILES: *n1c(=O)n(C)c(=S)n(-c2ccc(Cl)c(Cl)c2)c1=O] | 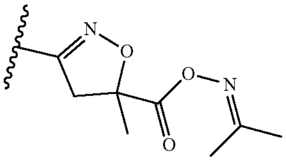 [SMILES: *C1=NOC(C)(C(=O)ON=C(C)C)C1] | Cl | F | CH | |
| 47 | 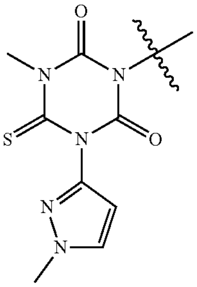 [SMILES: *n1c(=O)n(C)c(=S)n(-c2ccn(C)n2)c1=O] | 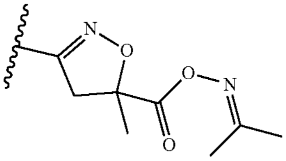 [SMILES: *C1=NOC(C)(C(=O)ON=C(C)C)C1] | Cl | F | CH | |
| 48 | 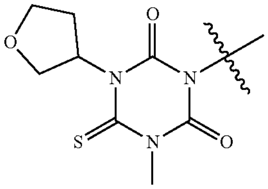 [SMILES: *n1c(=O)n(C)c(=S)n(C2CCOC2)c1=O] | 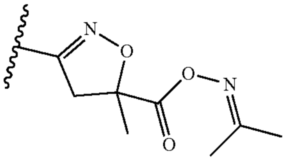 [SMILES: *C1=NOC(C)(C(=O)ON=C(C)C)C1] | Cl | F | CH | |
| 49 | 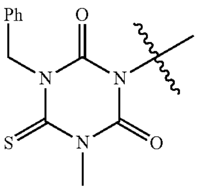 [SMILES: *n1c(=O)n(C)c(=S)n(Cc2ccccc2)c1=O] | 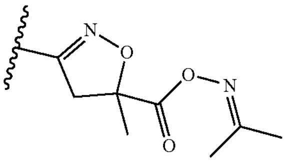 [SMILES: *C1=NOC(C)(C(=O)ON=C(C)C)C1] | Cl | F | CH | |
| 50 | 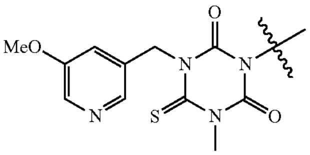 [SMILES: *n1c(=O)n(C)c(=S)n(Cc2cncc(OC)c2)c1=O] | 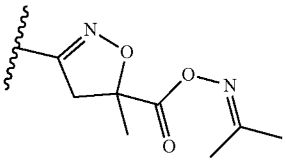 [SMILES: *C1=NOC(C)(C(=O)ON=C(C)C)C1] | Cl | F | CH | |

TABLE 1-continued
Structures and $^1$H NMR data of compounds
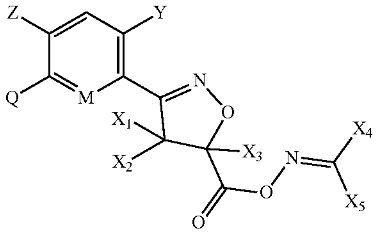
I
| NO. | Q | 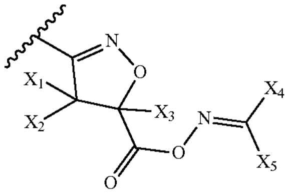 | Y | Z | M | $^1$H NMR |
|---|---|---|---|---|---|---|
| 51 | 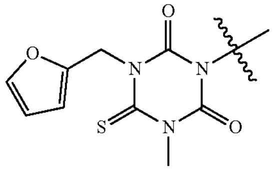 [SMILES: *n1c(=O)n(C)c(=S)n(Cc2ccco2)c1=O] | 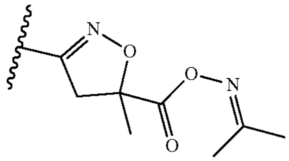 [SMILES: *C1=NOC(C)(C(=O)ON=C(C)C)C1] | Cl | F | CH | |
| 52 | 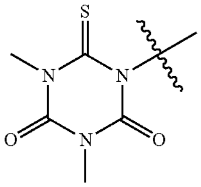 [SMILES: *n1c(=O)n(C)c(=O)n(C)c1=S] | 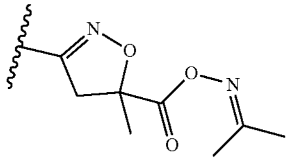 [SMILES: *C1=NOC(C)(C(=O)ON=C(C)C)C1] | Cl | F | CH | |
| 53 | 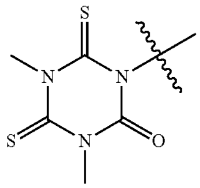 [SMILES: *n1c(=O)n(C)c(=S)n(C)c1=S] | 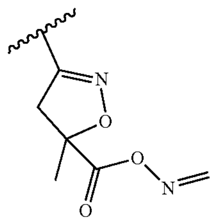 [SMILES: *C1=NOC(C)(C(=O)ON=C)C1] | Cl | F | CH | |
| 54 | 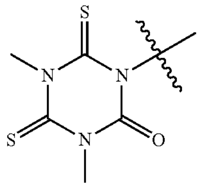 [SMILES: *n1c(=O)n(C)c(=S)n(C)c1=S] | 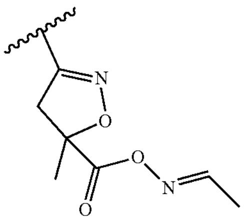 [SMILES: *C1=NOC(C)(C(=O)O/N=C/C)C1] | Cl | F | CH | $^1$H NMR (500 MHz, DMSO-$d_6$) δ 8.01-7.98 (m, 1H), 7.97 (d, J = 7.5 Hz, 1H), 7.90 (d, J = 9.5 Hz, 1H), 4.15 (s, 3H), 4.00-3.94 (m, 1H), 3.63 (s, 3H), 3.62-3.57 (m, 1H), 1.97 (d, J = 6.0 Hz, 3H), 1.70 (s, 3H). |
| 55 | 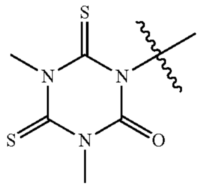 [SMILES: *n1c(=O)n(C)c(=S)n(C)c1=S] | 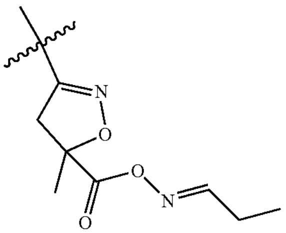 [SMILES: *C1=NOC(C)(C(=O)O/N=C/CC)C1] | Cl | F | CH | |

TABLE 1-continued
Structures and $^{1}$H NMR data of compounds
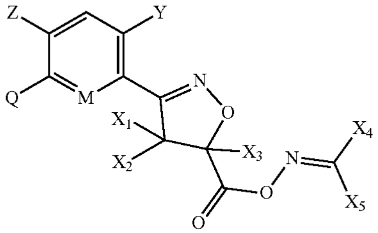
I
| NO. | Q | 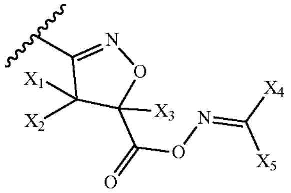 | Y | Z | M | $^{1}$H NMR |
|---|---|---|---|---|---|---|
| 56 | 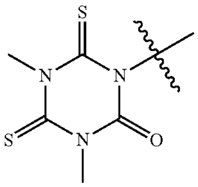 [SMILES: *n1c(=O)n(C)c(=S)n(C)c1=S] | 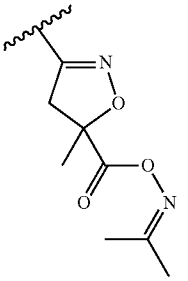 [SMILES: *C1=NOC(C)(C(=O)ON=C(C)C)C1] | Cl | F | CH | $^{1}$H NMR (500 MHz, DMSO-$d_6$) δ 7.95 (d, J = 7.5 Hz, 1H), 7.90 (d, J = 9.5 Hz, 1H), 4.15 (s, 3H), 4.01-3.94 (m, 1H), 3.68 (s, 3H), 3.62-3.55 (m, 1H), 1.98 (s, 3H), 1.96 (s, 3H), 1.62 (d, J = 5.5 Hz, 3H) |
| 57 | 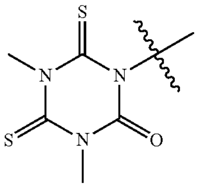 [SMILES: *n1c(=O)n(C)c(=S)n(C)c1=S] | 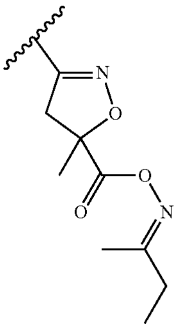 [SMILES: *C1=NOC(C)(C(=O)O/N=C(\C)CC)C1] | Cl | F | CH | $^{1}$H NMR (500 MHz, DMSO-$d_6$) δ 7.98 (d, J = 7.5 Hz, 1H), 7.90 (d, J = 9.5 Hz, 1H), 4.15 (s, 3H), 4.01-3.93 (m, 1H), 3.63 (s, 3H), 3.62-3.57 (m, 1H), 2.39-2.32 (m, 2H), 1.96 (s, 3H), 1.72 (s, 3H), 1.11-1.00 (m, 3H). |
| 58 | 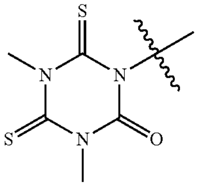 [SMILES: *n1c(=O)n(C)c(=S)n(C)c1=S] | 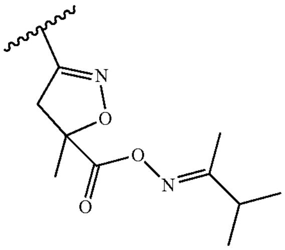 [SMILES: *C1=NOC(C)(C(=O)O/N=C(\C)C(C)C)C1] | Cl | F | CH | $^{1}$H NMR (500 MHz, DMSO-$d_6$) δ 7.97 (d, J = 7.5 Hz, 1H), 7.90 (d, J = 9.5 Hz, 1H), 4.15 (s, 3H), 3.97 (dd, J = 17.5 Hz, 1H), 3.64 (s, 3H), 3.60 (dd, J = 17.5 Hz, 1H), 2.64 (p, J = 7.0 Hz, 1H), 1.92 (s, 3H), 1.71 (s, 3H), 1.11 (d, J = 7.0 Hz, 6H). |

TABLE 1-continued
Structures and $^{1}$H NMR data of compounds
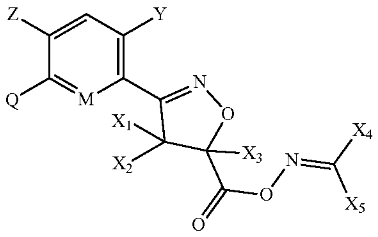
I
| NO. | Q | 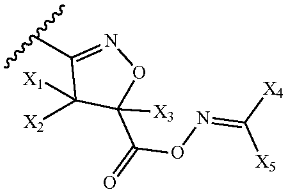 | Y | Z | M | $^{1}$H NMR |
|---|---|---|---|---|---|---|
| 59 | 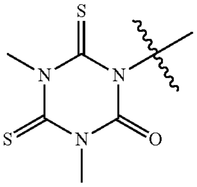 | 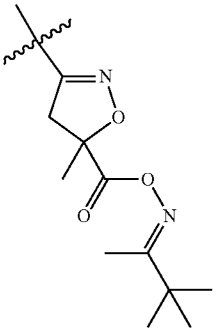 [SMILES: *C1=NOC(C)(C(=O)O/N=C(\C)C(C)(C)C)C1] | Cl | F | CH | $^{1}$H NMR (500 MHz, DMSO-d6) δ 7.97 (d, J = 7.5 Hz, 1H), 7.90 (d, J = 9.5 Hz, 1H), 3.98 (dd, J = 17.5 Hz, 1H), 4.15 (s, 3H), 3.63 (s, 3H), 3.62-3.57 (m, 1H), 1.95 (s, 3H), 1.72 (s, 3H), 1.16 (s, 9H). |
| 60 | 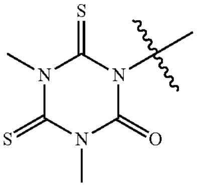 | 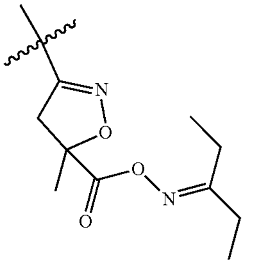 [SMILES: *C1=NOC(C)(C(=O)ON=C(CC)CC)C1] | Cl | F | CH | $^{1}$H NMR (500 MHz, DMSO) δ 7.98 (d, J = 7.5 Hz, 1H), 7.90 (d, J = 9.5 Hz, 1H), 4.15 (s, 3H), 4.01-3.92 (m, 1H), 3.63 (s, 3H), 3.62-3.57 (m, 1H), 2.40-2.32 (m, 4H), 1.71 (s, 3H), 1.09 (t, J = 7.5 Hz, 3H), 1.02 (t, J = 7.5 Hz, 3H). |
| 61 | 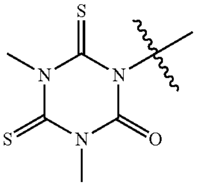 [SMILES: *n1c(=O)n(C)c(=S)n(C)c1=S] | 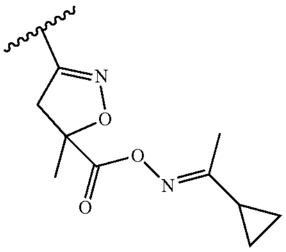 [SMILES: *C1=NOC(C)(C(=O)O/N=C(\C)C2CC2)C1] | Cl | F | CH | $^{1}$H NMR (500 MHz, DMSO-$d_6$) δ 7.96 (d, J = 7.5 Hz, 1H), 7.90 (d, J = 9.5 Hz, 1H), 4.15 (s, 3H), 3.96 (dd, J = 17.5 Hz, 1H), 3.63 (s, 3H), 3.60 (dd, J = 17.5 Hz, 1H), 1.73 (s, 3H), 1.71 (s, 3H), 0.97-0.78 (m, 5H). |
| 62 | 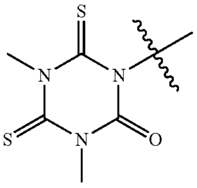 [SMILES: *n1c(=O)n(C)c(=S)n(C)c1=S] | 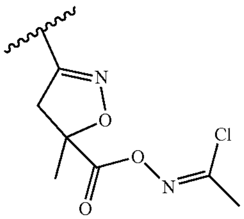 [SMILES: *C1=NOC(C)(C(=O)O/N=C(/C)Cl)C1] | Cl | F | CH | |

TABLE 1-continued
Structures and $^1$H NMR data of compounds
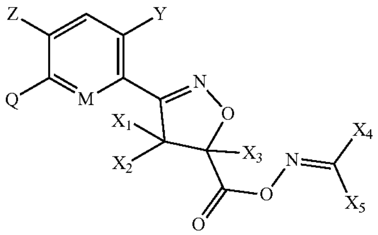
I
| NO. | Q | 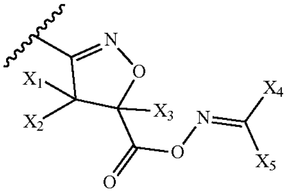 | Y | Z | M | $^1$H NMR |
|---|---|---|---|---|---|---|
| 63 | 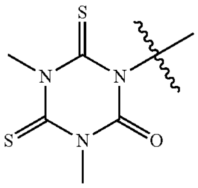 [SMILES: *n1c(=O)n(C)c(=S)n(C)c1=S] | 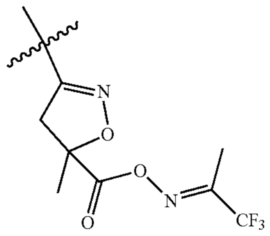 [SMILES: *C1=NOC(C)(C(=O)O/N=C(\C)C(F)(F)F)C1] | Cl | F | CH | |
| 64 | 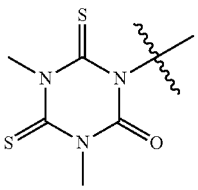 [SMILES: *n1c(=O)n(C)c(=S)n(C)c1=S] | 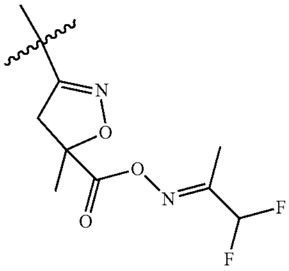 [SMILES: *C1=NOC(C)(C(=O)O/N=C(\C)C(F)F)C1] | Cl | F | CH | |
| 65 | 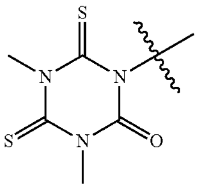 [SMILES: *n1c(=O)n(C)c(=S)n(C)c1=S] | 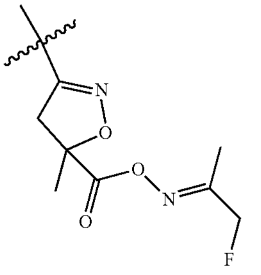 [SMILES: *C1=NOC(C)(C(=O)O/N=C(\C)CF)C1] | Cl | F | CH | |
| 66 | 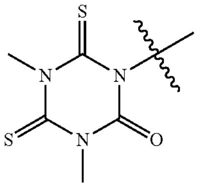 [SMILES: *n1c(=O)n(C)c(=S)n(C)c1=S] | 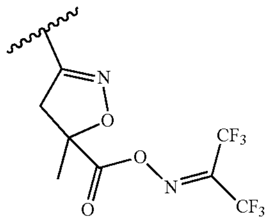 [SMILES: *C1=NOC(C)(C(=O)ON=C(C(F)(F)F)C(F)(F)F)C1] | Cl | F | CH | |

TABLE 1-continued
Structures and ${}^{1}$H NMR data of compounds
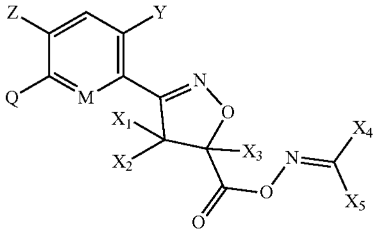
I
| NO. | Q | 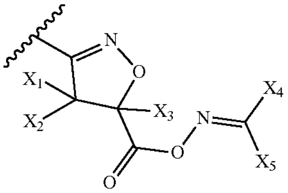 | Y | Z | M | ${}^{1}$H NMR |
|---|---|---|---|---|---|---|
| 67 | 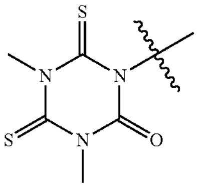 [SMILES: *n1c(=O)n(C)c(=S)n(C)c1=S] | 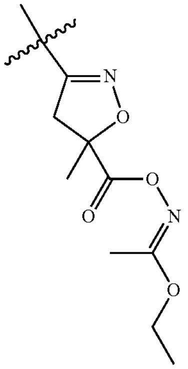 [SMILES: *C1=NOC(C)(C(=O)O/N=C(\C)OCC)C1] | Cl | F | CH | ${}^{1}$H NMR (500 MHz, DMSO-$d_6$) δ 7.97 (d, J = 7.5 Hz, 1H), 7.90 (d, J = 9.5 Hz, 1H), 4.15 (s, 3H), 4.14-4.09 (m, 2H), 3.98 (dd, J = 17.5 Hz, 1H), 3.63 (s, 3H), 3.60 (dd, J = 17.5 Hz, 1H), 2.02 (s, 3H), 1.72 (s, 3H), 1.29 (t, J = 7.0 Hz, 3H). |
| 68 | 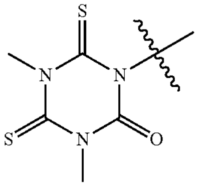 [SMILES: *n1c(=O)n(C)c(=S)n(C)c1=S] | 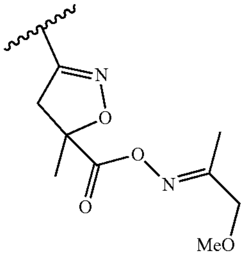 [SMILES: *C1=NOC(C)(C(=O)O/N=C(\C)COC)C1] | Cl | F | CH | ${}^{1}$H NMR (500 MHz, DMSO-$d_6$) δ 7.97 (d, J = 7.5 Hz, 1H), 7.90 (d, J = 9.5 Hz, 1H), 4.15 (s, 3H), 4.08 (s, 2H), 3.99 (dd, J = 17.5 Hz, 1H), 3.65-3.60 (m, 4H), 3.29 (s, 3H), 1.98 (s, 3H), 1.73 (s, 3H). |
| 69 | 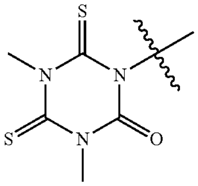 [SMILES: *n1c(=O)n(C)c(=S)n(C)c1=S] | 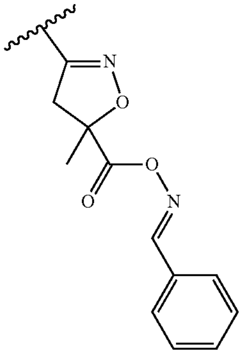 [SMILES: *C1=NOC(C)(C(=O)O/N=C/c2ccccc2)C1] | Cl | F | CH | ${}^{1}$H NMR (500 MHz, DMSO) δ 8.82 (s, 1H), 8.00 (d, J = 7.5 Hz, 1H), 7.91 (d, J = 9.5 Hz, 1H), 7.80-7.78 (m, 2H), 7.61-7.56 (m, 1H), 7.56-7.52 (m, 2H), 4.15 (s, 3H), 4.06-4.01 (m, 1H), 3.70-3.62 (m, 1H), 3.63 (s, 3H), 1.77 (s, 3H). |

TABLE 1-continued
Structures and $^1$H NMR data of compounds
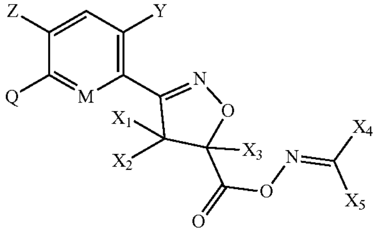
I
| NO. | Q | 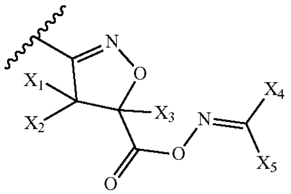 | Y | Z | M | $^1$H NMR |
|---|---|---|---|---|---|---|
| 70 | 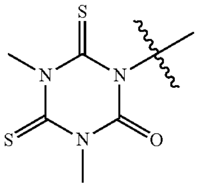 | 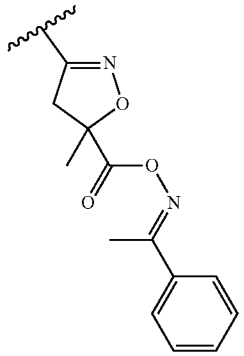 [SMILES: *C1=NOC(C)(C(=O)O/N=C(\C)c2ccccc2)C1] | Cl | F | CH | $^1$H NMR (500 MHz, DMSO) δ 7.98 (d, J = 7.5 Hz, 1H), 7.90 (d, J = 9.0 Hz, 1H), 7.82-7.75 (m, 2H), 7.55-7.46 (m, 3H), 4.14 (s, 3H), 4.09-4.01 (m, 1H), 3.70-3.65 (m, 1H), 3.62 (s, 3H), 2.39 (s, 3H), 1.77 (s, 3H). |
| 71 | 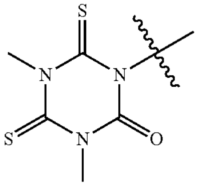 [SMILES: *n1c(=O)n(C)c(=S)n(C)c1=S] | 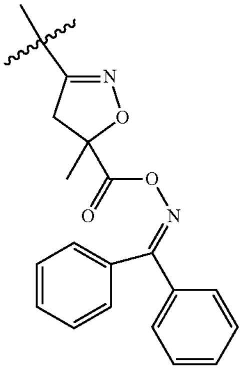 [SMILES: *C1=NOC(C)(C(=O)ON=C(c2ccccc2)c2ccccc2)C1] | Cl | F | CH | $^1$H NMR (500 MHz, DMSO) δ 7.90 (d, J = 7.5 Hz, 1H), 7.86 (d, J = 9.0 Hz, 1H), 7.58-7.52 (m, 1H), 7.54-7.45 (m, 4H), 7.43-7.40 (m, 3H), 7.33-7.30 (m, 2H), 4.14 (s, 3H), 3.69-3.62 (m, 1H), 3.62 (s, 3H), 3.48-3.42 (m, 1H), 1.51 (s, 3H). |
| 72 | 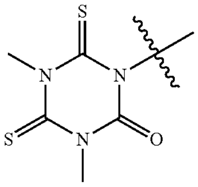 [SMILES: *n1c(=O)n(C)c(=S)n(C)c1=S] | 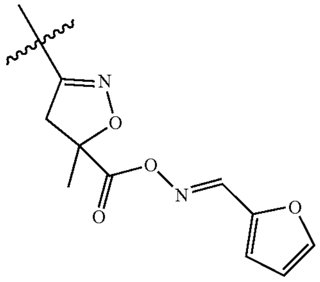 [SMILES: *C1=NOC(C)(C(=O)O/N=C/c2ccco2)C1] | Cl | F | CH | |

TABLE 1-continued
Structures and $^1$H NMR data of compounds
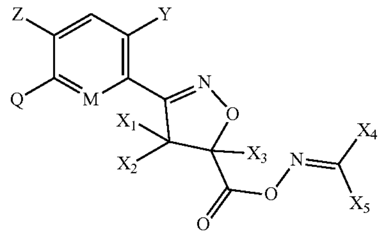
I
| NO. | Q | 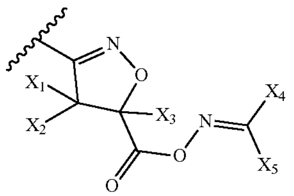 | Y | Z | M | $^1$H NMR |
|---|---|---|---|---|---|---|
| 73 | 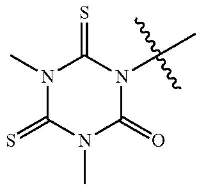 [SMILES: *n1c(=O)n(C)c(=S)n(C)c1=S] | 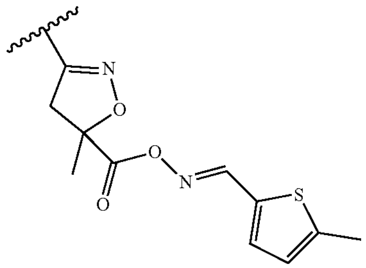 [SMILES: *C1=NOC(C)(C(=O)O/N=C/c2ccc(C)s2)C1] | Cl | F | CH | |
| 74 | 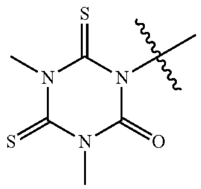 | 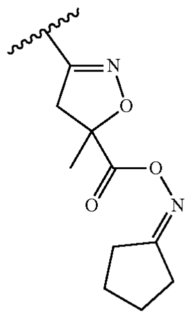 [SMILES: *C1=NOC(C)(C(=O)ON=C2CCCC2)C1] | Cl | F | CH | $^1$H NMR (500 MHz, DMSO) δ 7.96 (d, J = 7.5 Hz, 1H), 7.88 (d, J = 9.5 Hz, 1H), 4.13 (s, 3H), 3.96-3.90 (m, 1H), 3.62 (s, 3H), 3.61-3.55 (m, 1H), 2.49-2.44 (m, 4H), 2.26-2.22 (m, 4H), 1.69 (s, 3H). |
| 75 | 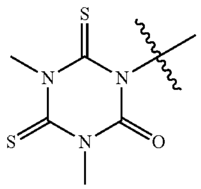 [SMILES: *n1c(=O)n(C)c(=S)n(C)c1=S] | 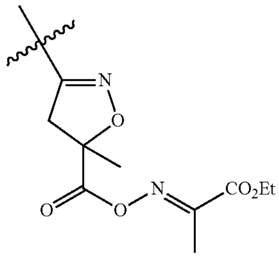 [SMILES: *C1=NOC(C)(C(=O)O/N=C(\C)C(=O)OCC)C1] | Cl | F | CH | $^1$H NMR (500 MHz, DMSO-$d_6$) δ 7.98 (d, J = 7.5 Hz, 1H), 7.91 (d, J = 9.5 Hz, 1H), 4.31 (q, J = 7.0 Hz, 2H), 4.15 (s, 3H), 4.04 (dd, J = 17.5, 9.0 Hz, 1H), 3.71-3.62 (m, 4H), 2.16 (s, 3H), 1.76 (s, 3H), 1.29 (t, J = 7.0 Hz, 3H). |
| 76 | 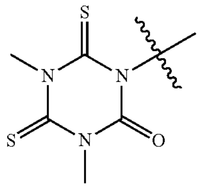 [SMILES: *n1c(=O)n(C)c(=S)n(C)c1=S] | 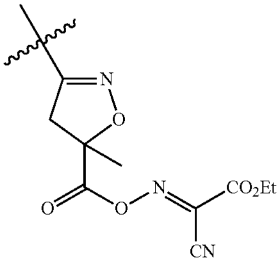 [SMILES: *C1=NOC(C)(C(=O)O/N=C(\C#N)C(=O)OCC)C1] | Cl | F | CH | |

TABLE 1-continued
Structures and $^1$H NMR data of compounds
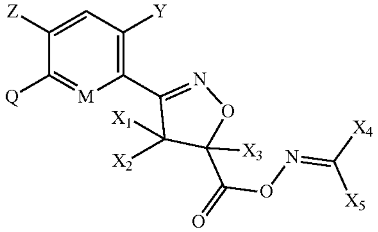
I
| NO. | Q | 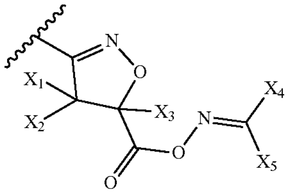 | Y | Z | M | $^1$H NMR |
|---|---|---|---|---|---|---|
| 77 | 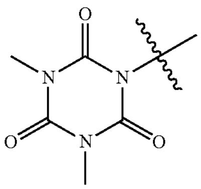 | 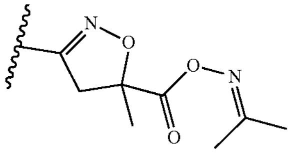 [SMILES: *C1=NOC(C)(C(=O)ON=C(C)C)C1] | Cl | F | CH | |
| 78 | 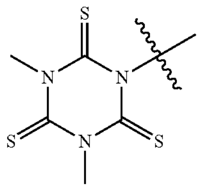 [SMILES: *n1c(=S)n(C)c(=S)n(C)c1=S] | 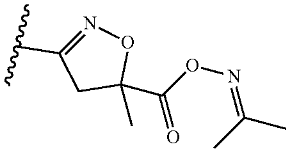 [SMILES: *C1=NOC(C)(C(=O)ON=C(C)C)C1] | Cl | F | CH | |
| 79 | 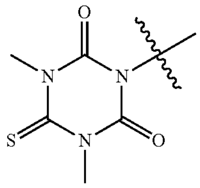 [SMILES: *n1c(=O)n(C)c(=S)n(C)c1=O] | 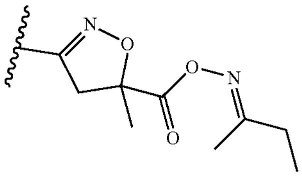 [SMILES: *C1=NOC(C)(C(=O)O/N=C(\C)CC)C1] | Cl | F | CH | $^1$H NMR (500 MHz, DMSO-$d_6$) δ 7.98-7.92 (m, 2H), 3.98 (d, J = 17.5, 1H), 3.64-3.62 (m, 7H), 2.43-2.28 (m, 2H), 1.96 (s, 3H), 1.71 (s, 3H), 1.09 (t, J = 7.5 Hz, 3H). |
| 80 | 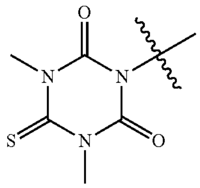 [SMILES: *n1c(=O)n(C)c(=S)n(C)c1=O] | 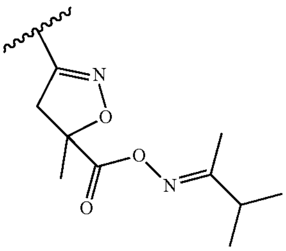 [SMILES: *C1=NOC(C)(C(=O)O/N=C(\C)C(C)C)C1] | Cl | F | CH | $^1$H NMR (500 MHz, DMSO-$d_6$) δ 7.95 (d, J = 7.5 Hz, 1H), 7.91 (d, J = 9.5 Hz, 1H), 3.96 (d, J = 17.5 Hz, 1H), 3.62 (s, 6H), 3.58 (d, J = 17.5 Hz, 1H), 2.64-2.58 (m, 1H), 1.91 (s, 3H), 1.69 (s, 3H), 1.09 (d, J = 7.0 Hz, 6H). |
| 81 | 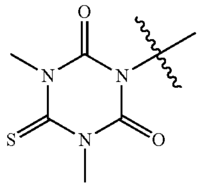 [SMILES: *n1c(=O)n(C)c(=S)n(C)c1=O] | 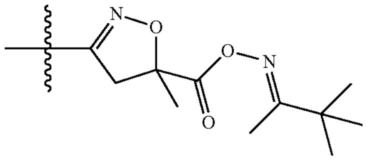 [SMILES: *C1=NOC(C)(C(=O)O/N=C(\C)C(C)(C)C)C1] | Cl | F | CH | $^1$H NMR (500 MHz, DMSO-$d_6$) δ 7.91-7.98 (m, 2H), 4.01-3.97 (m, 1H), 3.65 (s, 6H), 3.62-3.58 (m, 1H), 1.96 (s, 3H), 1.72 (s, 3H), 1.16 (s, 9H). |

TABLE 1-continued
Structures and $^1$H NMR data of compounds
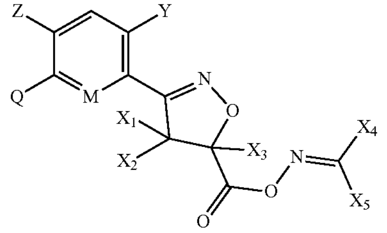
I
| NO. | Q | 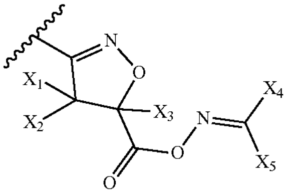 | Y | Z | M | $^1$H NMR |
|---|---|---|---|---|---|---|
| 82 | 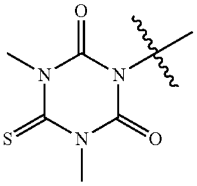 [SMILES: *n1c(=O)n(C)c(=S)n(C)c1=O] | 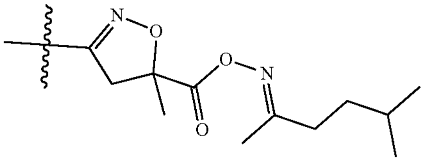 [SMILES: *C1=NOC(C)(C(=O)O/N=C(\C)CCC(C)C)C1] | Cl | F | CH | |
| 83 | 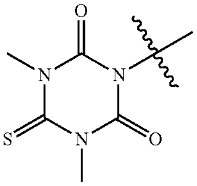 [SMILES: *n1c(=O)n(C)c(=S)n(C)c1=O] | 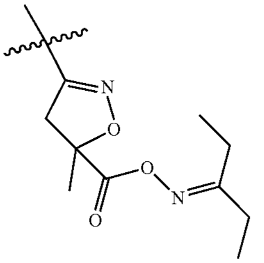 [SMILES: *C1=NOC(C)(C(=O)ON=C(CC)CC)C1] | Cl | F | CH | $^1$H NMR (500 MHz, DMSO-$d_6$) δ 7.98 (d, J = 7.5 Hz, 1H), 7.93 (d, J = 9.5 Hz, 1H), 3.98 (d, J = 17.5 Hz, 1H), 3.64-3.63 (m, 7H), 2.39-2.35 (m, 4H), 1.72 (s, 3H), 1.10 (t, J = 7.5 Hz, 3H), 1.03 (t, J = 7.5 Hz, 3H). |
| 84 | 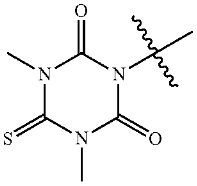 [SMILES: *n1c(=O)n(C)c(=S)n(C)c1=O] | 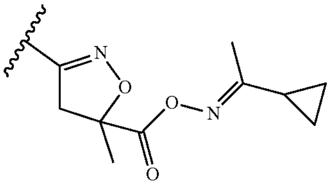 [SMILES: *C1=NOC(C)(C(=O)O/N=C(\C)C2CC2)C1] | Cl | F | CH | $^1$H NMR (500 MHz, DMSO-$d_6$) δ 7.95 (d, J = 7.5 Hz, 1H), 7.91 (d, J = 9.5 Hz, 1H), 3.97 (d, J = 17.5 Hz, 1H), 3.63 (s, 6H), 3.58 (d, J = 17.5 Hz, 1H), 2.25-2.19 (m, 1H), 1.71 (s, 3H), 1.65 (s, 3H), 0.97-0.88 (m, 4H). |
| 85 | 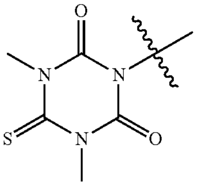 [SMILES: *n1c(=O)n(C)c(=S)n(C)c1=O] | 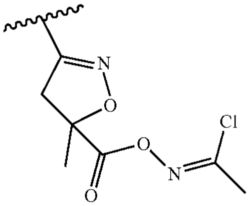 [SMILES: *C1=NOC(C)(C(=O)O/N=C(/C)Cl)C1] | Cl | F | CH | |

TABLE 1-continued
Structures and $^1$H NMR data of compounds
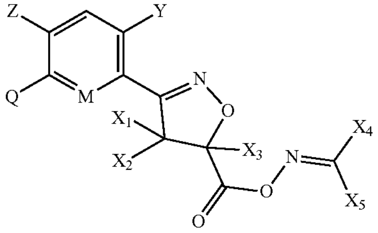
I
| NO. | Q | 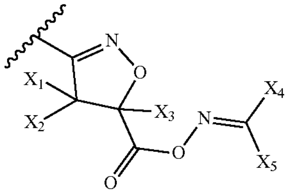 | Y | Z | M | $^1$H NMR |
|---|---|---|---|---|---|---|
| 86 | 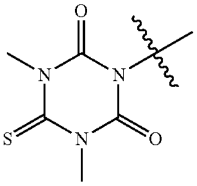 [SMILES: *n1c(=O)n(C)c(=S)n(C)c1=O] | 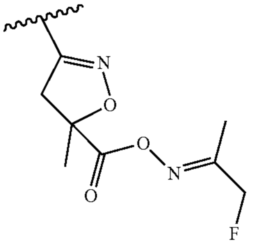 [SMILES: *C1=NOC(C)(C(=O)O/N=C(\C)CF)C1] | Cl | F | CH | |
| 87 | 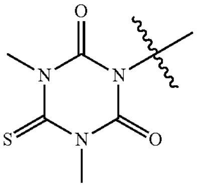 [SMILES: *n1c(=O)n(C)c(=S)n(C)c1=O] | 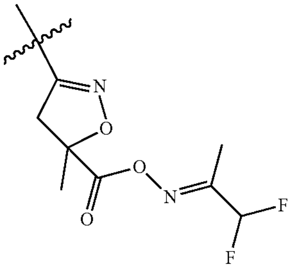 [SMILES: *C1=NOC(C)(C(=O)O/N=C(\C)C(F)F)C1] | Cl | F | CH | |
| 88 | 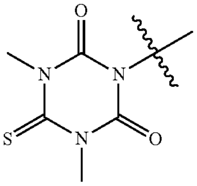 [SMILES: *n1c(=O)n(C)c(=S)n(C)c1=O] | 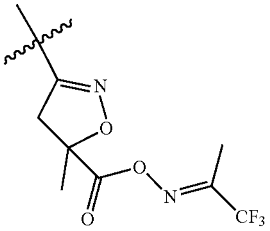 [SMILES: *C1=NOC(C)(C(=O)O/N=C(\C)C(F)(F)F)C1] | Cl | F | CH | |
| 89 | 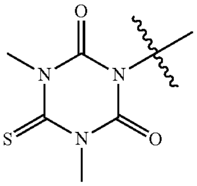 [SMILES: *n1c(=O)n(C)c(=S)n(C)c1=O] | 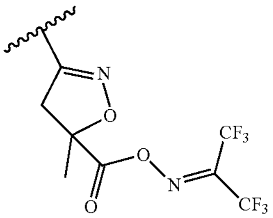 [SMILES: *C1=NOC(C)(C(=O)ON=C(C(F)(F)F)C(F)(F)F)C1] | Cl | F | CH | |

TABLE 1-continued
Structures and $^1$H NMR data of compounds
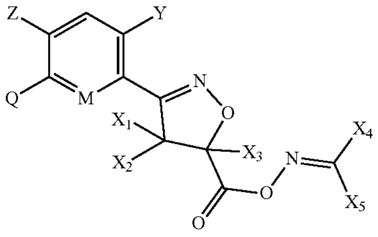
I
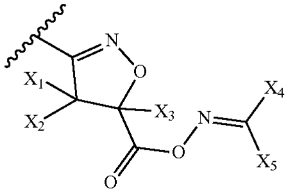
| NO. | Q | | Y | Z | M | $^1$H NMR |
|---|---|---|---|---|---|---|
| 90 | 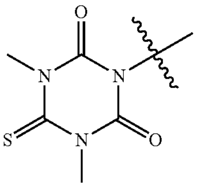 [SMILES: *n1c(=O)n(C)c(=S)n(C)c1=O] | 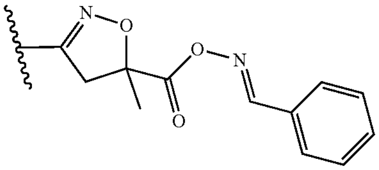 [SMILES: *C1=NOC(C)(C(=O)O/N=C/c2ccccc2)C1] | Cl | F | CH | $^1$H NMR (500 MHz, DMSO-$d_6$) δ 8.83 (s, 1H), 8.01 (d, J = 7.5 Hz, 1H), 7.94 (d, J = 9.5 Hz, 1H), 7.86-7.76 (m, 2H), 7.65-7.45 (m, 3H), 4.06 (d, J = 17.5 Hz, 1H), 3.68-3.65 (m, 7H), 1.77 (s, 3H). |
| 91 | 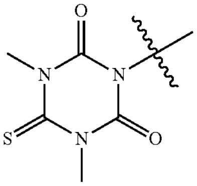 [SMILES: *n1c(=O)n(C)c(=S)n(C)c1=O] | 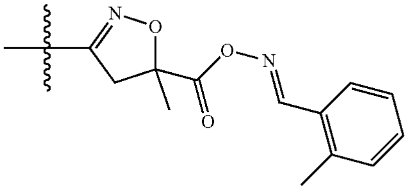 [SMILES: *C1=NOC(C)(C(=O)O/N=C/c2ccccc2C)C1] | Cl | F | CH | |
| 92 | 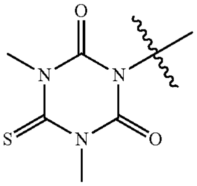 [SMILES: *n1c(=O)n(C)c(=S)n(C)c1=O] | 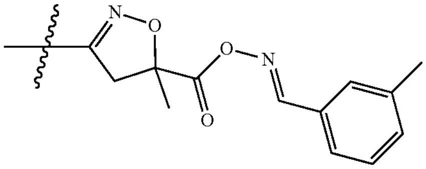 [SMILES: *C1=NOC(C)(C(=O)O/N=C/c2cccc(C)c2)C1] | Cl | F | CH | |
| 93 | 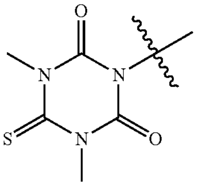 [SMILES: *n1c(=O)n(C)c(=S)n(C)c1=O] | 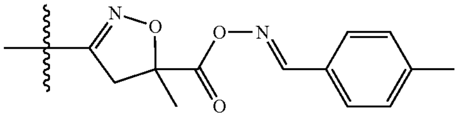 [SMILES: *C1=NOC(C)(C(=O)O/N=C/c2ccc(C)cc2)C1] | Cl | F | CH | |
| 94 | 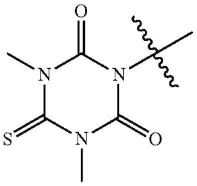 [SMILES: *n1c(=O)n(C)c(=S)n(C)c1=O] | 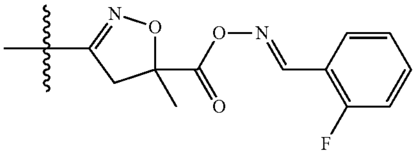 [SMILES: *C1=NOC(C)(C(=O)O/N=C/c2ccccc2F)C1] | Cl | F | CH | |

TABLE 1-continued
Structures and $^{1}H$ NMR data of compounds
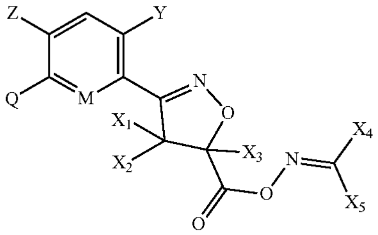
I
| NO. | Q | 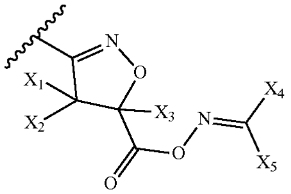 | Y | Z | M | $^{1}H$ NMR |
|---|---|---|---|---|---|---|
| 95 | 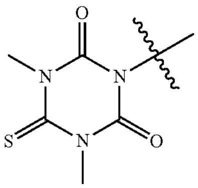 [SMILES: *n1c(=O)n(C)c(=S)n(C)c1=O] | 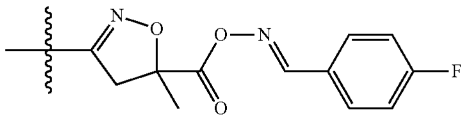 [SMILES: *C1=NOC(C)(C(=O)O/N=C/c2ccc(F)cc2)C1] | Cl | F | CH | |
| 96 | 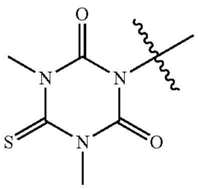 [SMILES: *n1c(=O)n(C)c(=S)n(C)c1=O] | 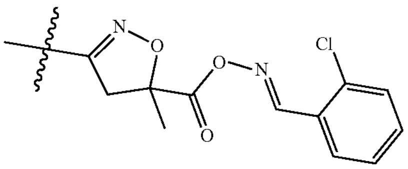 [SMILES: *C1=NOC(C)(C(=O)O/N=C/c2ccccc2Cl)C1] | Cl | F | CH | |
| 97 | 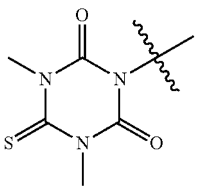 [SMILES: *n1c(=O)n(C)c(=S)n(C)c1=O] | 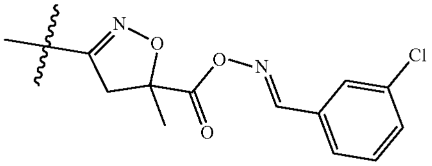 [SMILES: *C1=NOC(C)(C(=O)O/N=C/c2cccc(Cl)c2)C1] | Cl | F | CH | |
| 98 | 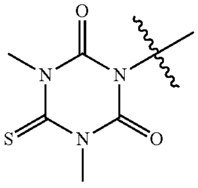 [SMILES: *n1c(=O)n(C)c(=S)n(C)c1=O] | 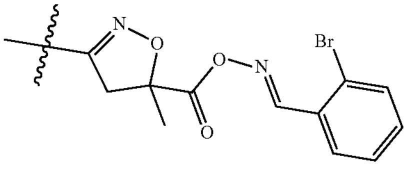 [SMILES: *C1=NOC(C)(C(=O)O/N=C/c2ccccc2Br)C1] | Cl | F | CH | |
| 99 | 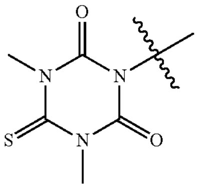 [SMILES: *n1c(=O)n(C)c(=S)n(C)c1=O] | 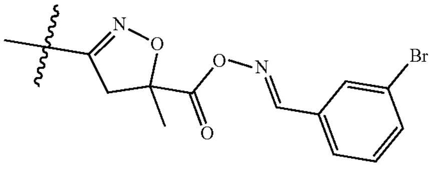 [SMILES: *C1=NOC(C)(C(=O)O/N=C/c2cccc(Br)c2)C1] | Cl | F | CH | |

TABLE 1-continued
Structures and $^1H$ NMR data of compounds
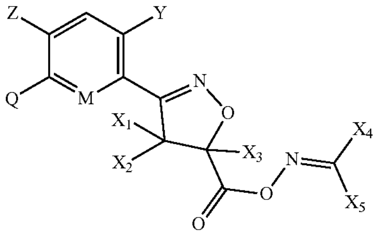
I
| NO. | Q | 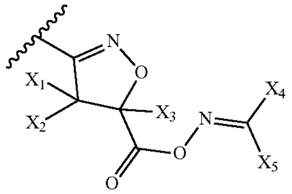 | Y | Z | M | $^1H$ NMR |
|---|---|---|---|---|---|---|
| 100 | 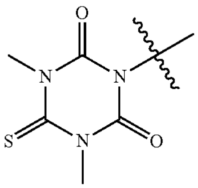 [SMILES: *n1c(=O)n(C)c(=S)n(C)c1=O] | 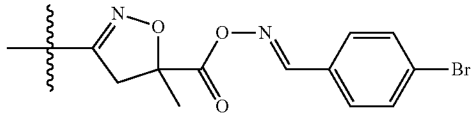 [SMILES: *C1=NOC(C)(C(=O)O/N=C/c2ccc(Br)cc2)C1] | Cl | F | CH | |
| 101 | 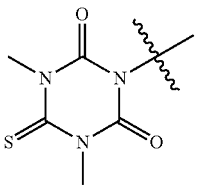 [SMILES: *n1c(=O)n(C)c(=S)n(C)c1=O] | 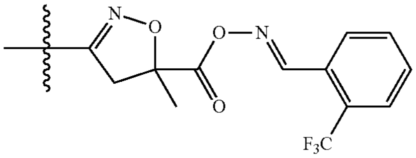 [SMILES: *C1=NOC(C)(C(=O)O/N=C/c2ccccc2C(F)(F)F)C1] | Cl | F | CH | |
| 102 | 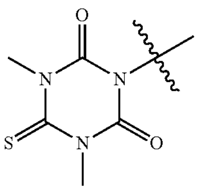 [SMILES: *n1c(=O)n(C)c(=S)n(C)c1=O] | 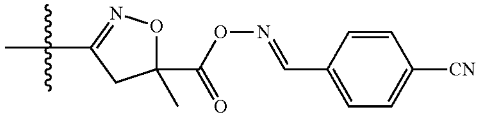 [SMILES: *C1=NOC(C)(C(=O)O/N=C/c2ccc(C#N)cc2)C1] | Cl | F | CH | |
| 103 | 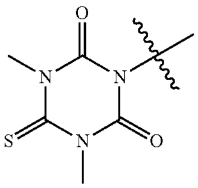 [SMILES: *n1c(=O)n(C)c(=S)n(C)c1=O] | 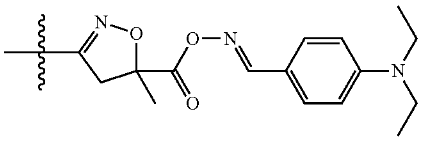 [SMILES: *C1=NOC(C)(C(=O)O/N=C/c2ccc(N(CC)CC)cc2)C1] | Cl | F | CH | |
| 104 | 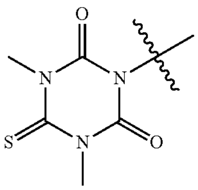 [SMILES: *n1c(=O)n(C)c(=S)n(C)c1=O] | 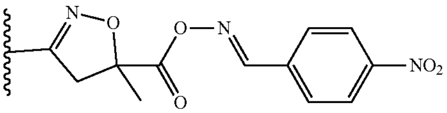 [SMILES: *C1=NOC(C)(C(=O)O/N=C/c2ccc([N+](=O)[O-])cc2)C1] | Cl | F | CH | |

TABLE 1-continued
Structures and $^1$H NMR data of compounds
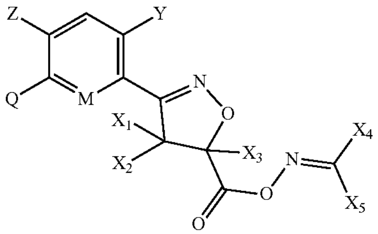
I
| NO. | Q | 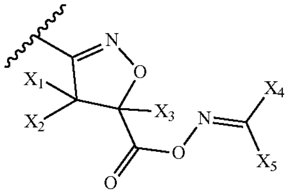 | Y | Z | M | $^1$H NMR |
|---|---|---|---|---|---|---|
| 105 | 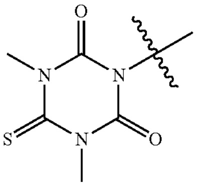 [SMILES: *n1c(=O)n(C)c(=S)n(C)c1=O] | 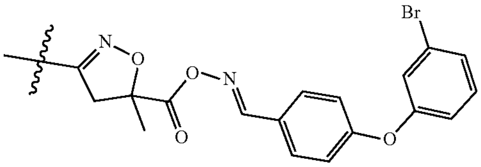 [SMILES: *C1=NOC(C)(C(=O)O/N=C/c2ccc(Oc3cccc(Br)c3)cc2)C1] | Cl | F | CH | |
| 106 | 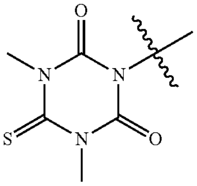 [SMILES: *n1c(=O)n(C)c(=S)n(C)c1=O] | 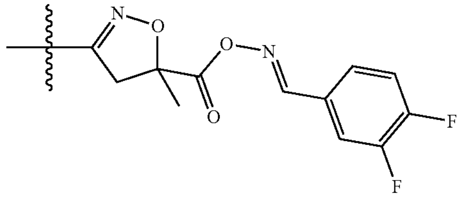 [SMILES: *C1=NOC(C)(C(=O)O/N=C/c2ccc(F)c(F)c2)C1] | Cl | F | CH | |
| 107 | 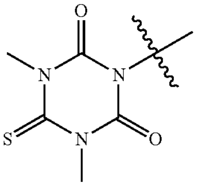 [SMILES: *n1c(=O)n(C)c(=S)n(C)c1=O] | 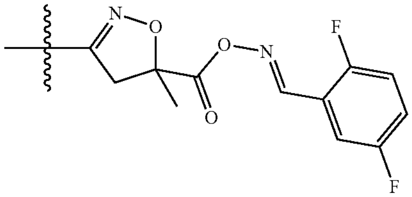 [SMILES: *C1=NOC(C)(C(=O)O/N=C/c2cc(F)ccc2F)C1] | Cl | F | CH | |
| 108 | 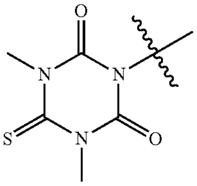 [SMILES: *n1c(=O)n(C)c(=S)n(C)c1=O] | 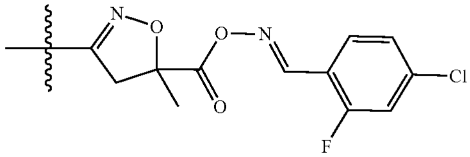 [SMILES: *C1=NOC(C)(C(=O)O/N=C/c2ccc(Cl)cc2F)C1] | Cl | F | CH | |
| 109 | 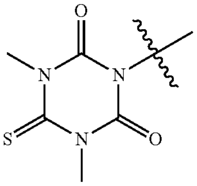 [SMILES: *n1c(=O)n(C)c(=S)n(C)c1=O] | 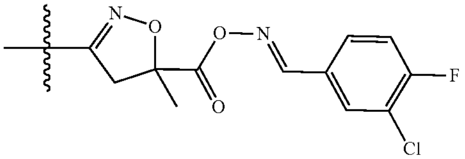 [SMILES: *C1=NOC(C)(C(=O)O/N=C/c2ccc(F)c(Cl)c2)C1] | Cl | F | CH | |

TABLE 1-continued
Structures and $^1$H NMR data of compounds
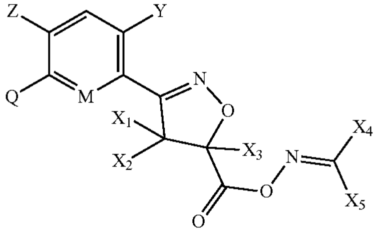
I
| NO. | Q | 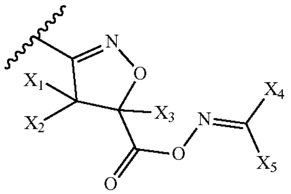 | Y | Z | M | $^1$H NMR |
|---|---|---|---|---|---|---|
| 110 | 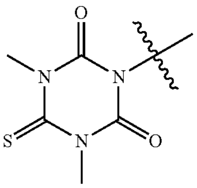 [SMILES: *n1c(=O)n(C)c(=S)n(C)c1=O] | 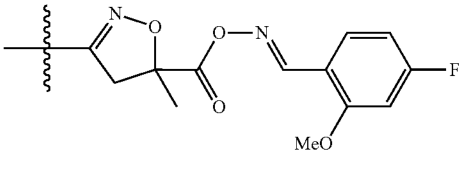 [SMILES: *C1=NOC(C)(C(=O)O/N=C/c2ccc(F)cc2OC)C1] | Cl | F | CH | |
| 111 | 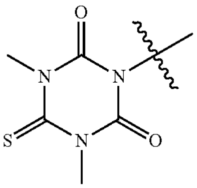 [SMILES: *n1c(=O)n(C)c(=S)n(C)c1=O] | 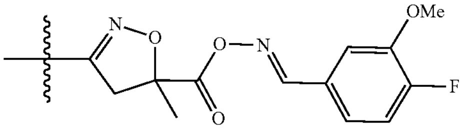 [SMILES: *C1=NOC(C)(C(=O)O/N=C/c2ccc(F)c(OC)c2)C1] | Cl | F | CH | |
| 112 | 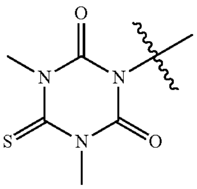 [SMILES: *n1c(=O)n(C)c(=S)n(C)c1=O] | 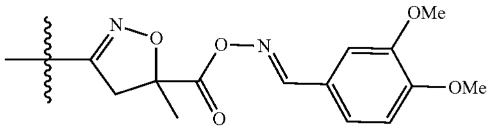 [SMILES: *C1=NOC(C)(C(=O)O/N=C/c2ccc(OC)c(OC)c2)C1] | Cl | F | CH | |
| 113 | 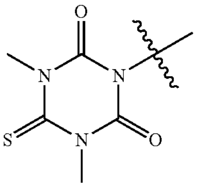 [SMILES: *n1c(=O)n(C)c(=S)n(C)c1=O] | 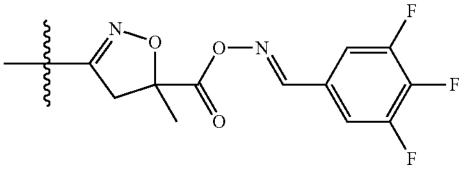 [SMILES: *C1=NOC(C)(C(=O)O/N=C/c2cc(F)c(F)c(F)c2)C1] | Cl | F | CH | |
| 114 | 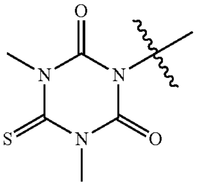 [SMILES: *n1c(=O)n(C)c(=S)n(C)c1=O] | 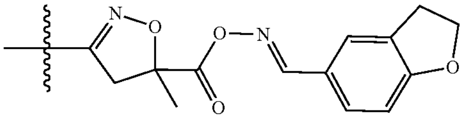 [SMILES: *C1=NOC(C)(C(=O)O/N=C/c2ccc3c(c2)CCO3)C1] | Cl | F | CH | |

TABLE 1-continued
Structures and $^1H$ NMR data of compounds
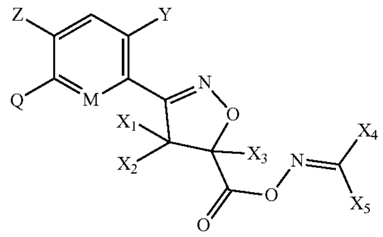
I
| NO. | Q | 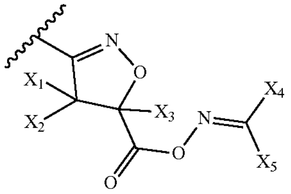 | Y | Z | M | $^1H$ NMR |
|---|---|---|---|---|---|---|
| 115 | 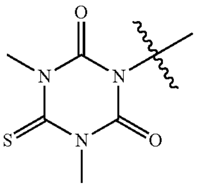 [SMILES: *n1c(=O)n(C)c(=S)n(C)c1=O] | 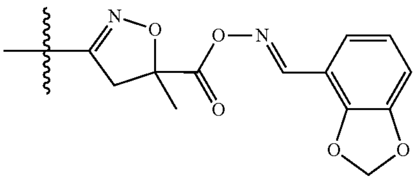 [SMILES: *C1=NOC(C)(C(=O)O/N=C/c2cccc3c2OCO3)C1] | Cl | F | CH | |
| 116 | 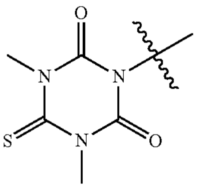 [SMILES: *n1c(=O)n(C)c(=S)n(C)c1=O] | 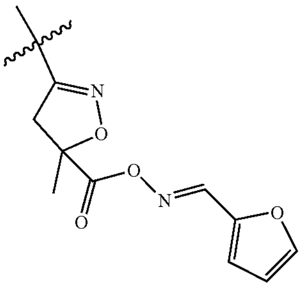 [SMILES: *C1=NOC(C)(C(=O)O/N=C/c2ccco2)C1] | Cl | F | CH | |
| 117 | 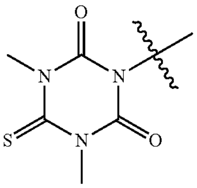 [SMILES: *n1c(=O)n(C)c(=S)n(C)c1=O] | 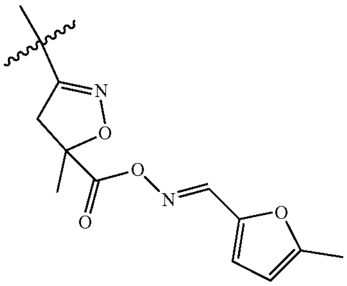 [SMILES: *C1=NOC(C)(C(=O)O/N=C/c2ccc(C)o2)C1] | Cl | F | CH | $^1H$ NMR (500 MHz, DMSO-$d_6$) δ 8.59 (s, 1H), 8.05-7.86 (m, 2H), 7.04 (d, J = 3.5 Hz, 1H), 6.38 (d, J = 3.5 Hz, 1H), 4.04 (d, J = 17.5 Hz, 1H), 3.65 (s, 6H), 3.64-3.58 (m, 1H), 2.39 (s, 3H), 1.74 (s, 3H). |
| 118 | 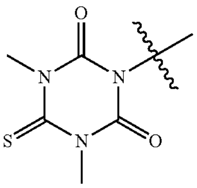 [SMILES: *n1c(=O)n(C)c(=S)n(C)c1=O] | 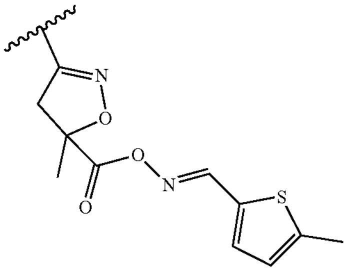 [SMILES: *C1=NOC(C)(C(=O)O/N=C/c2ccc(C)s2)C1] | Cl | F | CH | $^1H$ NMR (500 MHz, DMSO-$d_6$) δ 8.91 (s, 1H), 8.10-7.83 (m, 2H), 7.48 (d, J = 3.5 Hz, 1H), 6.96 (d, J = 3.5 Hz, 1H), 4.04 (d, J = 17.5 Hz, 1H), 3.65 (s, 6H), 3.64-3.58 (m, 1H), 2.52 (s, 3H), 1.74 (s, 3H). |

TABLE 1-continued
Structures and $^1$H NMR data of compounds
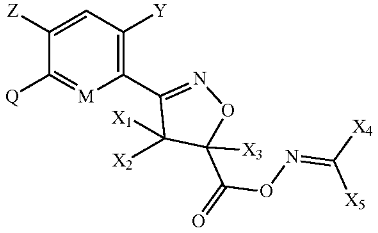
I
| NO. | Q | 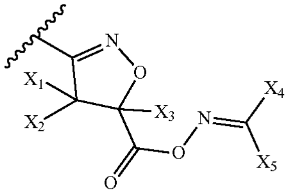 | Y | Z | M | $^1$H NMR |
|---|---|---|---|---|---|---|
| 119 | 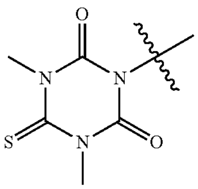 [SMILES: *n1c(=O)n(C)c(=S)n(C)c1=O] | 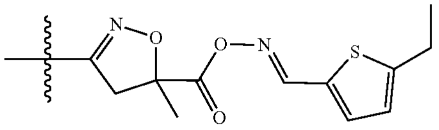 [SMILES: *C1=NOC(C)(C(=O)O/N=C/c2ccc(CC)s2)C1] | Cl | F | CH | |
| 120 | 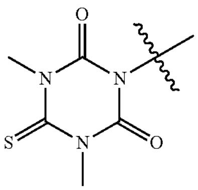 [SMILES: *n1c(=O)n(C)c(=S)n(C)c1=O] | 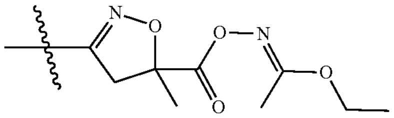 [SMILES: *C1=NOC(C)(C(=O)O/N=C(\C)OCC)C1] | Cl | F | CH | $^1$H NMR (500 MHz, DMSO-$d_6$) δ 7.97 (d, J = 7.5 Hz, 1H), 7.93 (d, J = 9.5 Hz, 1H), 4.13 (q, J = 7.0 Hz, 2H), 3.99 (d, J = 17.5 Hz, 1H), 3.65-3.60 (m, 7H), 2.03 (s, 3H), 1.72 (s, 3H), 1.29 (t, J = 7.0 Hz, 3H). |
| 121 | 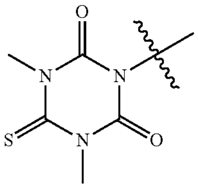 [SMILES: *n1c(=O)n(C)c(=S)n(C)c1=O] | 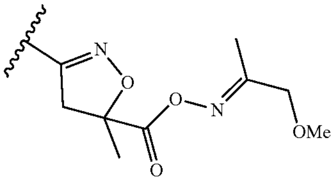 [SMILES: *C1=NOC(C)(C(=O)O/N=C(\C)COC)C1] | Cl | F | CH | $^1$H NMR (500 MHz, DMSO-$d_6$) δ 7.96 (d, J = 7.5 Hz, 1H), 7.91 (d, J = 9.5 Hz, 1H), 4.01-3.97 (m, 1H), 3.73-3.69 (m, 1H), 3.63 (s, 6H), 3.60-3.56 (m, 1H), 3.51-3.46 (m, 1H), 3.26 (s, 3H), 1.96 (s, 3H), 1.70 (s, 3H). |
| 122 | 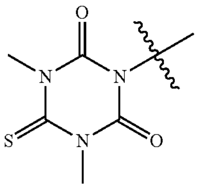 [SMILES: *n1c(=O)n(C)c(=S)n(C)c1=O] | 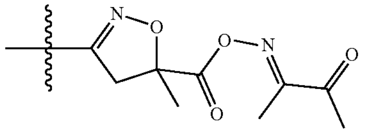 [SMILES: *C1=NOC(C)(C(=O)O/N=C(\C)C(C)=O)C1] | Cl | F | CH | |

TABLE 1-continued
Structures and $^1$H NMR data of compounds
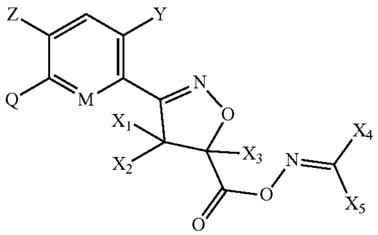
I
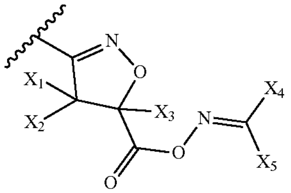
| NO. | Q | | Y | Z | M | $^1$H NMR |
|---|---|---|---|---|---|---|
| 123 | 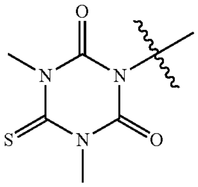 [SMILES: *n1c(=O)n(C)c(=S)n(C)c1=O] | 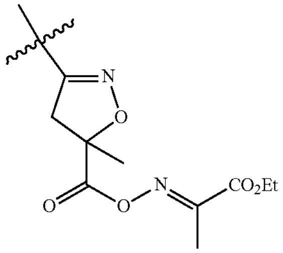 [SMILES: *C1=NOC(C)(C(=O)O/N=C(\C)C(=O)OCC)C1] | Cl | F | CH | $^1$H NMR (500 MHz, DMSO-$d_6$) δ 7.97 (d, J = 7.5 Hz, 1H), 7.92 (d, J = 9.5 Hz, 1H), 4.21 (q, J = 7.0 Hz, 2H), 3.92 (d, J = 17.5 Hz, 1H), 3.65 (s, 6H), 3.54 (d, J = 17.5 Hz, 1H), 1.94 (s, 3H), 1.64 (s, 3H), 1.26 (t, J = 7.0 Hz, 3H). |
| 124 | 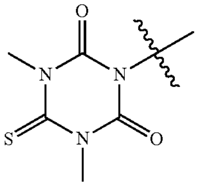 [SMILES: *n1c(=O)n(C)c(=S)n(C)c1=O] | 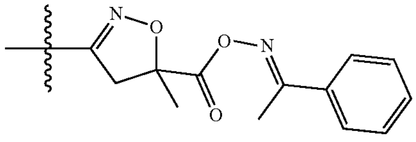 [SMILES: *C1=NOC(C)(C(=O)O/N=C(\C)c2ccccc2)C1] | Cl | F | CH | $^1$H NMR (500 MHz, DMSO-$d_6$) δ 8.01 (d, J = 7.5 Hz, 1H), 7.94 (d, J = 9.5 Hz, 1H), 7.83-7.76 (m, 2H), 7.60-7.48 (m, 3H), 4.07 (d, J = 17.5 Hz, 1H), 3.69-3.64 (m, 7H), 2.41 (s, 3H), 1.79 (s, 3H). |
| 125 | 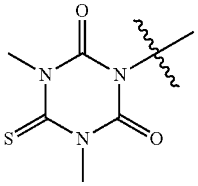 [SMILES: *n1c(=O)n(C)c(=S)n(C)c1=O] | 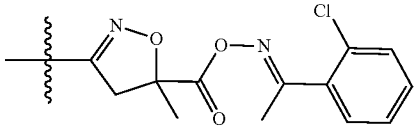 [SMILES: *C1=NOC(C)(C(=O)O/N=C(\C)c2ccccc2Cl)C1] | Cl | F | CH | |
| 126 | 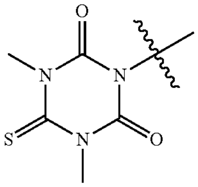 [SMILES: *n1c(=O)n(C)c(=S)n(C)c1=O] | 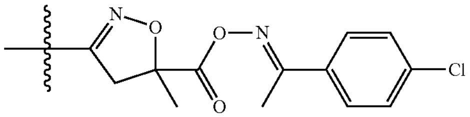 [SMILES: *C1=NOC(C)(C(=O)O/N=C(\C)c2ccc(Cl)cc2)C1] | Cl | F | CH | |
| 127 | 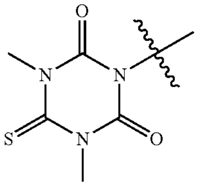 [SMILES: *n1c(=O)n(C)c(=S)n(C)c1=O] | 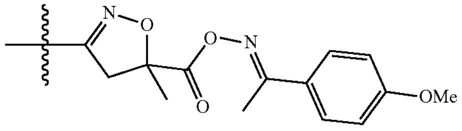 [SMILES: *C1=NOC(C)(C(=O)O/N=C(\C)c2ccc(OC)cc2)C1] | Cl | F | CH | |

TABLE 1-continued
Structures and $^1$H NMR data of compounds
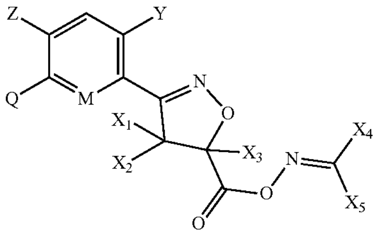
I
| NO. | Q | 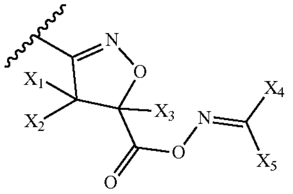 | Y | Z | M | $^1$H NMR |
|---|---|---|---|---|---|---|
| 128 | 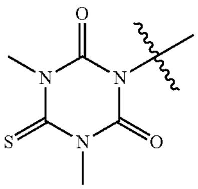 [SMILES: *n1c(=O)n(C)c(=S)n(C)c1=O] | 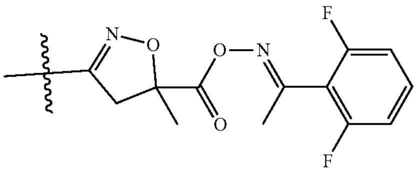 [SMILES: *C1=NOC(C)(C(=O)O/N=C(\C)c2c(F)cccc2F)C1] | Cl | F | CH | |
| 129 | 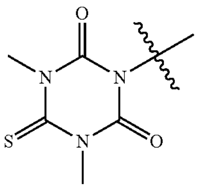 [SMILES: *n1c(=O)n(C)c(=S)n(C)c1=O] | 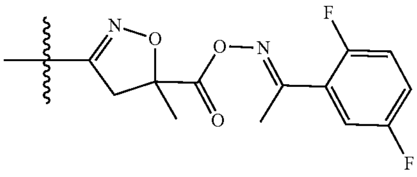 [SMILES: *C1=NOC(C)(C(=O)O/N=C(\C)c2cc(F)ccc2F)C1] | Cl | F | CH | |
| 130 | 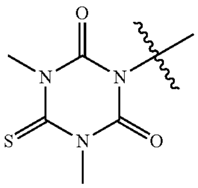 [SMILES: *n1c(=O)n(C)c(=S)n(C)c1=O] | 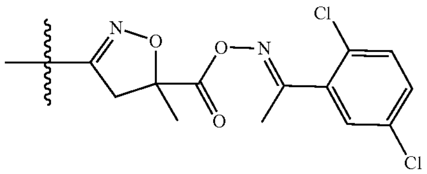 [SMILES: *C1=NOC(C)(C(=O)O/N=C(\C)c2cc(Cl)ccc2Cl)C1] | Cl | F | CH | |
| 131 | 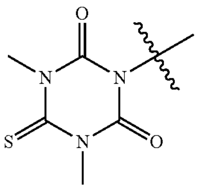 [SMILES: *n1c(=O)n(C)c(=S)n(C)c1=O] | 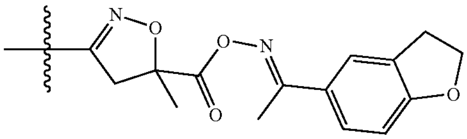 [SMILES: *C1=NOC(C)(C(=O)O/N=C(\C)c2ccc3c(c2)CCO3)C1] | Cl | F | CH | |
| 132 | 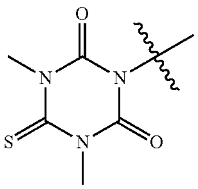 [SMILES: *n1c(=O)n(C)c(=S)n(C)c1=O] | 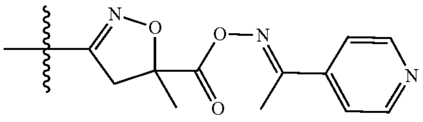 [SMILES: *C1=NOC(C)(C(=O)O/N=C(\C)c2ccncc2)C1] | Cl | F | CH | |

TABLE 1-continued
Structures and $^1H$ NMR data of compounds
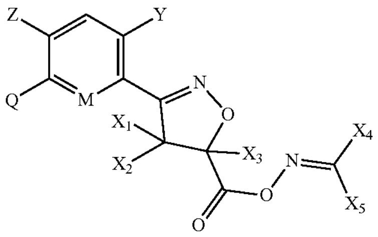
I
| NO. | Q | 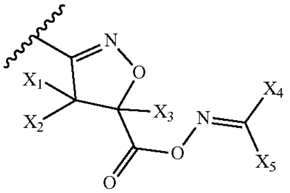 | Y | Z | M | $^1H$ NMR |
|---|---|---|---|---|---|---|
| 133 | 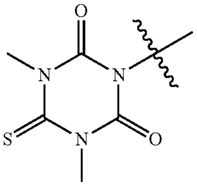 [SMILES: *n1c(=O)n(C)c(=S)n(C)c1=O] | 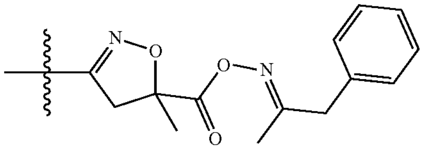 [SMILES: *C1=NOC(C)(C(=O)O/N=C(\C)Cc2ccccc2)C1] | Cl | F | CH | |
| 134 | 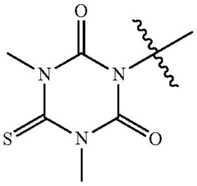 [SMILES: *n1c(=O)n(C)c(=S)n(C)c1=O] | 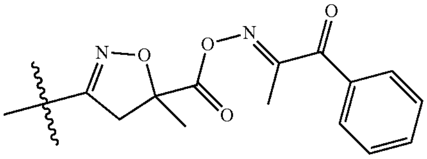 [SMILES: *C1=NOC(C)(C(=O)O/N=C(\C)C(=O)c2ccccc2)C1] | Cl | F | CH | |
| 135 | 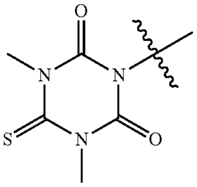 [SMILES: *n1c(=O)n(C)c(=S)n(C)c1=O] | 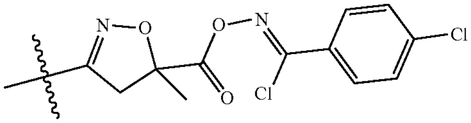 [SMILES: *C1=NOC(C)(C(=O)O/N=C(\Cl)c2ccc(Cl)cc2)C1] | Cl | F | CH | |
| 136 | 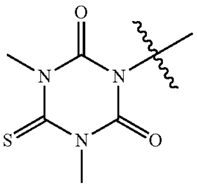 [SMILES: *n1c(=O)n(C)c(=S)n(C)c1=O] | 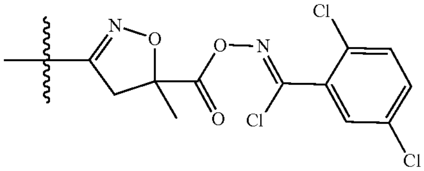 [SMILES: *C1=NOC(C)(C(=O)O/N=C(\Cl)c2cc(Cl)ccc2Cl)C1] | Cl | F | CH | |
| 137 | 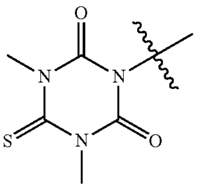 [SMILES: *n1c(=O)n(C)c(=S)n(C)c1=O] | 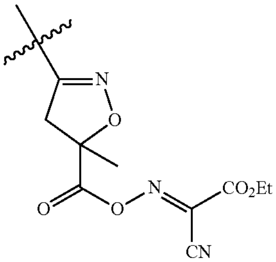 [SMILES: *C1=NOC(C)(C(=O)O/N=C(\C#N)C(=O)OCC)C1] | Cl | F | CH | |

TABLE 1-continued
Structures and $^{1}H$ NMR data of compounds
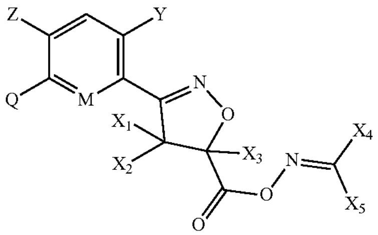
I
| NO. | Q | 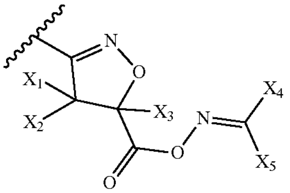 | Y | Z | M | $^{1}H$ NMR |
|---|---|---|---|---|---|---|
| 138 | 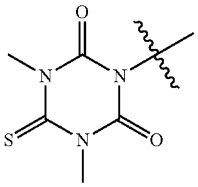 [SMILES: *n1c(=O)n(C)c(=S)n(C)c1=O] | 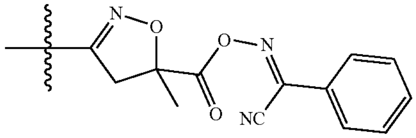 [SMILES: *C1=NOC(C)(C(=O)O/N=C(\C#N)c2ccccc2)C1] | Cl | F | CH | |
| 139 | 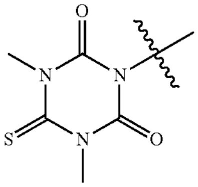 [SMILES: *n1c(=O)n(C)c(=S)n(C)c1=O] | 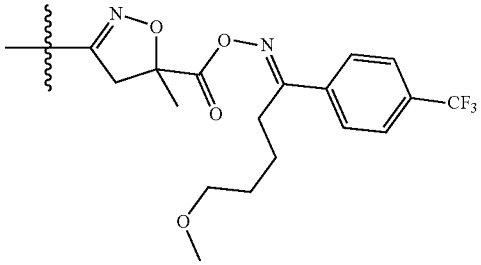 [SMILES: *C1=NOC(C)(C(=O)O/N=C(\CCCCOC)c2ccc(C(F)(F)F)cc2)C1] | Cl | F | CH | |
| 140 | 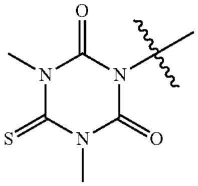 [SMILES: *n1c(=O)n(C)c(=S)n(C)c1=O] | 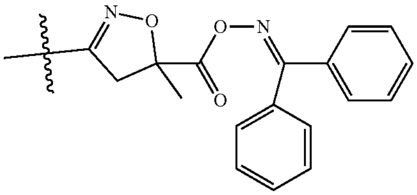 [SMILES: *C1=NOC(C)(C(=O)ON=C(c2ccccc2)c2ccccc2)C1] | Cl | F | CH | $^{1}H$ NMR (500 MHz, DMSO-$d_6$) δ 7.92-7.89 (m, 2H), 7.54-7.48 (m, 4H), 7.42-7.41 (m, 4H), 7.36-7.27 (m, 2H), 3.68-3.64 (m, 7H), 3.48 (d, J = 17.5 Hz, 1H), 1.54 (s, 3H). |
| 141 | 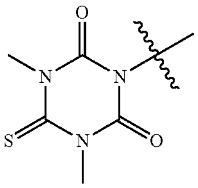 [SMILES: *n1c(=O)n(C)c(=S)n(C)c1=O] | 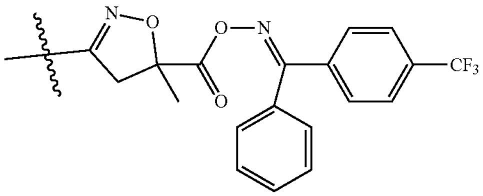 [SMILES: *C1=NOC(C)(C(=O)O/N=C(\c2ccccc2)c2ccc(C(F)(F)F)cc2)C1] | Cl | F | CH | |
| 142 | 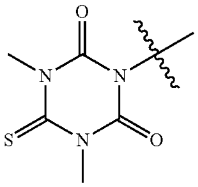 [SMILES: *n1c(=O)n(C)c(=S)n(C)c1=O] | 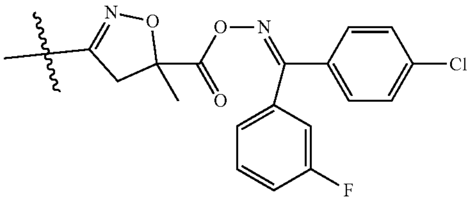 [SMILES: *C1=NOC(C)(C(=O)O/N=C(/c2ccc(Cl)cc2)c2cccc(F)c2)C1] | Cl | F | CH | |

TABLE 1-continued
Structures and $^{1}H$ NMR data of compounds
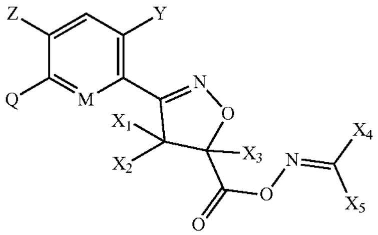
I
| NO. | Q | 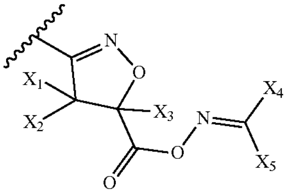 | Y | Z | M | $^{1}H$ NMR |
|---|---|---|---|---|---|---|
| 143 | 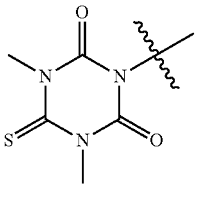 [SMILES: *n1c(=O)n(C)c(=S)n(C)c1=O] | 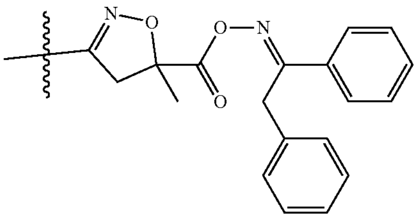 [SMILES: *C1=NOC(C)(C(=O)O/N=C(\Cc2ccccc2)c2ccccc2)C1] | Cl | F | CH | |
| 144 | 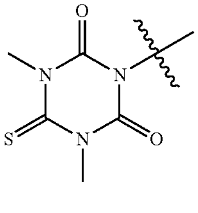 [SMILES: *n1c(=O)n(C)c(=S)n(C)c1=O] | 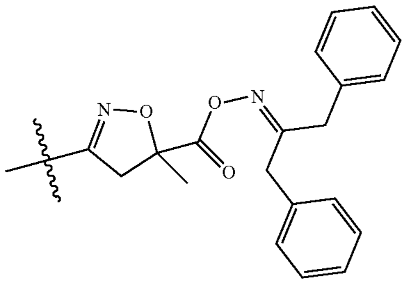 [SMILES: *C1=NOC(C)(C(=O)ON=C(Cc2ccccc2)Cc2ccccc2)C1] | Cl | F | CH | |
| 145 | 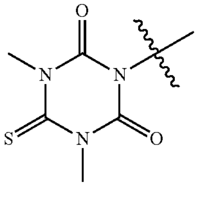 [SMILES: *n1c(=O)n(C)c(=S)n(C)c1=O] | 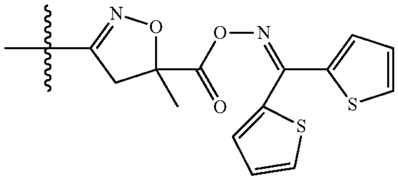 [SMILES: *C1=NOC(C)(C(=O)ON=C(c2cccs2)c2cccs2)C1] | Cl | F | CH | |
| 146 | 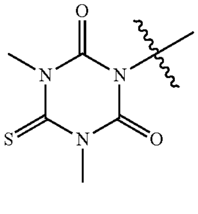 [SMILES: *n1c(=O)n(C)c(=S)n(C)c1=O] | 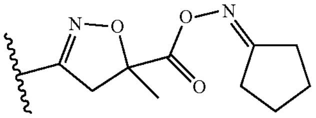 [SMILES: *C1=NOC(C)(C(=O)ON=C2CCCC2)C1] | Cl | F | CH | $^{1}H$ NMR (500 MHz, DMSO-$d_6$) δ 7.98 (d, J = 7.5 Hz, 1H), 7.94 (d, J = 9.5 Hz, 1H), 3.77 (s, 6H), 3.47 (d, J = 17.5 Hz, 1H), 2.82-2.75 (m, 2H), 2.39-2.29 (m, 2H), 1.42 (s, 3H), 1.14-1.00 (m, 2H), 0.83-0.70 (m, 2H). |

TABLE 1-continued
Structures and $^{1}$H NMR data of compounds
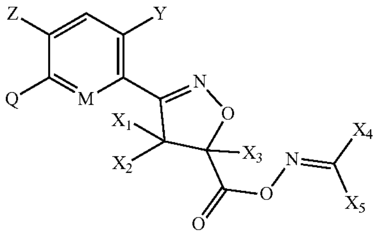
I
| NO. | Q | 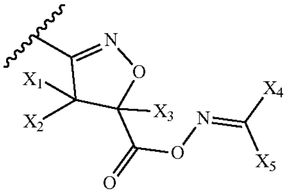 | Y | Z | M | $^{1}$H NMR |
|---|---|---|---|---|---|---|
| 147 | 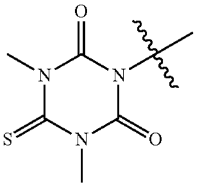 [SMILES: *n1c(=O)n(C)c(=S)n(C)c1=O] | 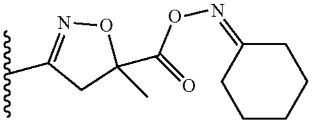 [SMILES: *C1=NOC(C)(C(=O)ON=C2CCCCC2)C1] | Cl | F | CH | |
| 148 | 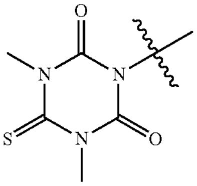 [SMILES: *n1c(=O)n(C)c(=S)n(C)c1=O] | 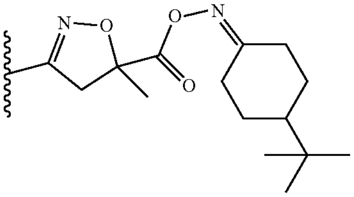 [SMILES: *C1=NOC(C)(C(=O)ON=C2CCC(C(C)(C)C)CC2)C1] | Cl | F | CH | |
| 149 | 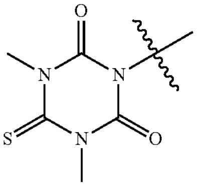 [SMILES: *n1c(=O)n(C)c(=S)n(C)c1=O] | 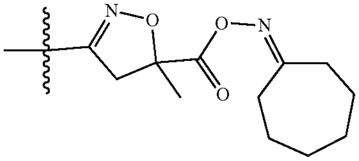 [SMILES: *C1=NOC(C)(C(=O)ON=C2CCCCCC2)C1] | Cl | F | CH | |
| 150 | 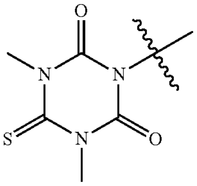 [SMILES: *n1c(=O)n(C)c(=S)n(C)c1=O] | 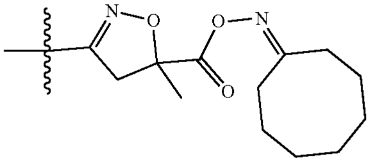 [SMILES: *C1=NOC(C)(C(=O)ON=C2CCCCCCC2)C1] | Cl | F | CH | |
| 151 | 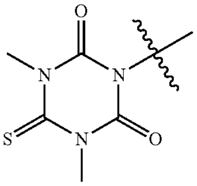 [SMILES: *n1c(=O)n(C)c(=S)n(C)c1=O] | 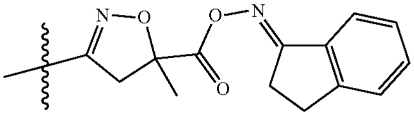 [SMILES: *C1=NOC(C)(C(=O)O/N=C2\CCc3ccccc32)C1] | Cl | F | CH | |

TABLE 1-continued
Structures and $^{1}$H NMR data of compounds
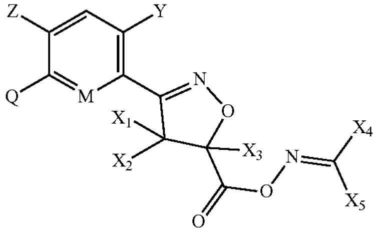
I
| NO. | Q | 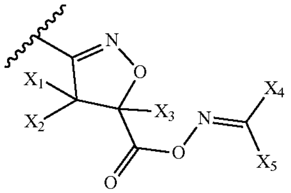 | Y | Z | M | $^{1}$H NMR |
| --- | --- | --- | --- | --- | --- | --- |
| 152 | 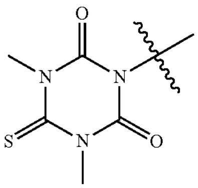 [SMILES: *n1c(=O)n(C)c(=S)n(C)c1=O] | 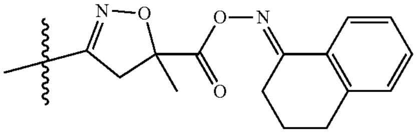 [SMILES: *C1=NOC(C)(C(=O)O/N=C2\CCCc3ccccc32)C1] | Cl | F | CH | |
| 153 | 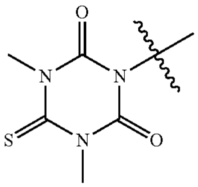 [SMILES: *n1c(=O)n(C)c(=S)n(C)c1=O] | 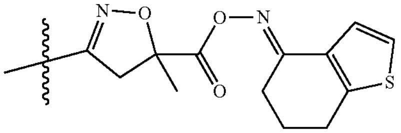 [SMILES: *C1=NOC(C)(C(=O)O/N=C2\CCCc3sccc32)C1] | Cl | F | CH | |
| 154 | 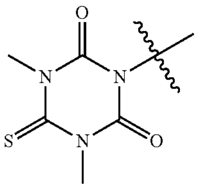 [SMILES: *n1c(=O)n(C)c(=S)n(C)c1=O] | 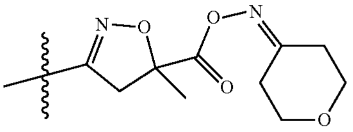 [SMILES: *C1=NOC(C)(C(=O)ON=C2CCOCC2)C1] | Cl | F | CH | |
| 155 | 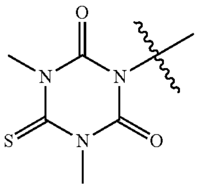 [SMILES: *n1c(=O)n(C)c(=S)n(C)c1=O] | 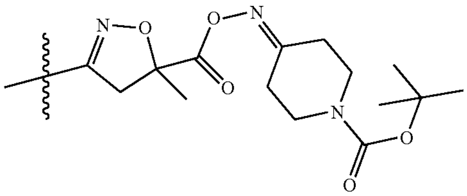 [SMILES: *C1=NOC(C)(C(=O)ON=C2CCN(C(=O)OC(C)(C)C)CC2)C1] | Cl | F | CH | |
| 156 | 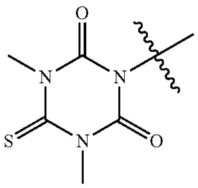 [SMILES: *n1c(=O)n(C)c(=S)n(C)c1=O] | 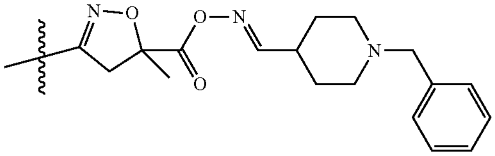 [SMILES: *C1=NOC(C)(C(=O)O/N=C/C2CCN(Cc3ccccc3)CC2)C1] | Cl | F | CH | |

TABLE 1-continued
Structures and $^{1}H$ NMR data of compounds
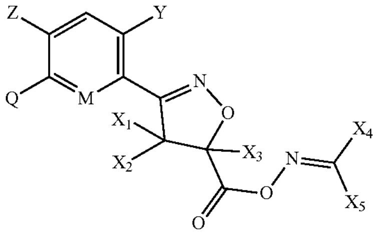
I
| NO. | Q | 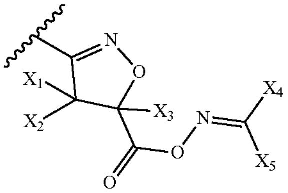 | Y | Z | M | $^{1}H$ NMR |
|---|---|---|---|---|---|---|
| 157 | 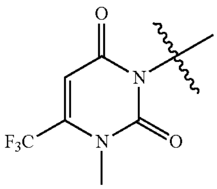 [SMILES: *n1c(=O)cc(C(F)(F)F)n(C)c1=O] | 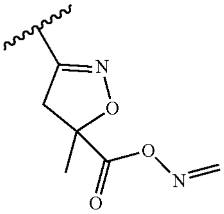 [SMILES: *C1=NOC(C)(C(=O)ON=C)C1] | Cl | F | CH | |
| 158 | 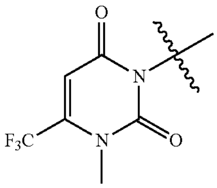 [SMILES: *n1c(=O)cc(C(F)(F)F)n(C)c1=O] | 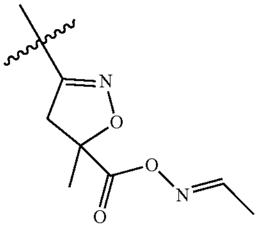 [SMILES: *C1=NOC(C)(C(=O)O/N=C/C)C1] | Cl | F | CH | |
| 159 | 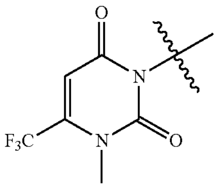 [SMILES: *n1c(=O)cc(C(F)(F)F)n(C)c1=O] | 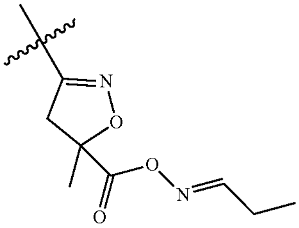 [SMILES: *C1=NOC(C)(C(=O)O/N=C/CC)C1] | Cl | F | CH | |
| 160 | 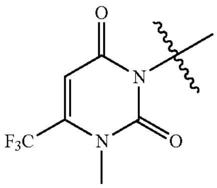 [SMILES: *n1c(=O)cc(C(F)(F)F)n(C)c1=O] | 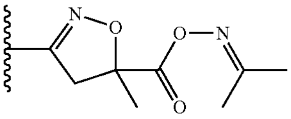 [SMILES: *C1=NOC(C)(C(=O)ON=C(C)C)C1] | Cl | F | CH | $^{1}H$ NMR (500 MHz, Chloroform-d) δ 7.32 (d, J = 9.0 Hz, 1H), 7.22 (d, J = 8.0 Hz, 1H), 6.08 (s, 1H), 3.85 (s, 3H), 3.41 (d, J = 18.0 Hz, 1H), 3.05 (d, J = 18.0 Hz, 1H), 2.66 (s, 6H), 1.50 (s, 3H). |

TABLE 1-continued
Structures and $^{1}H$ NMR data of compounds
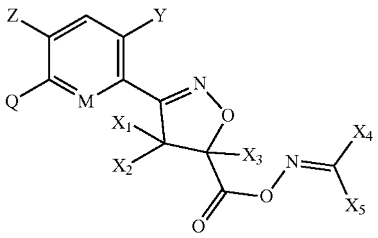
I
| NO. | Q | 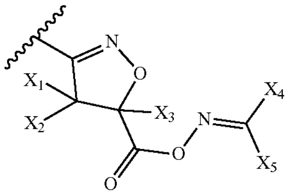 | Y | Z | M | $^{1}H$ NMR |
|---|---|---|---|---|---|---|
| 161 | 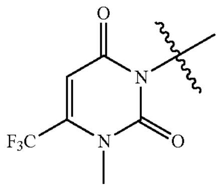 [SMILES: *n1c(=O)cc(C(F)(F)F)n(C)c1=O] | 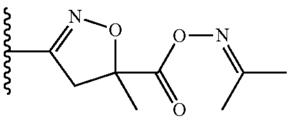 [SMILES: *C1=NOC(C)(C(=O)ON=C(C)C)C1] | Cl | H | CH | |
| 162 | 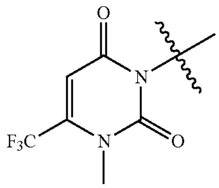 [SMILES: *n1c(=O)cc(C(F)(F)F)n(C)c1=O] | 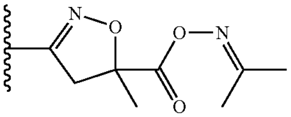 [SMILES: *C1=NOC(C)(C(=O)ON=C(C)C)C1] | Cl | Cl | CH | |
| 163 | 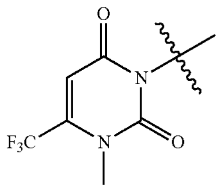 [SMILES: *n1c(=O)cc(C(F)(F)F)n(C)c1=O] | 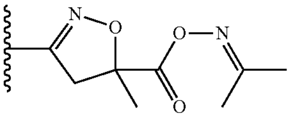 | Cl | OH | CH | |
| 164 | 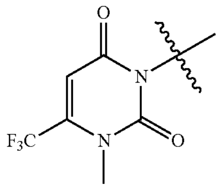 [SMILES: *n1c(=O)cc(C(F)(F)F)n(C)c1=O] | 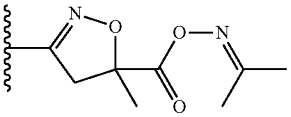 | Br | F | CH | |
| 165 | 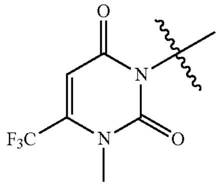 [SMILES: *n1c(=O)cc(C(F)(F)F)n(C)c1=O] | 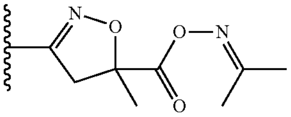 [SMILES: *C1=NOC(C)(C(=O)ON=C(C)C)C1] | $CF_3$ | F | CH | |

TABLE 1-continued
Structures and ¹H NMR data of compounds
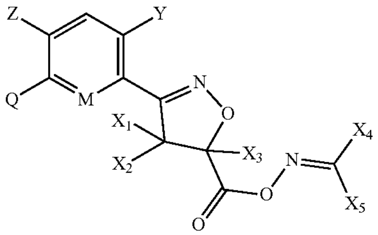
I
| NO. | Q | 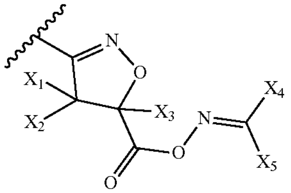 | Y | Z | M | ¹H NMR |
|---|---|---|---|---|---|---|
| 166 | 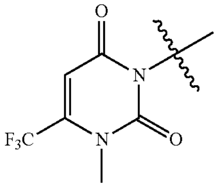 [SMILES: *n1c(=O)cc(C(F)(F)F)n(C)c1=O] | 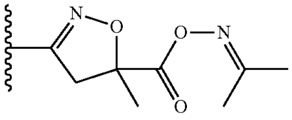 | CN | H | CH | |
| 167 | 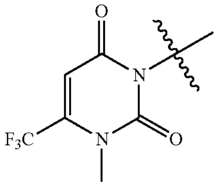 [SMILES: *n1c(=O)cc(C(F)(F)F)n(C)c1=O] | 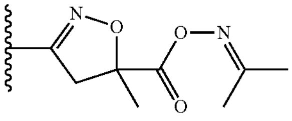 | CN | F | CH | |
| 168 | 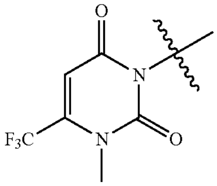 [SMILES: *n1c(=O)cc(C(F)(F)F)n(C)c1=O] | 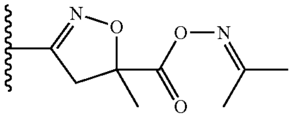 [SMILES: *C1=NOC(C)(C(=O)ON=C(C)C)C1] | $NO_2$ | F | CH | |
| 169 | 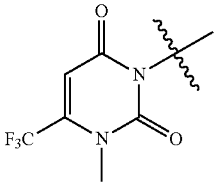 [SMILES: *n1c(=O)cc(C(F)(F)F)n(C)c1=O] | 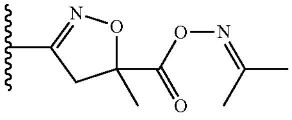 [SMILES: *C1=NOC(C)(C(=O)ON=C(C)C)C1] | $NH_2$ | F | CH | |
| 170 | 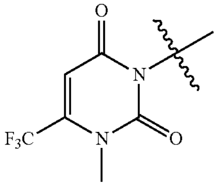 [SMILES: *n1c(=O)cc(C(F)(F)F)n(C)c1=O] | 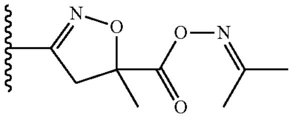 | Cl | F | N | ¹H NMR (500 MHz, Chloroform-d) δ 7.60 (d, J = 8.0 Hz, 1H), 6.08 (s, 1H), 3.82 (s, 3H), 3.05 (d, J = 18.0 Hz, 1H), 2.82 (d, J = 18.0 Hz, 1H), 2.64 (s, 6H), 1.52 (s, 3H). |

TABLE 1-continued
Structures and $^1$H NMR data of compounds
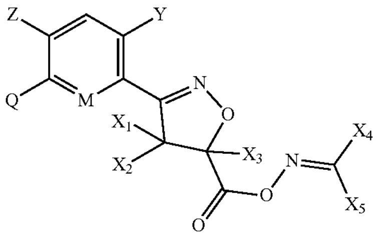
I
| NO. | Q | 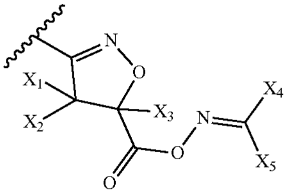 | Y | Z | M | $^1$H NMR |
|---|---|---|---|---|---|---|
| 171 | 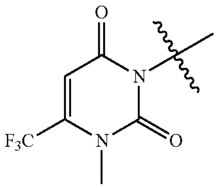 [SMILES: *n1c(=O)cc(C(F)(F)F)n(C)c1=O] | 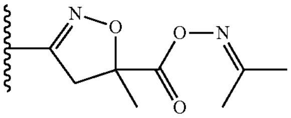 | Cl | H | N | |
| 172 | 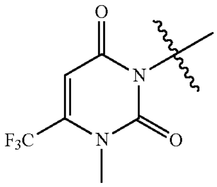 [SMILES: *n1c(=O)cc(C(F)(F)F)n(C)c1=O] | 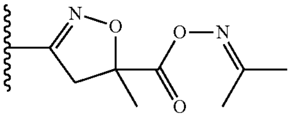 [SMILES: *C1=NOC(C)(C(=O)ON=C(C)C)C1] | CN | H | N | |
| 173 | 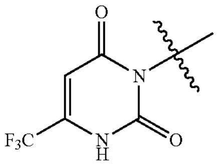 [SMILES: *n1c(=O)cc(C(F)(F)F)[nH]c1=O] | 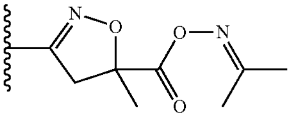 [SMILES: *C1=NOC(C)(C(=O)ON=C(C)C)C1] | Cl | F | CH | |
| 174 | 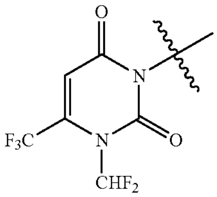 [SMILES: *n1c(=O)cc(C(F)(F)F)n(C(F)F)c1=O] | 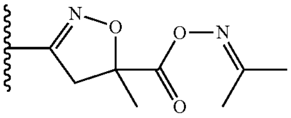 [SMILES: *C1=NOC(C)(C(=O)ON=C(C)C)C1] | Cl | F | CH | |
| 175 | 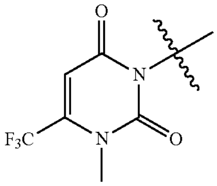 [SMILES: *n1c(=O)cc(C(F)(F)F)n(C)c1=O] | 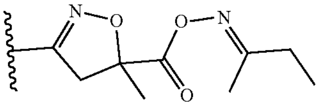 [SMILES: *C1=NOC(C)(C(=O)O/N=C(\C)CC)C1] | Cl | F | CH | |

TABLE 1-continued
Structures and $^1$H NMR data of compounds
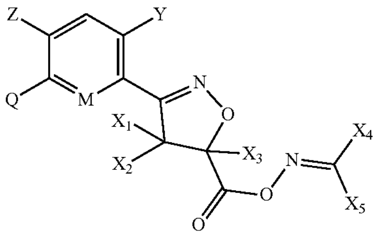
I
| NO. | Q | 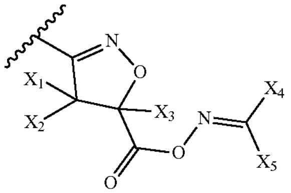 | Y | Z | M | $^1$H NMR |
|---|---|---|---|---|---|---|
| 176 | 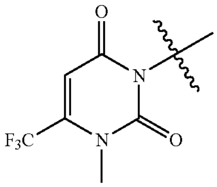 [SMILES: *n1c(=O)cc(C(F)(F)F)n(C)c1=O] | 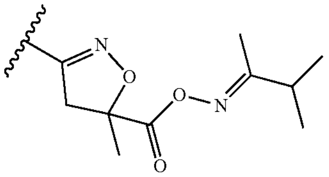 [SMILES: *C1=NOC(C)(C(=O)O/N=C(\C)C(C)C)C1] | Cl | F | CH | |
| 177 | 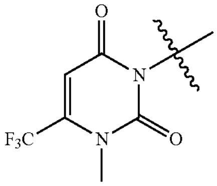 [SMILES: *n1c(=O)cc(C(F)(F)F)n(C)c1=O] | 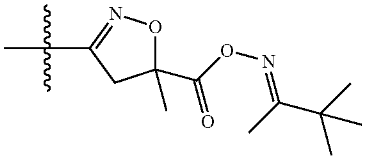 [SMILES: *C1=NOC(C)(C(=O)O/N=C(\C)C(C)(C)C)C1] | Cl | F | CH | |
| 178 | 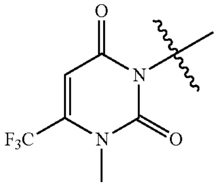 [SMILES: *n1c(=O)cc(C(F)(F)F)n(C)c1=O] | 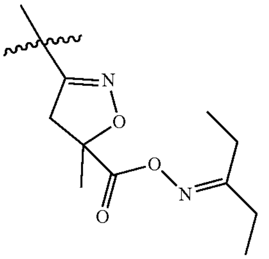 [SMILES: *C1=NOC(C)(C(=O)ON=C(CC)CC)C1] | Cl | F | CH | |
| 179 | 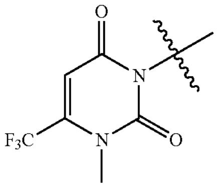 [SMILES: *n1c(=O)cc(C(F)(F)F)n(C)c1=O] | 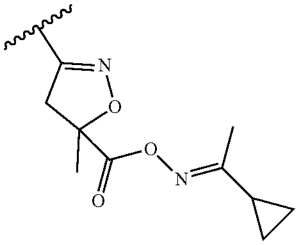 [SMILES: *C1=NOC(C)(C(=O)O/N=C(\C)C2CC2)C1] | Cl | F | CH | |
| 180 | 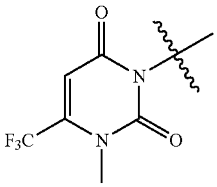 [SMILES: *n1c(=O)cc(C(F)(F)F)n(C)c1=O] | 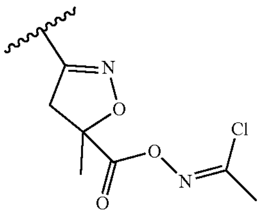 [SMILES: *C1=NOC(C)(C(=O)O/N=C(/C)Cl)C1] | Cl | F | CH | |

TABLE 1-continued
Structures and $^{1}H$ NMR data of compounds
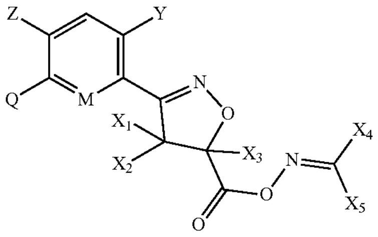
I
| NO. | Q | 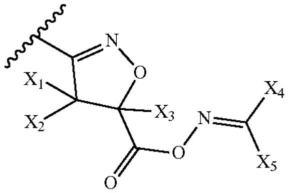 | Y | Z | M | $^{1}H$ NMR |
|---|---|---|---|---|---|---|
| 181 | 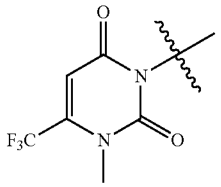 [SMILES: *n1c(=O)cc(C(F)(F)F)n(C)c1=O] | 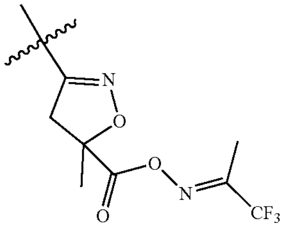 [SMILES: *C1=NOC(C)(C(=O)O/N=C(\C)C(F)(F)F)C1] | Cl | F | CH | |
| 182 | 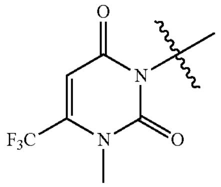 [SMILES: *n1c(=O)cc(C(F)(F)F)n(C)c1=O] | 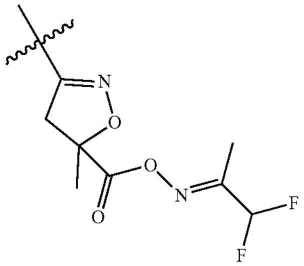 [SMILES: *C1=NOC(C)(C(=O)O/N=C(\C)C(F)F)C1] | Cl | F | CH | |
| 183 | 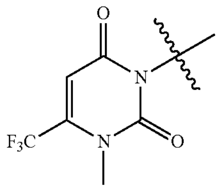 [SMILES: *n1c(=O)cc(C(F)(F)F)n(C)c1=O] | 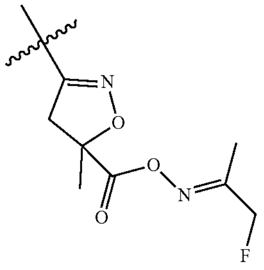 [SMILES: *C1=NOC(C)(C(=O)O/N=C(\C)CF)C1] | Cl | F | CH | |
| 184 | 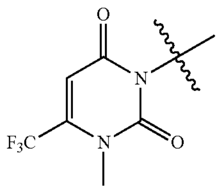 [SMILES: *n1c(=O)cc(C(F)(F)F)n(C)c1=O] | 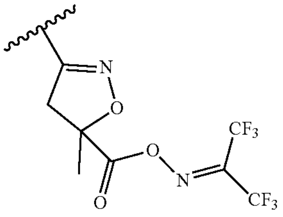 [SMILES: *C1=NOC(C)(C(=O)ON=C(C(F)(F)F)C(F)(F)F)C1] | Cl | F | CH | |

TABLE 1-continued
Structures and $^1$H NMR data of compounds
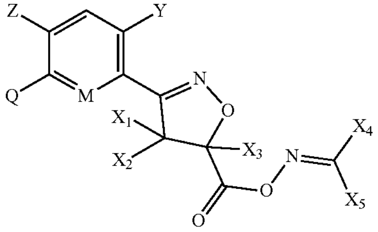
I
| NO. | Q | 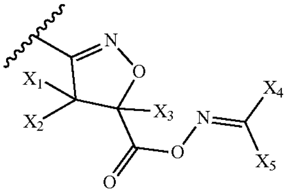 | Y | Z | M | $^1$H NMR |
|---|---|---|---|---|---|---|
| 185 | 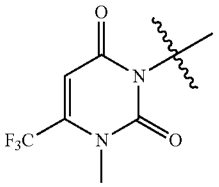 [SMILES: *n1c(=O)cc(C(F)(F)F)n(C)c1=O] | 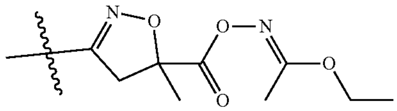 [SMILES: *C1=NOC(C)(C(=O)O/N=C(\C)OCC)C1] | Cl | F | CH | |
| 186 | 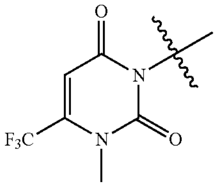 [SMILES: *n1c(=O)cc(C(F)(F)F)n(C)c1=O] | 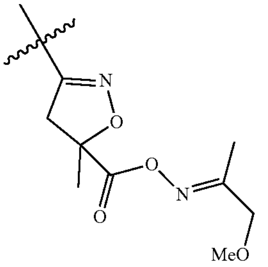 [SMILES: *C1=NOC(C)(C(=O)O/N=C(\C)COC)C1] | Cl | F | CH | |
| 187 | 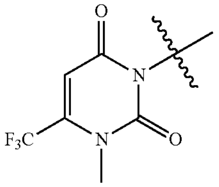 [SMILES: *n1c(=O)cc(C(F)(F)F)n(C)c1=O] | 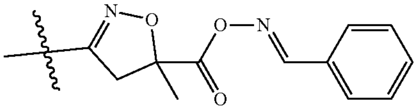 [SMILES: *C1=NOC(C)(C(=O)O/N=C/c2ccccc2)C1] | Cl | F | CH | |
| 188 | 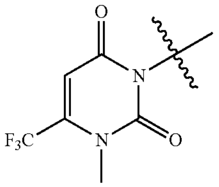 [SMILES: *n1c(=O)cc(C(F)(F)F)n(C)c1=O] | 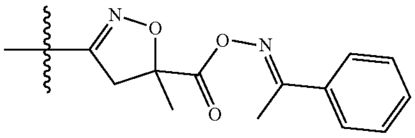 [SMILES: *C1=NOC(C)(C(=O)O/N=C(\C)c2ccccc2)C1] | Cl | F | CH | |
| 189 | 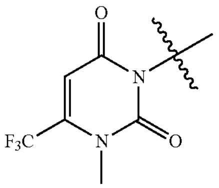 [SMILES: *n1c(=O)cc(C(F)(F)F)n(C)c1=O] | 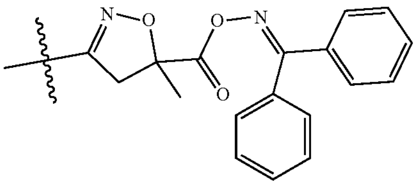 [SMILES: *C1=NOC(C)(C(=O)ON=C(c2ccccc2)c2ccccc2)C1] | Cl | F | CH | |

TABLE 1-continued
Structures and $^1$H NMR data of compounds
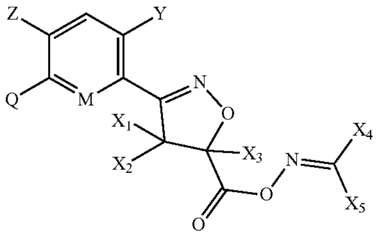
I
| NO. | Q | 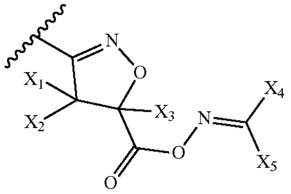 | Y | Z | M | $^1$H NMR |
|---|---|---|---|---|---|---|
| 190 | 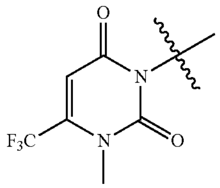 [SMILES: *n1c(=O)cc(C(F)(F)F)n(C)c1=O] | 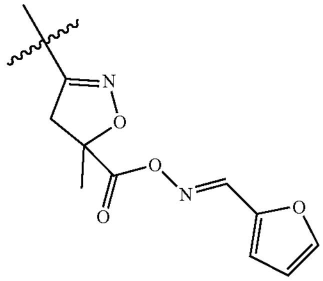 [SMILES: *C1=NOC(C)(C(=O)O/N=C/c2ccco2)C1] | Cl | F | CH | |
| 191 | 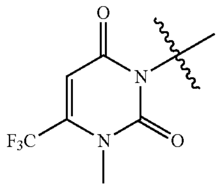 [SMILES: *n1c(=O)cc(C(F)(F)F)n(C)c1=O] | 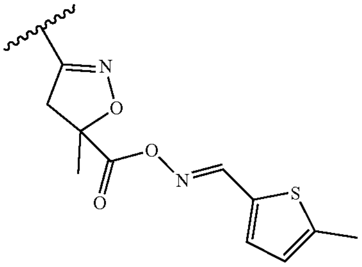 [SMILES: *C1=NOC(C)(C(=O)O/N=C/c2ccc(C)s2)C1] | Cl | F | CH | |
| 192 | 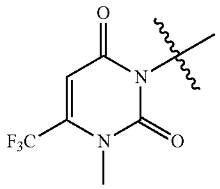 [SMILES: *n1c(=O)cc(C(F)(F)F)n(C)c1=O] | 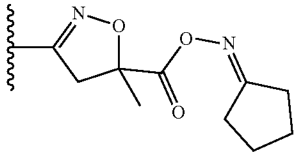 [SMILES: *C1=NOC(C)(C(=O)ON=C2CCCC2)C1] | Cl | F | CH | |
| 193 | 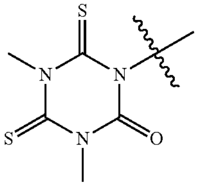 | 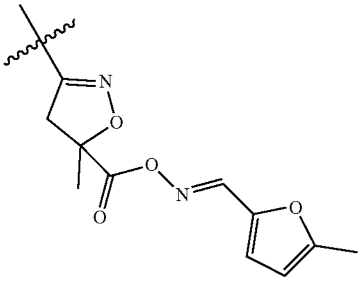 [SMILES: *C1=NOC(C)(C(=O)O/N=C/c2ccc(C)o2)C1] | Cl | F | CH | |

TABLE 1-continued
Structures and $^{1}$H NMR data of compounds
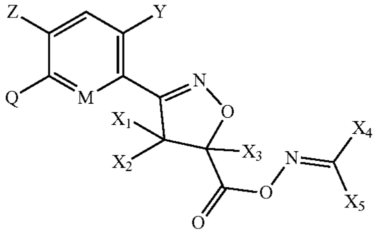
I
| NO. | Q | 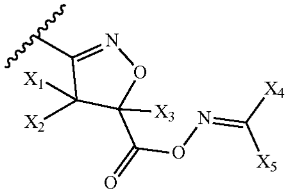 | Y | Z | M | $^{1}$H NMR |
|---|---|---|---|---|---|---|
| 194 | 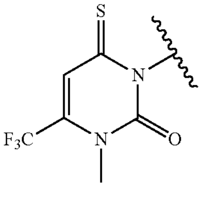 [SMILES: *n1c(=S)cc(C(F)(F)F)n(C)c1=O] | 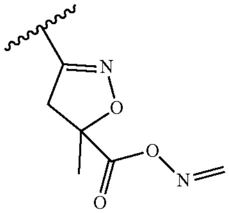 [SMILES: *C1=NOC(C)(C(=O)ON=C)C1] | Cl | F | CH | |
| 195 | 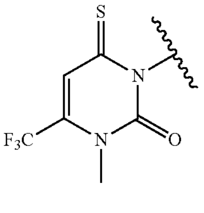 [SMILES: *n1c(=S)cc(C(F)(F)F)n(C)c1=O] | 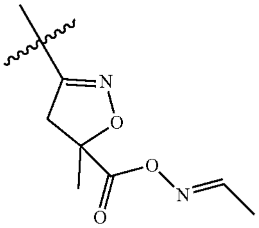 [SMILES: *C1=NOC(C)(C(=O)O/N=C/C)C1] | Cl | F | CH | |
| 196 | 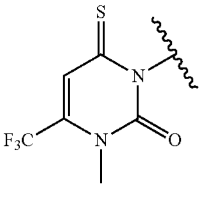 [SMILES: *n1c(=S)cc(C(F)(F)F)n(C)c1=O] | 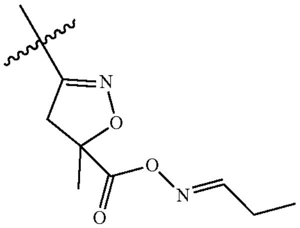 [SMILES: *C1=NOC(C)(C(=O)O/N=C/CC)C1] | Cl | F | CH | |
| 197 | 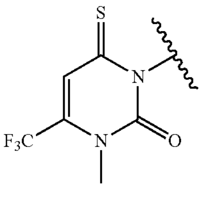 [SMILES: *n1c(=S)cc(C(F)(F)F)n(C)c1=O] | 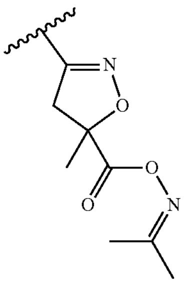 [SMILES: *C1=NOC(C)(C(=O)ON=C(C)C)C1] | Cl | F | CH | $^{1}$H NMR (500 MHz, Chloroform-d) δ 7.30 (d, J = 9.0 Hz, 1H), 6.96 (d, J = 8.0 Hz, 1H), 6.39 (s, 1H), 3.86 (s, 3H), 3.33 (d, J = 18.0 Hz, 1H), 3.08 (d, J = 18.0 Hz, 1H), 2.61 (s, 6H), 1.65 (s, 3H). |

TABLE 1-continued
Structures and $^1$H NMR data of compounds
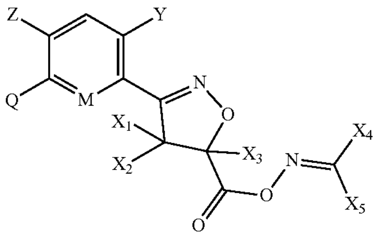
I
| NO. | Q | 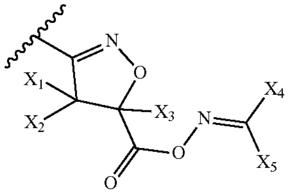 | Y | Z | M | $^1$H NMR |
|---|---|---|---|---|---|---|
| 198 | 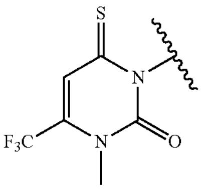 [SMILES: *n1c(=S)cc(C(F)(F)F)n(C)c1=O] | 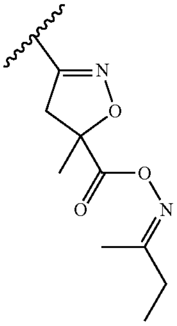 [SMILES: *C1=NOC(C)(C(=O)O/N=C(\C)CC)C1] | Cl | F | CH | |
| 199 | 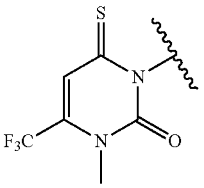 [SMILES: *n1c(=S)cc(C(F)(F)F)n(C)c1=O] | 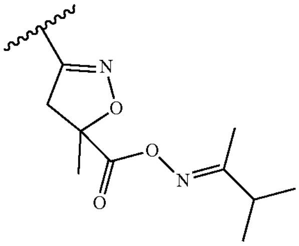 [SMILES: *C1=NOC(C)(C(=O)O/N=C(\C)C(C)C)C1] | Cl | F | CH | |
| 200 | 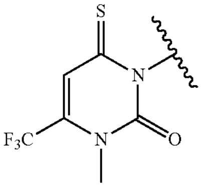 [SMILES: *n1c(=S)cc(C(F)(F)F)n(C)c1=O] | 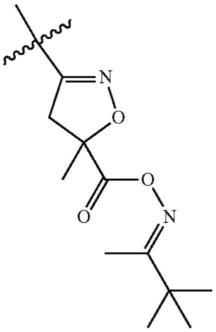 [SMILES: *C1=NOC(C)(C(=O)O/N=C(\C)C(C)(C)C)C1] | Cl | F | CH | |

TABLE 1-continued
Structures and ¹H NMR data of compounds
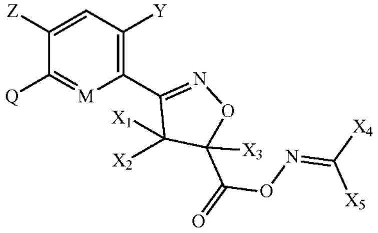
I
| NO. | Q | 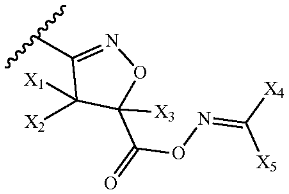 | Y | Z | M | $^1H$ NMR |
|---|---|---|---|---|---|---|
| 201 | 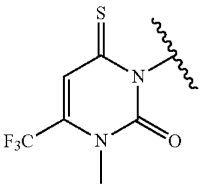 [SMILES: *n1c(=S)cc(C(F)(F)F)n(C)c1=O] | 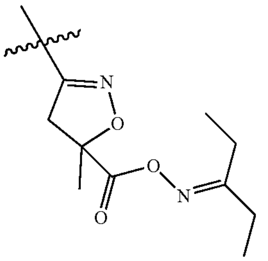 [SMILES: *C1=NOC(C)(C(=O)ON=C(CC)CC)C1] | Cl | F | CH | |
| 202 | 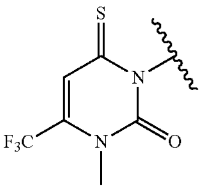 [SMILES: *n1c(=S)cc(C(F)(F)F)n(C)c1=O] | 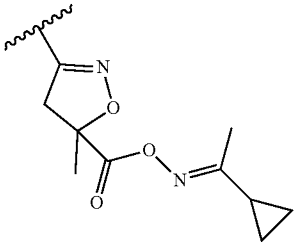 [SMILES: *C1=NOC(C)(C(=O)O/N=C(\C)C2CC2)C1] | Cl | F | CH | |
| 203 | 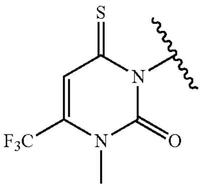 [SMILES: *n1c(=S)cc(C(F)(F)F)n(C)c1=O] | 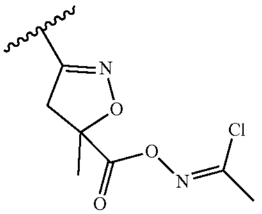 [SMILES: *C1=NOC(C)(C(=O)O/N=C(/C)Cl)C1] | Cl | F | CH | |
| 204 | 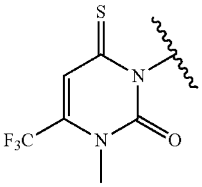 [SMILES: *n1c(=S)cc(C(F)(F)F)n(C)c1=O] | 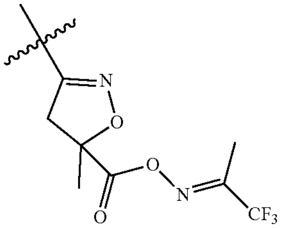 [SMILES: *C1=NOC(C)(C(=O)O/N=C(\C)C(F)(F)F)C1] | Cl | F | CH | |

TABLE 1-continued
Structures and ¹H NMR data of compounds
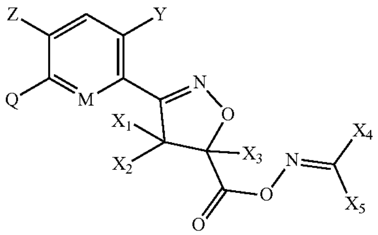
I
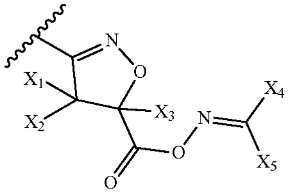
| NO. | Q | | Y | Z | M | ¹H NMR |
|---|---|---|---|---|---|---|
| 205 | 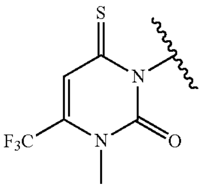 [SMILES: *n1c(=S)cc(C(F)(F)F)n(C)c1=O] | 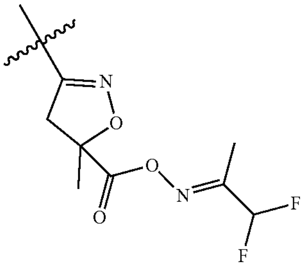 [SMILES: *C1=NOC(C)(C(=O)O/N=C(\C)C(F)F)C1] | Cl | F | CH | |
| 206 | 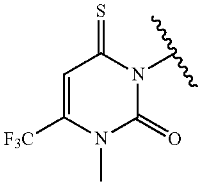 [SMILES: *n1c(=S)cc(C(F)(F)F)n(C)c1=O] | 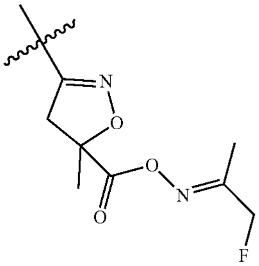 [SMILES: *C1=NOC(C)(C(=O)O/N=C(\C)CF)C1] | Cl | F | CH | |
| 207 | 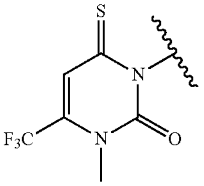 [SMILES: *n1c(=S)cc(C(F)(F)F)n(C)c1=O] | 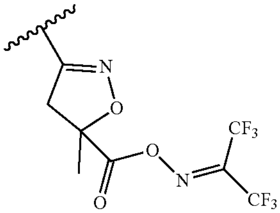 [SMILES: *C1=NOC(C)(C(=O)ON=C(C(F)(F)F)C(F)(F)F)C1] | Cl | F | CH | |
| 208 | 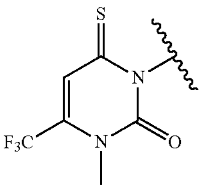 [SMILES: *n1c(=S)cc(C(F)(F)F)n(C)c1=O] | 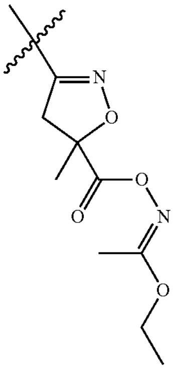 [SMILES: *C1=NOC(C)(C(=O)O/N=C(\C)OCC)C1] | Cl | F | CH | |

TABLE 1-continued
Structures and $^1H$ NMR data of compounds
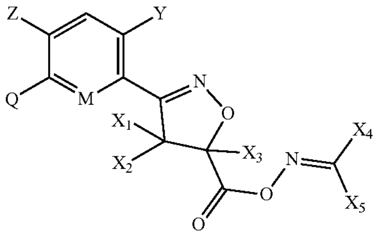
I
| NO. | Q | 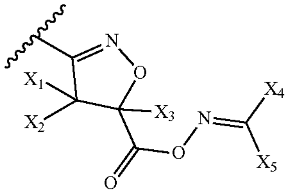 | Y | Z | M | $^1H$ NMR |
|---|---|---|---|---|---|---|
| 209 | 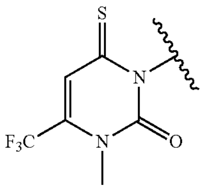 [SMILES: *n1c(=S)cc(C(F)(F)F)n(C)c1=O] | 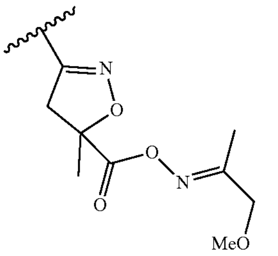 [SMILES: *C1=NOC(C)(C(=O)O/N=C(\C)COC)C1] | Cl | F | CH | |
| 210 | 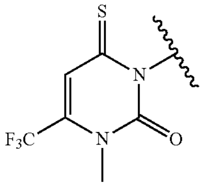 [SMILES: *n1c(=S)cc(C(F)(F)F)n(C)c1=O] | 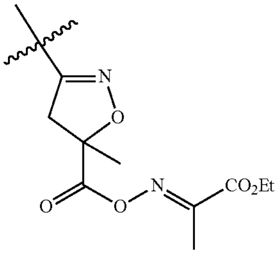 [SMILES: *C1=NOC(C)(C(=O)O/N=C(\C)C(=O)OCC)C1] | Cl | F | CH | |
| 211 | 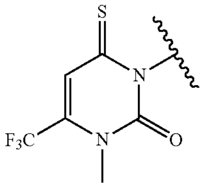 [SMILES: *n1c(=S)cc(C(F)(F)F)n(C)c1=O] | 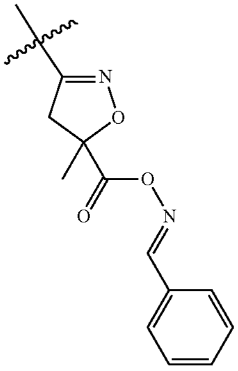 [SMILES: *C1=NOC(C)(C(=O)O/N=C/c2ccccc2)C1] | Cl | F | CH | |

TABLE 1-continued
Structures and $^1$H NMR data of compounds
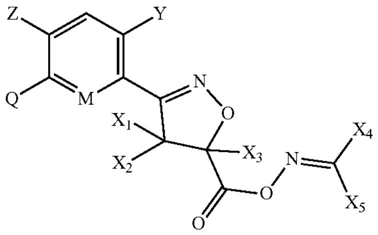
I
| NO. | Q | 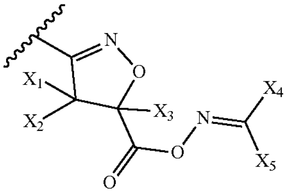 | Y | Z | M | $^1$H NMR |
|---|---|---|---|---|---|---|
| 212 | 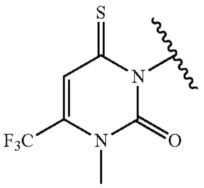 [SMILES: *n1c(=S)cc(C(F)(F)F)n(C)c1=O] | 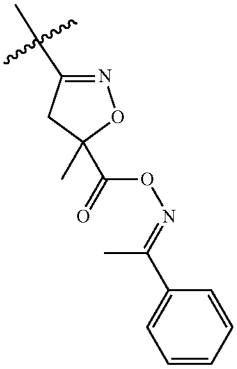 [SMILES: *C1=NOC(C)(C(=O)O/N=C(\C)c2ccccc2)C1] | Cl | F | CH | |
| 213 | 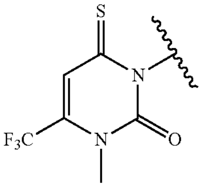 [SMILES: *n1c(=S)cc(C(F)(F)F)n(C)c1=O] | 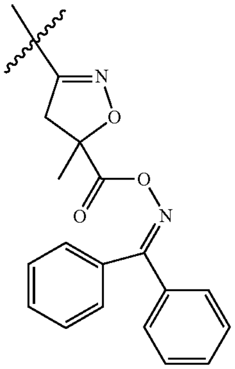 [SMILES: *C1=NOC(C)(C(=O)ON=C(c2ccccc2)c2ccccc2)C1] | Cl | F | CH | |
| 214 | 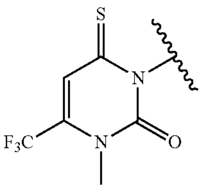 [SMILES: *n1c(=S)cc(C(F)(F)F)n(C)c1=O] | 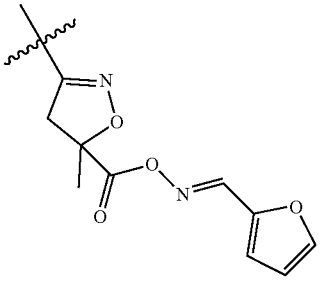 [SMILES: *C1=NOC(C)(C(=O)O/N=C/c2ccco2)C1] | Cl | F | CH | |

TABLE 1-continued
Structures and $^1$H NMR data of compounds
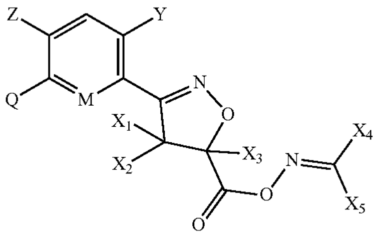
I
| NO. | Q | 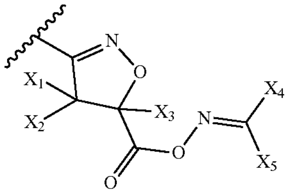 | Y | Z | M | $^1$H NMR |
|---|---|---|---|---|---|---|
| 215 | 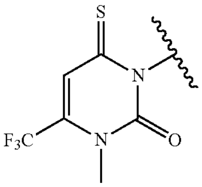 [SMILES: *n1c(=S)cc(C(F)(F)F)n(C)c1=O] | 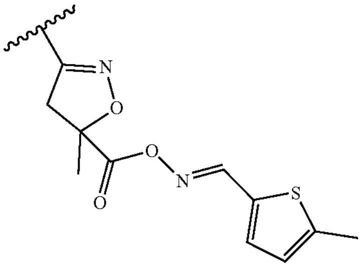 [SMILES: *C1=NOC(C)(C(=O)O/N=C/c2ccc(C)s2)C1] | Cl | F | CH | |
| 216 | 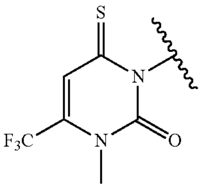 [SMILES: *n1c(=S)cc(C(F)(F)F)n(C)c1=O] | 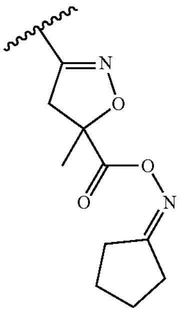 [SMILES: *C1=NOC(C)(C(=O)ON=C2CCCC2)C1] | Cl | F | CH | |
| 217 | 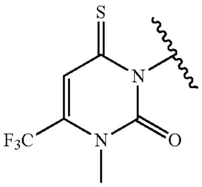 [SMILES: *n1c(=S)cc(C(F)(F)F)n(C)c1=O] | 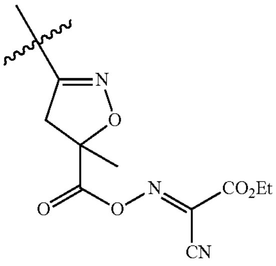 [SMILES: *C1=NOC(C)(C(=O)O/N=C(\C#N)C(=O)OCC)C1] | Cl | F | CH | |
| 218 | 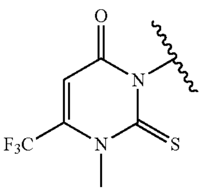 [SMILES: *n1c(=O)cc(C(F)(F)F)n(C)c1=S] | 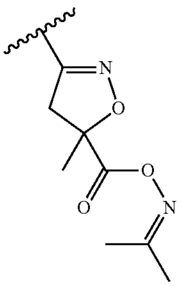 [SMILES: *C1=NOC(C)(C(=O)ON=C(C)C)C1] | Cl | F | CH | $^1$H NMR (500 MHz, Chloroform-d) δ 7.33 (d, J = 9.0 Hz, 1H), 7.06 (d, J = 8.0 Hz, 1H), 6.49 (s, 1H), 4.21 (s, 3H), 3.39 (d, J = 18.0 Hz, 1H), 3.05 (d, J = 18.0 Hz, 1H), 2.63 (s, 6H), 1.62 (s, 3H). |

TABLE 1-continued

Structures and $^1$H NMR data of compounds

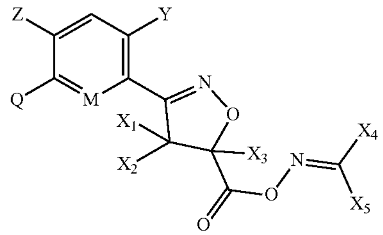

I

| NO. | Q | 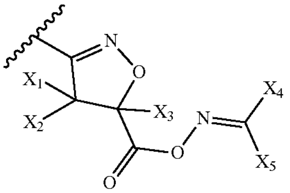 | Y | Z | M | $^1$H NMR |
|---|---|---|---|---|---|---|
| 219 | 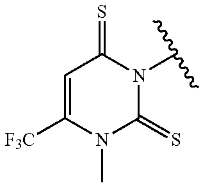 [SMILES: *n1c(=S)cc(C(F)(F)F)n(C)c1=S] | 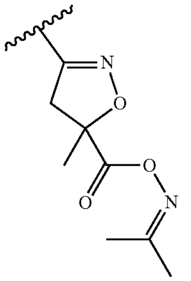 [SMILES: *C1=NOC(C)(C(=O)ON=C(C)C)C1] | Cl | F | CH | |

The method for preparing the compound of the invention will be explained in detail in the following program and embodiment. The material is commercial available or prepared through known method reported in the literature or shown in the route. Those skilled in the art should understand that the compound of the invention can also be synthesized by other synthetic route. Although the detailed material and reaction condition in the synthetic route have been explicated in the following text, it is still easy to be replaced by other similar material and condition. Isomer of the compound, for example, that produced with the variation of the preparation method of the present invention is included in the scope of the present invention. In addition, the following preparation method can be further modified according to the disclosures of the present invention by using common chemical method known to those skilled in the art, for example, protection of suitable group in the process of the reaction, etc.

The following method of application can be used to improve further understanding of the preparation method of the present invention. The specific material, class and condition have been determined to be further explication of the present invention, not to be any limit of the reasonable scope thereof. Reagents of the following synthetic compound showed in the table can either be purchased from the market or easily prepared by those skilled in the art.

Examples of representative compounds are as follows, the synthesis methods of other compounds are similar, and will not be described in detail here.

1. Synthesis of Compound 10

1) 10-1 (20 g, 98.3 mmol, 1.0 eq) was added to 200 ml of EtOH, then $NH_2OH$ HCl (7.5 g, 108.1 mmol, 1.1 eq) aqueous solution (30 ml) was added dropwise to the reaction solution at 0° C. After the dropwise addition was completed, the reaction solution was stirred at 0° C. for 3 hours. When the raw material was almost completely reacted by LCMS detection, a major new peak emerged. The reaction solution was concentrated to remove part of ethanol, then poured into 100 ml of water, the solid was precipitated, filtered, the filter cake was washed with water, then dried to produce 10-2 (20 g, 93% yield) (white solid).

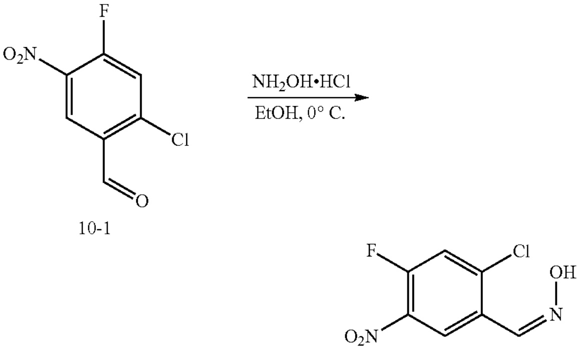

10-1

10-2

2) 10-2 (20 g, 91.5 mmol, 1.0 eq) was added to 150 ml of DMF, then NCS (13.4 g, 100.7 mmol, 1.1 eq) was slowly added to the reaction solution at 35° C. After the addition was completed, the reaction solution was stirred at 35° C. for 1.5 hours. The raw material was almost completely reacted by LCMS detection. The reaction solution was poured into 100 ml of HCl (1M), then extracted by adding dichloromethane. The organic phase was washed with saturated brine (100 ml*3), then concentrated to produce crude product 10-3 (26 g, crude product) (yellow oily). Such crude product was directly used in the next step.

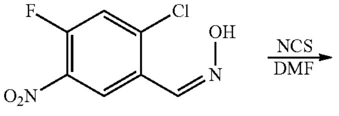

10-2

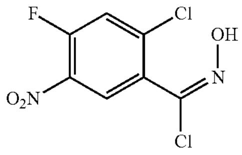

10-3

3) 10-3 (26 g) and $Et_3N$ (15.6 g, 154.1 mmol, 1.5 eq) were added to 200 ml of DCM. Then, the reaction solution was added with 10-4 (14.1 g, 123.3 mmol, 1.2 eq) at 0° C. The product was detected by LCMS detection after the reaction solution was reacted at 0° C. for 1 hour. The reaction solution was added with 100 ml of water and extracted with dichloromethane (100 ml*3). The organic phase was dried with anhydrous sodium sulfate and concentrated. The crude product was purified by column chromatography to produce 10-5 (17 g, 50% yield) (yellow solid.

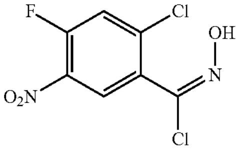

10-3

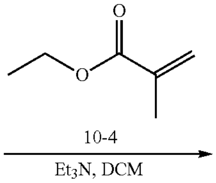

10-4

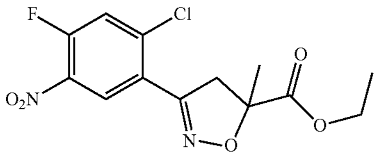

10-5

4) 10-5 (17 g, 51.4 mmol, 1.0 eq), Fe powder (8.6 g, 154.2 mmol, 3 eq), $NH_4Cl$ (5.5 g, 102.8 mmol, 2 eq) and water (50 ml) were added to 200 ml of EtOH in sequence. After the reaction solution was reacted at 80° C. for 2 hours, the raw material disappeared by LCMS detection, and the principal peak was the product peak. The reaction solution was filtered with diatomite, then concentrated to remove ethanol and added with water (100 ml), extracted with ethyl acetate, then concentrated to produce black crude product. Such crude product was separated and purified by column chromatography to produce 10-6 (12 g, 76.6% yield) (yellow solid).

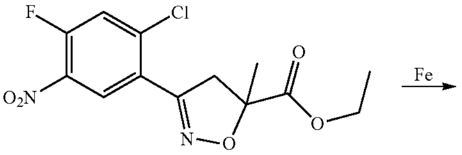

10-5

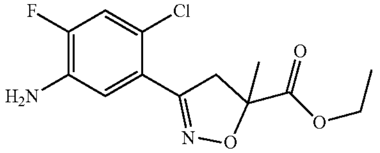

10-6

5) 10-6 (0.6 g, 2.0 mmol, 1.0 eq) and phenyl chloroformate (0.34 g, 2.2 mmol, 1.1 eq) were added to 10 ml of toluene, then the reaction solution was heated at 110° C. for 1 hour. The raw material was almost completely reacted by LCMS detection, and the principal peak belonged to the product. The solvent was concentrated and the crude product was separated by column chromatography to produce 10-7 (0.7 g, 83.4% yield) (white solid).

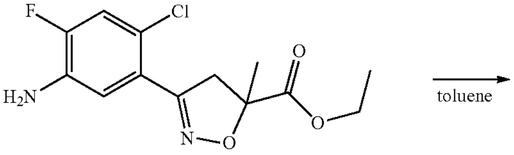

10-6

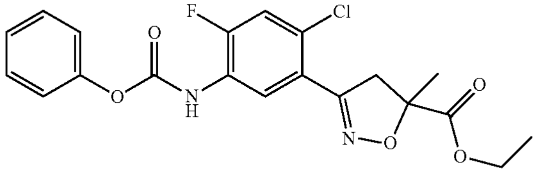

10-7

6) a (0.48 g, 2.1 mmol, 1.5 eq) and AcONa (58 mg, 0.7 mmol, 0.5 eq) were added to 10 ml of DMF. Then, the reaction solution was added with 10-7 (0.6 g, 1.4 mmol, 1.0 eq) at 60° C., and reacted at 60° C. for 1 hour. The product was detected by LCMS detection. The reaction solution was added with 10 ml of water, then extracted with ethyl acetate. After the organic phase was washed with saturated salt brine (20 ml*1) and concentrated, the crude product was separated by column chromatography to produce 10-8 (0.4 g, 61.4% yield) (white solid).

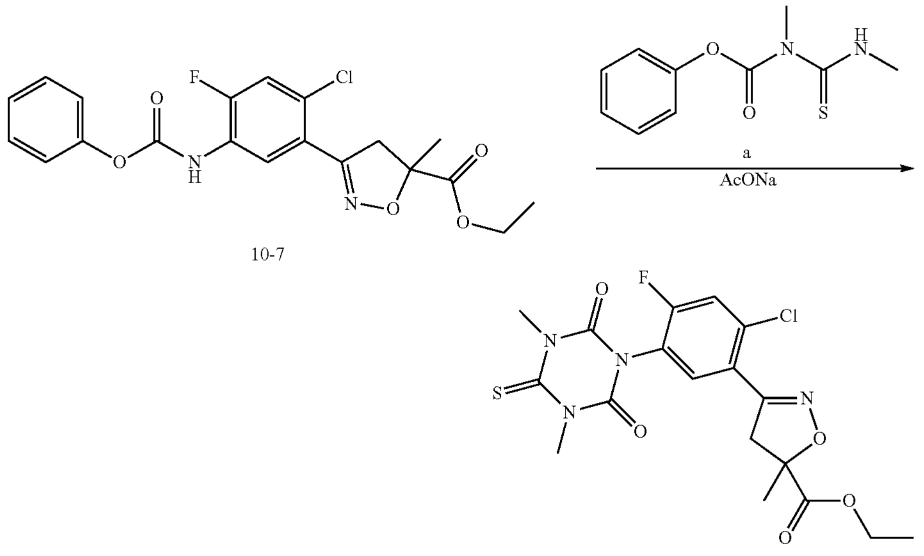

10-7

10-8

7) 10-8 (10 g, 21.9 mmol, 1.0 eq) and HBr (50 ml) were added to 50 ml of 1,4-dioxane, then the reaction solution was reacted at 80° C. for 6 hours. The product was detected by LCMS detection. The reaction solution was added with 50 ml of water, then extracted with ethyl acetate (50 ml*3). The organic phase was dried with anhydrous sodium sulfate, then concentrated to produce 10-9 (8.5 g, 90.6% yield) (yellow solid).

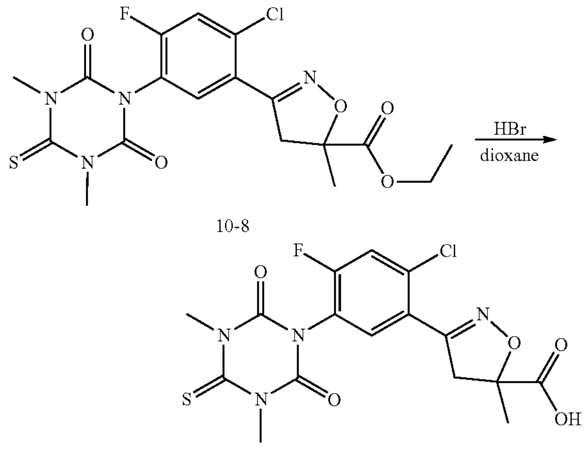

10-8

10-9

8) 10-9 (0.5 g, 1.17 mmol, 1.0 eq), b (0.10 g, 1.40 mmol, 1.2 eq), $Et_3N$ (0.14 g, 1.40 mmol, 1.2 eq) and PyBOP (0.67 g, 1.28 mmol, 1.1 eq) were added to 8 ml of DCM in sequence. After the reaction solution was reacted at 25° C. for 2 hours, the raw material disappeared by LCMS detection, and the principal peak was the product peak. The reaction solution was added with 10 ml of water and extracted with dichloromethane (10 ml*2). The organic phase was dried with anhydrous sodium sulfate, then concentrated to produce crude product. Such crude product was separated and purified by column chromatography to produce compound 10 (0.47 g, 83.3% yield) (yellow solid).

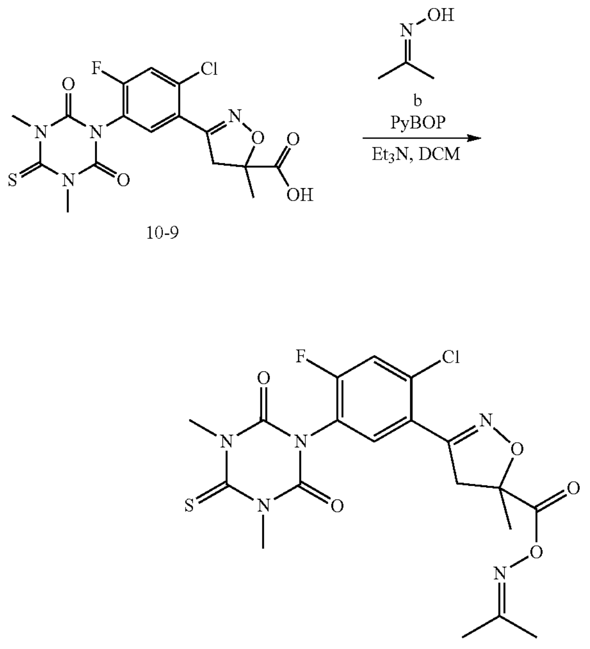

10-9

10

2. Synthesis of Compound 124

Compound 10-9 was prepared by referring to the above method. 10-9 (0.5 g, 1.17 mmol, 1.0 eq), c (0.19 g, 1.40 mmol, 1.2 eq), $Et_3N$ (0.14 g, 1.40 mmol, 1.2 eq) and PyBOP (0.67 g, 1.28 mmol, 1.1 eq) were added into 8 ml of DCM in sequence. After reaction solution was reacted at 25° C. for 2 hours, the raw material disappeared by LCMS detection, and the principal peak was the product peak. The reaction solution was added with 10 ml of water, then extracted with dichloromethane (10 ml*2). The organic phase was dried with anhydrous sodium sulfate, then concentrated to produce crude product. Such crude product was separated and purified by column chromatography to produce compound 124 (0.50 g, 78.5% yield) (yellow solid).

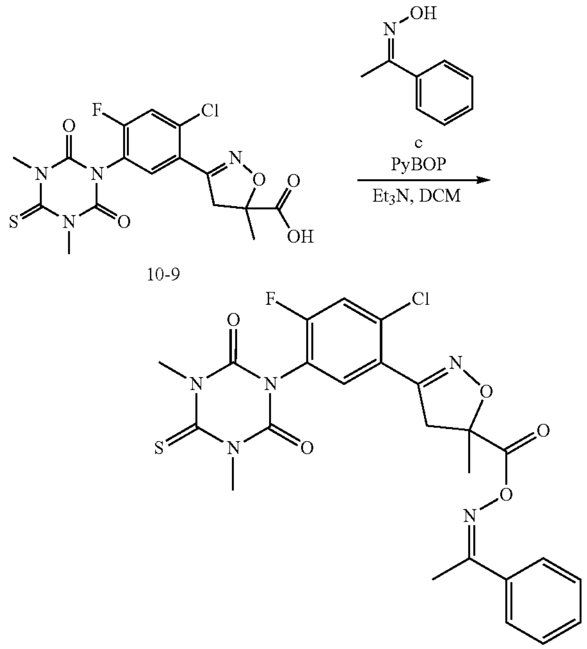

10-9

124

Biological Activity Evaluation:

The activity level criteria for plant damage (i.e., growth control rate) are as follows:

Level 5: growth control rate is above 85%;

Level 4: growth control rate is greater than or equal to 60% and less than 85%;

Level 3: growth control rate is greater than or equal to 40% and less than 60%;

Level 2: growth control rate is greater than or equal to 20% and less than 40%;

Level 1: growth control rate is greater than or equal to 5% and less than 20%;

Level 0: growth control rate is less than 5%.

The above growth control rates are fresh weight control rates.

Experiment on Weeding Effect in Post-Emergence Stage:

Monocotyledonous and dicotyledonous weed seeds (*Descurainia sophia, Capsella bursa-pastoris, Abutilon theophrasti, Galium aparine, Stellaria media, Lithospermum arvense, Rorippa indica, Alopecurus aequalis, Alopecurus japonicus, Beckmannia syzigachne, Sclerochloa dura, Conyza Canadensis, Phleum paniculatum, Veronica didyma Tenore, Eleusine indica, Bromus japonicus, Aegilops tauschii, Phalaris arundinacea, Amaranthus retroflexus, Chenopodium album, Commelina communis, Sonchus arvensis, Convolvulus arvensis, Cirsium setosum, Solanum nigrum, Acalypha australis, Digitaria sanguinalis, Echinochloa crusgalli, Setaria viridis, Setaria glauca, Leptochloa chinensis, Monochoria vaginalis, Sagittaria trolia, Scirpus juncoides, Cyperus rotundus, Cyperus iria, Cyperus difformis, Elmbristylis, Portulaca oleracea, Xanthium sibiricum, Pharbitis nil*) and major crop seeds (wheat, corn, rice, soybean, cotton, oilseed rape, millet, sorghum, potato, sesame, ricinus) were placed in plastic pots filled with soil, then covered with 0.5-2 cm of soil, allowed to grow in a good greenhouse environment. After 2 weeks of sowing, the test plants were treated in the 2-3 leaf stage. The tested compounds of the present invention were respectively dissolved in acetone, then added with Tween 80 and 1.5 liter/ha of emulsifiable concentrate of methyl oleate as synergist, diluted with a certain amount of water to obtain a solution with a certain concentration, and sprayed with a spray tower onto the plants. After the application, the plants were cultured for 3 weeks in the greenhouse, and then the experimental results of the weeding were counted. The doses of the used compounds were 500, 250, 125, 60, 15 g a.i./ha, and the averages were obtained by repeating for three times. Representative data are listed in Table 2.

TABLE 2

Results on weeding effect in post-emergence stage

| Compound No. | *Echinochloa crusgalli* | *Digitaria sanguinalis* | *Setaria viridis* | *Leptochloa chinensis* | *Eleusine indica* | *Veronica didyma Tenore* | *Galium aparine* | *Abutilon theophrasti* | *Amaranthus retroflexus* | Dose (g a.i./ha) |
|---|---|---|---|---|---|---|---|---|---|---|
| 2 | 5 | 5 | 5 | 5 | 5 | 5 | 5 | 5 | 5 | 15 |
| 10 | 5 | 5 | 5 | 5 | 5 | 5 | 5 | 5 | 5 | 15 |
| 16 | 5 | 5 | 5 | 5 | 5 | 5 | 5 | 5 | 5 | 15 |
| 54 | 5 | 5 | 5 | 5 | 5 | 5 | 5 | 5 | 5 | 15 |
| 56 | 5 | 5 | 5 | 5 | 5 | 5 | 5 | 5 | 5 | 15 |
| 57 | 5 | 5 | 5 | 5 | 5 | 5 | 5 | 5 | 5 | 15 |
| 58 | 5 | 5 | 5 | 5 | 5 | 5 | 5 | 5 | 5 | 15 |
| 59 | 5 | 5 | 5 | 5 | 5 | 5 | 5 | 5 | 5 | 15 |
| 60 | 5 | 5 | 5 | 5 | 5 | 5 | 5 | 5 | 5 | 15 |
| 61 | 5 | 5 | 5 | 5 | 5 | 5 | 5 | 5 | 5 | 15 |
| 67 | 5 | 5 | 5 | 5 | 5 | 5 | 5 | 5 | 5 | 15 |
| 68 | 5 | 5 | 5 | 5 | 5 | 5 | 5 | 5 | 5 | 15 |
| 69 | 5 | 5 | 5 | 5 | 5 | 5 | 5 | 5 | 5 | 15 |
| 70 | 5 | 5 | 5 | 5 | 5 | 5 | 5 | 5 | 5 | 15 |
| 71 | 5 | 5 | 5 | 5 | 5 | 5 | 5 | 5 | 5 | 15 |
| 74 | 5 | 5 | 5 | 5 | 5 | 5 | 5 | 5 | 5 | 15 |
| 75 | 5 | 5 | 5 | 5 | 5 | 5 | 5 | 5 | 5 | 15 |
| 79 | 5 | 5 | 5 | 5 | 5 | 5 | 5 | 5 | 5 | 15 |
| 80 | 5 | 5 | 5 | 5 | 5 | 5 | 5 | 5 | 5 | 15 |
| 81 | 5 | 5 | 5 | 5 | 5 | 5 | 5 | 5 | 5 | 15 |
| 83 | 5 | 5 | 5 | 5 | 5 | 5 | 5 | 5 | 5 | 15 |
| 84 | 5 | 5 | 5 | 5 | 5 | 5 | 5 | 5 | 5 | 15 |
| 90 | 5 | 5 | 5 | 5 | 5 | 5 | 5 | 5 | 5 | 15 |
| 117 | 5 | 5 | 5 | 5 | 5 | 5 | 5 | 5 | 5 | 15 |
| 118 | 5 | 5 | 5 | 5 | 5 | 5 | 5 | 5 | 5 | 15 |
| 120 | 5 | 5 | 5 | 5 | 5 | 5 | 5 | 5 | 5 | 15 |

TABLE 2-continued

| Results on weeding effect in post-emergence stage | | | | | | | | | | |
|---|---|---|---|---|---|---|---|---|---|---|
| Compound No. | *Echinochloa crusgalli* | *Digitaria sanguinalis* | *Setaria viridis* | *Leptochloa chinensis* | *Eleusine indica* | *Veronica didyma Tenore* | *Galium aparine* | *Abutilon theophrasti* | *Amaranthus retroflexus* | Dose (g a.i./ha) |
| 121 | 5 | 5 | 5 | 5 | 5 | 5 | 5 | 5 | 5 | 15 |
| 123 | 5 | 5 | 5 | 5 | 5 | 5 | 5 | 5 | 5 | 15 |
| 124 | 5 | 5 | 5 | 5 | 5 | 5 | 5 | 5 | 5 | 15 |
| 140 | 5 | 5 | 5 | 5 | 5 | 5 | 5 | 5 | 5 | 15 |
| 146 | 5 | 5 | 5 | 5 | 5 | 5 | 5 | 5 | 5 | 15 |
| 160 | 5 | 5 | 5 | 5 | 5 | 5 | 5 | 5 | 5 | 15 |
| 170 | 5 | 5 | 5 | 5 | 5 | 5 | 5 | 5 | 5 | 15 |
| 197 | 5 | 5 | 5 | 5 | 5 | 5 | 5 | 5 | 5 | 15 |
| 218 | 5 | 5 | 5 | 5 | 5 | 5 | 5 | 5 | 5 | 15 |

Experiment on Weed Effect in Pre-Emergence Stage:

The seeds of monocotyledonous and dicotyledonous weeds and main crops (wheat, corn, rice, soybean, cotton, oilseed rape, millet and sorghum) were put into a plastic pot loaded with soil and covered with 0.5-2 cm soil. The test compounds of the present invention was dissolved with acetone, then added with tween 80, diluted by a certain amount of water to reach a certain concentration, and sprayed immediately after sowing. The obtained seeds were incubated for 4 weeks in the greenhouse after spraying and the test results were observed. It was observed that the herbicide mostly had excellent effect at the application rate of 250 g a.i./ha, especially to weeds such as *Echinochloa crusgalli, Digitaria sanguinalis* and *Abutilon theophrasti*, etc. And many compounds had good selectivity for corn, wheat, rice, and soybean.

It is indicated from the experiment of main weeds in wheat and rice fields that the compound of the present invention generally have good weed control efficacy. Above all, it is noted that the compound of the invention have extremely high activity to broad-leaved weeds and cyperaceae weeds, which are resistant to ALS inhibitor, like *Sagittaria trifolia, Scirpus juncoides, Cyperus difformis, Descurainia sophia, Capsella bursa-pastoris, Lithospermum arvense, Galium aparine* L., and *Cyperus rotundus* L., etc., and have excellent commercial value.

Transplanted Rice Safety Evaluation and Weed Control Effect Evaluation in Rice Field:

Rice field soil was loaded into a 1/1,000,000 ha pot. The seeds of *Echinochloa crusgalli, Scirpus juncoides*, and *Bidens tripartita* L. were sowed and gently covered with soil, then left to stand still in greenhouse in the state of 0.5-1 cm of water storage. The tuber of *Sagittaria trifolia* was planted in the next day or 2 days later. It was kept at 3-4 cm of water storage thereafter. The weeds were treated by dripping the WP or SC water diluents prepared according to the common preparation method of the compounds of the present invention with pipette homogeneously to achieve specified effective amount when *Echinochloa crusgalli, Scirpus juncoides*, and *Bidens tripartita* L. reached 0.5 leaf stage and *Sagittaria trifolia* reached the time point of primary leaf stage.

In addition, the rice field soil that loaded into the 1/1,000,000 ha pot was leveled to keep water storage at 3-4 cm depth. The 3 leaf stage rice (*japonica* rice) was transplanted at 3 cm of transplanting depth the next day. The compound of the present invention was treated by the same way after 5 days of transplantation.

The fertility condition of *Echinochloa crusgalli, Scirpus juncoides, Bidens tripartita* L. and *Sagittaria trifolia* 14 days after the treatment of the compound of the invention and the fertility condition of rice 21 days after the treatment of the compound of the invention respectively with the naked eye. Evaluate the weed control effect with the above activity standard level. Many compounds show excellent activity and selectivity.

Note: The seeds of *Echinochloa crusgalli, Scirpus juncoides* and *Bidens tripartita* L., and *Sagittaria trifolia* were collected from Heilongjiang Province of China. The tests indicated that the weeds were resistant to the common doses of Pyrazosulfuron-ethyl.

At the same time, it is found after several tests that the compounds and compositions of the present invention have good selectivity to many gramineae grasses such as *zoysia japonica*, bermuda grass, tall fescue, bluegrass, ryegrass and seashore paspalum etc, and are able to control many important grass weeds and broad-leaved weeds. The compounds also show excellent selectivity and commercial value in the tests on sugarcane, soybean, cotton, oil sunflower, potato, orchards and vegetables in different herbicide application methods.

The invention claimed is:

1. An isoxazoline oxime formate compound, as shown in general formula I:

I

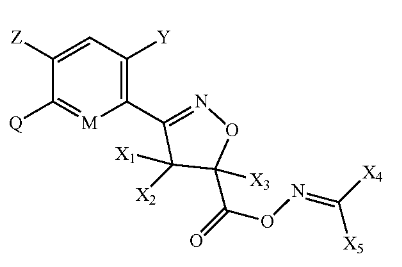

wherein,

Y represents halogen, halogenated alkyl, cyano, nitro or amino;

Z represents hydrogen, halogen or hydroxyl;

Q represents

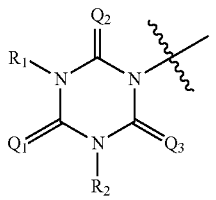

or

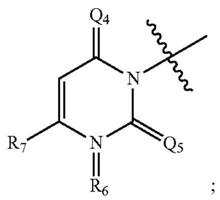

;

M represents CH or N;

$X_1$, $X_2$, $X_3$ each independently represent hydrogen, halogen, nitro, cyano, thiocyano, hydroxyl, sulfhydryl, carboxyl, sulfonic, formyl, halogenated formyl, azido, alkyl, alkenyl, alkynyl, cycloalkyl, cycloalkylalkyl, cycloalkenyl, cycloalkenylalkyl, —PO(OR')$_2$, —(CO)O-alkyl-O—N═C(R')$_2$, —OR", —(CO)R", —SR", —(SO)R", —(SO$_2$)R", —Si(R")$_3$, —O(CO)R", —O—(SO$_2$)R", —S(CO)R", —(SO$_2$)OR", —(CO)OR", —(CO)SR", —(CS)OR", —O(CO)OR", —(CO)(CO)OR", —(CO)O(CO)R", —(CO)O(CO)OR", heterocyclyl, heterocyclylalkyl, aryl, arylalkyl, amino, aminoalkyl, aminocarbonyl, aminocarbonylalkyl, aminocarbonyloxyalkyl, aminothiocarbonyloxyalkyl, aminosulfonyl, or aminosulfonyloxyalkyl, or $X_1$ and $X_2$ together form —$CH_2CH_2CH_2$—, —$CH_2CH_2CH_2CH_2$—, —$CH_2CH_2CH_2CH_2CH_2$—, —$OCH_2CH_2$—, —$OCH_2O$—, —$OCH_2CH_2O$—, —$CH_2CH_2OCO$— or —CH═CH—CH═CH—; wherein, the "alkyl", "alkenyl" or "alkynyl" is each independently unsubstituted or substituted with at least one substituent selected from halogen, cyano, hydroxyl, sulfhydryl, carboxyl, —OR", —(CO)R", —SR", —(SO$_2$)R", —O(CO)R", —O—(SO$_2$)R", —(CO)OR" or —O(CO)OR";

the "amino", "aminoalkyl", "aminocarbonyl", "aminocarbonylalkyl", "aminocarbonyloxyalkyl", "aminothiocarbonyloxyalkyl", "aminosulfonyl" or "aminosulfonyloxyalkyl" is each independently unsubstituted or substituted with one or two substituents selected from —$R_{11}$, —$OR_{11}$, —(CO)$R_{11}$, —(CO)$OR_1$, —O(CO)$R_{11}$, -alkyl-(CO)$OR_{11}$, —(SO$_2$)$R_{11}$, —(SO$_2$)$OR_{11}$, -alkyl-(SO$_2$)$R_{11}$, —(CO)N($R_{12}$)$_2$ or —(SO$_2$)N($R_{12}$)$_2$;

the "cycloalkyl", "cycloalkylalkyl", "cycloalkenyl", "cycloalkenylalkyl", "heterocyclyl", "heterocyclylalkyl", "aryl" or "arylalkyl" is each independently unsubstituted or substituted with at least one substituent selected from oxo, halogen, cyano, nitro, alkyl, halogenated alkyl, benzyl, —$OR_{14}$, —$SR_{14}$, —(CO)$OR_{14}$, —(SO$_2$)$R_{14}$, —N($R_{14}$)$_2$ or —O-alkyl-(CO)$OR_{14}$;

the "—$CH_2CH_2CH_2$—", "—$CH_2CH_2CH_2CH_2$—", "—$CH_2CH_2CH_2CH_2CH_2$—", "—$CH_2OCH_2$—", "—$CH_2CH_2OCH_2CH_2$—", "—$OCH_2CH_2$—", "—$OCH_2O$—", "—$OCH_2CH_2O$—", "—$CH_2CH_2CO$—", "—$CH_2OCO$—", "—$CH_2OSO_2$—", "—$CH_2CH_2OCO$—", "—CH═CHCOO—", "—CH═CH—CH═CH—" or "—$CH_2CH_2OCO$—" is each independently unsubstituted or substituted with halogen;

$X_4$, $X_5$ each independently represent hydrogen, halogen, cyano, nitro, -(alkyl)$_n$-$OR_{15}$, -(alkyl)$_n$-$SR_{15}$, -(alkyl)$_n$-(CO)$R_{15}$, -(alkyl)$_n$-O(CO)$R_{15}$, -(alkyl)$_n$-(CO)$OR_{15}$, -(alkyl)$_n$-(CO)$SR_{15}$, aminocarbonyl, alkyl, alkenyl, alkynyl, cycloalkyl, cycloalkylalkyl, cycloalkenyl, cycloalkenylalkyl, aryl, arylalkyl, heterocyclyl or heterocyclylalkyl, or the $CX_4X_5$ group together forms ring structure; wherein, the "aminocarbonyl" is unsubstituted or substituted with one or two substituents selected from —$R_{11}$, —$OR_{11}$, —(CO)$R_{11}$, —(CO)$OR_{11}$, —O(CO)$R_{11}$, -alkyl-(CO)$OR_{11}$, —(SO$_2$)$R_{11}$, —(SO$_2$)$OR_{11}$, -alkyl-(SO$_2$)$R_{11}$, —(CO)N($R_{12}$)$_2$ or —(SO$_2$)N($R_{12}$)$_2$; the "alkyl", "alkenyl" or "alkynyl" is each independently unsubstituted or substituted with halogen; the "cycloalkyl", "cycloalkylalkyl", "cycloalkenyl", "cycloalkenylalkyl", "aryl", "arylalkyl", "heterocyclyl" or "heterocyclylalkyl" is each independently unsubstituted or substituted with at least one substituent selected from oxo, halogen, cyano, nitro, alkyl, halogenated alkyl, benzyl, —$OR_{14}$, —$SR_{14}$, —(CO)$OR_{14}$, —(SO$_2$)$R_{14}$, —N($R_{14}$)$_2$ or —O-alkyl-(CO)$OR_{14}$, or two adjacent carbon atoms on the ring together with —$OCH_2CH_2$- or —$OCH_2O$— form a fused ring;

$Q_1$, $Q_2$, $Q_3$, $Q_4$, $Q_5$ each independently represent oxygen or sulphur;

$R_1$, $R_2$ each independently represent hydrogen, cyano, alkyl, alkenyl, alkynyl, formylalkyl, cyanoalkyl, amino, aminoalkyl, aminocarbonyl, aminocarbonylalkyl, aminosulfonyl, cycloalkyl, cycloalkylalkyl, cycloalkenyl, cycloalkenylalkyl, heterocyclyl, heterocyclylalkyl, aryl, arylalkyl, $R_4R_5N$—(CO)—$NR_3$—,

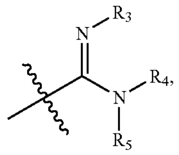

$R_3$—S(O)$_m$-(alkyl)$_n$-, $R_3$—O-(alkyl)$_n$-, $R_3$—(CO)-(alkyl)$_n$-, $R_3$—O-(alkyl)$_n$-(CO)-, $R_3$—(CO)—O-(alkyl)$_n$-, $R_3$—S—(CO)-(alkyl)$_n$-, $R_3$—O—(CO)-alkyl- or $R_3$—O—(CO)—O-alkyl-; wherein, the "alkyl", "alkenyl" or "alkynyl" is each independently unsubstituted or substituted with halogen;

the "amino", "aminoalkyl", "aminocarbonyl", "aminocarbonylalkyl" or "aminosulfonyl" is each independently unsubstituted or substituted with one or two substituents selected from —$R_{11}$, —$OR_{11}$, —(CO)$R_{11}$, —(CO)$OR_1$, —O(CO)$R_{11}$, -alkyl-(CO)$OR_{11}$, —(SO$_2$)$R_{11}$, —(SO$_2$)$OR_{11}$, -alkyl-(SO$_2$)$R_{11}$, —(CO)N($R_{12}$)$_2$ or —(SO$_2$)N($R_{12}$)$_2$;

the "cycloalkyl", "cycloalkylalkyl", "cycloalkenyl", "cycloalkenylalkyl", "heterocyclyl", "heterocyclylalkyl", "aryl" or "arylalkyl" is each independently unsubstituted or substituted with at least one substituent selected from oxo, halogen, cyano, nitro, alkyl, halogenated alkyl, benzyl, —$OR_{14}$, —$SR_{14}$, —(CO)$OR_{14}$, —(SO$_2$)$R_{14}$, —N($R_{14}$)$_2$ or —O-alkyl-(CO)$OR_{14}$;

$R_6$, $R_7$ each independently represent hydrogen, alkyl or halogenated alkyl;

R' each independently represents hydrogen, halogen, alkoxy, alkoxyalkyl, alkyl, alkenyl, alkynyl, cycloalkyl, cycloalkylalkyl, cycloalkenyl, cycloalkenylalkyl, aryl, arylalkyl, heterocyclyl or heterocyclylalkyl, or the C(R')$_2$ group in —(CO)O-alkyl-O—N═C(R')$_2$ together forms ring structure; wherein, the "alkyl", "alkenyl" or "alkynyl" is each independently unsubstituted or substituted with halogen; the "cycloalkyl", "cycloalkylalkyl", "cycloalkenyl", "cycloalkenylalkyl", "aryl", "arylalkyl", "heterocyclyl" or "heterocyclylalkyl" is each independently unsubstituted or substituted with at least one substituent selected from oxo, halogen, cyano, nitro, alkyl, halogenated alkyl, benzyl, —$OR_{14}$, —$SR_{14}$, —(CO)$OR_{14}$, —(SO$_2$)$R_{14}$, —N($R_{14}$)$_2$ or —O-alkyl-(CO)$OR_{14}$;

R" each independently represents alkyl, alkenyl, alkynyl, cycloalkyl, cycloalkylalkyl, cycloalkenyl, cycloalkenylalkyl, aryl, arylalkyl, arylalkenyl, heterocyclyl, heterocyclylalkyl or heterocyclylalkenyl; wherein, the "alkyl", "alkenyl" or "alkynyl" is each independently unsubstituted or substituted with at least one substituent selected from halogen, cyano, trialkylsilyl, —$OR_{13}$, —$SR_{13}$, —O(CO)$R_{13}$, —(CO)$R_{13}$, —(CO)$OR_{13}$ or —O(CO)$OR_{13}$; the "cycloalkyl", "cycloalkylalkyl", "cycloalkenyl", "cycloalkenylalkyl", "aryl", "arylalkyl", "arylalkenyl", "heterocyclyl", "heterocyclylalkyl" or "heterocyclylalkenyl" is each independently unsubstituted or substituted with at least one substituent selected from oxo, halogen, cyano, nitro, alkyl, halogenated alkyl, benzyl, —$OR_{14}$, —$SR_{14}$, —(CO)$OR_{14}$, —($SO_2$)$R_{14}$, —N$(R_{14})_2$ or —O-alkyl-(CO)$OR_{14}$;

$R_3$, $R_4$, $R_5$, $R_{15}$ each independently represent hydrogen, alkyl, alkenyl, alkynyl, cycloalkyl, cycloalkylalkyl, cycloalkenyl, cycloalkenylalkyl, heterocyclyl, heterocyclylalkyl, aryl or arylalkyl; wherein, the "alkyl", "alkenyl" or "alkynyl" is each independently unsubstituted or substituted with halogen; the "cycloalkyl", "cycloalkylalkyl", "cycloalkenyl", "cycloalkenylalkyl", "heterocyclyl", "heterocyclylalkyl", "aryl" or "arylalkyl" is each independently unsubstituted or substituted with at least one substituent selected from oxo, halogen, cyano, nitro, alkyl, halogenated alkyl, benzyl, —$OR_{14}$, —$SR_{14}$, —(CO)$OR_{14}$, —($SO_2$)$R_{14}$, —N$(R_{14})_2$ or —O-alkyl-(CO)$OR_{14}$;

$R_{11}$ each independently represents alkyl, alkenyl, alkynyl, cycloalkyl, cycloalkylalkyl, cycloalkenyl, cycloalkenylalkyl, phenyl or benzyl; wherein, the "alkyl", "alkenyl" or "alkynyl" is each independently unsubstituted or substituted with halogen; the "phenyl" or "benzyl" is each independently unsubstituted or substituted with at least one substituent selected from halogen, cyano, nitro, alkyl, halogenated alkyl, alkoxycarbonyl, alkylthio, alkylsulfonyl, alkoxy or halogenated alkoxy;

$R_{12}$ each independently represents hydrogen, alkyl, alkenyl, alkynyl, alkoxy, alkylsulfonyl, cycloalkyl, cycloalkylalkyl, cycloalkenyl or cycloalkenylalkyl; or the N$(R_{12})_2$ group in —(CO)N$(R_{12})_2$ or —($SO_2$)N$(R_{12})_2$ each independently represents heterocyclyl with nitrogen atom at 1-position;

$R_{13}$ each independently represents alkyl, alkenyl, alkynyl, cycloalkyl, phenyl or phenyl substituted with at least one substituent selected from halogen, cyano, nitro, alkyl, halogenated alkyl, alkoxy, halogenated alkoxy, alkoxycarbonyl, alkylthio, alkylsulfonyl or phenoxyl substituted with at least one substituent selected from halogen, cyano, nitro, alkyl, halogenated alkyl, alkoxy or halogenated alkoxy;

$R_{14}$ each independently represents hydrogen, alkyl, halogenated alkyl, phenyl or phenyl substituted with at least one substituent selected from halogen, cyano, nitro, alkyl, halogenated alkyl, alkoxycarbonyl, alkylthio, alkylsulfonyl, alkoxy or halogenated alkoxy;

m represents 0, 1 or 2; n independently represents 0 or 1.

2. The isoxazoline oxime formate compound according to claim 1, wherein, Y represents halogen, halogenated C1-C8 alkyl, cyano, nitro or amino;

$X_1$, $X_2$, $X_3$ each independently represent hydrogen, halogen, nitro, cyano, thiocyano, hydroxyl, sulfhydryl, carboxyl, sulfonic, formyl, halogenated formyl, azido, C1-C8 alkyl, C2-C8 alkenyl, C2-C8 alkynyl, C3-C8 cycloalkyl, C3-C8 cycloalkyl C1-C8 alkyl, C3-C8 cycloalkenyl, C3-C8 cycloalkenyl C1-C8 alkyl, —PO$(OR')_2$, —(CO)O—(C1-C8 alkyl)-O—N=C$(R')_2$, —OR", —(CO)R", —SR", —(SO)R", —($SO_2$)R", —Si$(R")_3$, —O(CO)R", —O—($SO_2$)R", —S(CO)R", —($SO_2$)OR", —(CO)OR", —(CO)SR", —(CS)OR", —O(CO)OR", —(CO)(CO)OR", —(CO)O(CO)R", —(CO)O(CO)OR", heterocyclyl, heterocyclyl C1-C8 alkyl, aryl, aryl C1-C8 alkyl, amino, amino C1-C8 alkyl, aminocarbonyl, aminocarbonyl C1-C8 alkyl, aminocarbonyloxy C1-C8 alkyl, aminothiocarbonyloxy C1-C8 alkyl, aminosulfonyl, or aminosulfonyloxy C1-C8 alkyl, or $X_1$ and $X_2$ together form —$CH_2CH_2CH_2$—, —$CH_2CH_2CH_2CH_2$—, —$CH_2CH_2CH_2CH_2CH_2$—, —$OCH_2CH_2$—, —$OCH_2O$—, —$OCH_2CH_2O$—, —$CH_2CH_2OCO$— or —CH═CH—CH═CH—; wherein, the "C1-C8 alkyl", "C2-C8 alkenyl" or "C2-C8 alkynyl" is each independently unsubstituted or substituted with one to four substituents selected from halogen, cyano, hydroxyl, sulfhydryl, carboxyl, —OR", —(CO)R", —SR", —($SO_2$)R", —O(CO)R", —O—($SO_2$)R", —(CO)OR" or —O(CO)OR";

the "amino", "amino C1-C8 alkyl", "aminocarbonyl", "aminocarbonyl C1-C8 alkyl", "aminocarbonyloxy C1-C8 alkyl", "aminothiocarbonyloxy C1-C8 alkyl", "aminosulfonyl" or "aminosulfonyloxy C1-C8 alkyl" is each independently unsubstituted or substituted with one or two substituents selected from —$R_{11}$, —$OR_{11}$, —(CO)$R_{11}$, —(CO)$OR_{11}$, —O(CO)$R_{11}$, —(C1-C8 alkyl)-(CO)$OR_{11}$, —($SO_2$)$R_{11}$, —($SO_2$)$OR_{11}$, —(C1-C8 alkyl)-($SO_2$)$R_{11}$, —(CO)N$(R_{12})_2$ or —($SO_2$)N$(R_{12})_2$;

the "C3-C8 cycloalkyl", "C3-C8 cycloalkyl C1-C8 alkyl", "C3-C8 cycloalkenyl", "C3-C8 cycloalkenyl C1-C8 alkyl", "heterocyclyl", "heterocyclyl C1-C8 alkyl", "aryl" or "aryl C1-C8 alkyl" is each independently unsubstituted or substituted with one to four substituents selected from oxo, halogen, cyano, nitro, C1-C8 alkyl, halogenated C1-C8 alkyl, benzyl, —$OR_{14}$, —$SR_{14}$, —(CO)$OR_{14}$, —($SO_2$)$R_{14}$, —N$(R_{14})_2$ or —O—(C1-C8 alkyl)-(CO)$OR_{14}$;

the "—$CH_2CH_2CH_2$—", "—$CH_2CH_2CH_2CH_2$—", "—$CH_2CH_2CH_2CH_2CH_2$—", "—$CH_2OCH_2$—", "—$CH_2CH_2OCH_2CH_2$—", "—$OCH_2CH_2$—", "—$OCH_2O$—", "—$OCH_2CH_2O$—", "—$CH_2CH_2CO$—", "—$CH_2OCO$—", "—$CH_2OSO_2$—", "—$CH_2CH_2OCO$—", "—CH═CHCOO—", "—CH═CH—CH═CH—" or "—$CH_2CH_2OCO$—" is each independently unsubstituted or substituted with halogen;

$X_4$, $X_5$ each independently represent hydrogen, halogen, cyano, nitro, —(C1-C8 alkyl)$_n$—$OR_{15}$, —(C1-C8 alkyl)$_n$-$SR_{15}$, —(C1-C8 alkyl)$_n$-(CO)$R_{15}$, —(C1-C8 alkyl)$_n$—O(CO)$R_{15}$, —(C1-C8 alkyl)$_n$-(CO)$OR_{15}$, —(C1-C8 alkyl)$_n$-(CO)$SR_{15}$, aminocarbonyl, C1-C8 alkyl, C2-C8 alkenyl, C2-C8 alkynyl, C3-C8 cycloalkyl, C3-C8 cycloalkyl C1-C8 alkyl, C3-C8 cycloalkenyl, C3-C8 cycloalkenyl C1-C8 alkyl, aryl, aryl C1-C8 alkyl, heterocyclyl or heterocyclyl C1-C8 alkyl, or the $CX_4X_5$ group together forms 5- to 8-membered carbocyclyl or oxygen-, sulfur- or nitrogen-containing heterocyclyl; wherein, the "aminocarbonyl" is unsubstituted or substituted with one or two substituents selected from —$R_{11}$, —$OR_{11}$, —(CO)$R_{11}$, —(CO)$OR_{11}$, —O(CO)$R_{11}$, —(C1-C8 alkyl)-(CO)$OR_{11}$, —($SO_2$)$R_{11}$, —($SO_2$)$OR_{11}$, —(C1-C8 alkyl)-($SO_2$)$R_{11}$, —(CO)N$(R_{12})_2$ or —($SO_2$)N$(R_{12})_2$; the "C1-C8 alkyl", "C2-C8 alkenyl" or "C2-C8 alkynyl" is each independently unsubstituted or substituted with halogen; the "C3-C8 cycloalkyl", "C3-C8 cycloalkyl C1-C8 alkyl", "C3-C8 cycloalkenyl", "C3-C8 cycloalkenyl C1-C8 alkyl", "aryl", "aryl C1-C8 alkyl", "heterocyclyl" or "heterocyclyl C1-C8 alkyl" is each independently unsubstituted or substituted with one to four substituents selected from oxo, halogen, cyano, nitro, C1-C8 alkyl, halogenated C1-C8 alkyl, benzyl, $—OR_{14}$, $—SR_{14}$, $—(CO)OR_{14}$, $—(SO_2)R_{14}$, $—N(R_{14})_2$ or $—O—$(C1-C8 alkyl)-$(CO)OR_{14}$, or two adjacent carbon atoms on the ring together with $—OCH_2CH_2$- or $—OCH_2O—$ form a fused ring; the "5- to 8-membered carbocyclyl or oxygen-, sulfur- or nitrogen-containing heterocyclyl" is unsubstituted or substituted with one to four substituents selected from C1-C8 alkyl, C1-C8 alkoxycarbonyl or benzyl, or forms a fused ring structure with aryl or heterocyclyl;

$R_1$, $R_2$ each independently represent hydrogen, cyano, C1-C8 alkyl, C2-C8 alkenyl, C2-C8 alkynyl, formyl C1-C8 alkyl, cyano C1-C8 alkyl, amino, amino C1-C8 alkyl, aminocarbonyl, aminocarbonyl C1-C8 alkyl, aminosulfonyl, C3-C8 cycloalkyl, C3-C8 cycloalkyl C1-C8 alkyl, C3-C8 cycloalkenyl, C3-C8 cycloalkenyl C1-C8 alkyl, heterocyclyl, heterocyclyl C1-C8 alkyl, aryl, aryl C1-C8 alkyl, $R_4R_5N—(CO)—NR_3—$,

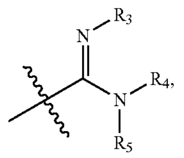

$R_3—S(O)_m—$(C1-C8 alkyl)$_n$-, $R_3—O—$(C1-C8 alkyl)$_n$-, $R_3—(CO)—$(C1-C8 alkyl)$_n$-, $R_3—O—$(C1-C8 alkyl)$_n$-(CO)—, $R_3—(CO)—O—$(C1-C8 alkyl)$_n$-, $R_3—S—(CO)—$(C1-C8 alkyl)$_n$-, $R_3—O—(CO)—$(C1-C8 alkyl)- or $R_3—O—(CO)—O—$(C1-C8 alkyl)-; wherein, the "C1-C8 alkyl", "C2-C8 alkenyl" or "C2-C8 alkynyl" is each independently unsubstituted or substituted with halogen;

the "amino", "amino C1-C8 alkyl", "aminocarbonyl", "aminocarbonyl C1-C8 alkyl" or "aminosulfonyl" is each independently unsubstituted or substituted with one or two substituents selected from $—R_{11}$, $—OR_{11}$, $—(CO)R_{11}$, $—(CO)OR_1$, $—O(CO)R_{11}$, —(C1-C8 alkyl)-$(CO)OR_1$, $—(SO_2)R_{11}$, $—(SO_2)OR_{11}$, —(C1-C8 alkyl)-$(SO_2)R_1$, $—(CO)N(R_{12})_2$ or $—(SO_2)N(R_{12})_2$;

the "C3-C8 cycloalkyl", "C3-C8 cycloalkyl C1-C8 alkyl", "C3-C8 cycloalkenyl", "C3-C8 cycloalkenyl C1-C8 alkyl", "heterocyclyl", "heterocyclyl C1-C8 alkyl", "aryl" or "aryl C1-C8 alkyl" is each independently unsubstituted or substituted with one to four substituents selected from oxo, halogen, cyano, nitro, C1-C8 alkyl, halogenated C1-C8 alkyl, benzyl, $—OR_{14}$, $—SR_{14}$, $—(CO)OR_{14}$, $—(SO_2)R_{14}$, $—N(R_{14})_2$ or $—O—$(C1-C8 alkyl)-$(CO)OR_{14}$;

$R_6$, $R_7$ each independently represent hydrogen, C1-C8 alkyl or halogenated C1-C8 alkyl;

R' each independently represents hydrogen, halogen, C1-C8 alkoxy, C1-C8 alkoxy C1-C8 alkyl, C1-C8 alkyl, C2-C8 alkenyl, C2-C8 alkynyl, C3-C8 cycloalkyl, C3-C8 cycloalkyl C1-C8 alkyl, C3-C8 cycloalkenyl, C3-C8 cycloalkenyl C1-C8 alkyl, aryl, aryl C1-C8 alkyl, heterocyclyl or heterocyclyl C1-C8 alkyl, or the $C(R')_2$ group in —(CO)O—(C1-C8 alkyl)—O—N=$C(R')_2$ together forms a 5- to 6-membered saturated carbocyclyl; wherein, the "C1-C8 alkyl", "C2-C8 alkenyl" or "C2-C8 alkynyl" is each independently unsubstituted or substituted with halogen; the "C3-C8 cycloalkyl", "C3-C8 cycloalkyl C1-C8 alkyl", "C3-C8 cycloalkenyl", "C3-C8 cycloalkenyl C1-C8 alkyl", "aryl", "aryl C1-C8 alkyl", "heterocyclyl" or "heterocyclyl C1-C8 alkyl" is each independently unsubstituted or substituted with one to four substituents selected from oxo, halogen, cyano, nitro, C1-C8 alkyl, halogenated C1-C8 alkyl, benzyl, $—OR_{14}$, $—SR_{14}$, $—(CO)OR_{14}$, $—(SO_2)R_{14}$, $—N(R_{14})_2$ or $—O—$(C1-C8 alkyl)-$(CO)OR_{14}$;

R" each independently represents C1-C8 alkyl, C2-C8 alkenyl, C2-C8 alkynyl, C3-C8 cycloalkyl, C3-C8 cycloalkyl C1-C8 alkyl, C3-C8 cycloalkenyl, C3-C8 cycloalkenyl C1-C8 alkyl, aryl, aryl C1-C8 alkyl, aryl C2-C8 alkenyl, heterocyclyl, heterocyclyl C1-C8 alkyl or heterocyclyl C2-C8 alkenyl; wherein, the "C1-C8 alkyl", "C2-C8 alkenyl" or "C2-C8 alkynyl" is each independently unsubstituted or substituted with one to three substituents selected from halogen, cyano, tri-C1-C8 alkylsilyl, $—OR_{13}$, $—SR_{13}$, $—O(CO)R_{13}$, $—(CO)R_{13}$, $—(CO)OR_{13}$ or $—O(CO)OR_{13}$; the "C3-C8 cycloalkyl", "C3-C8 cycloalkyl C1-C8 alkyl", "C3-C8 cycloalkenyl", "C3-C8 cycloalkenyl C1-C8 alkyl", "aryl", "aryl C1-C8 alkyl", "aryl C2-C8 alkenyl", "heterocyclyl", "heterocyclyl C1-C8 alkyl" or "heterocyclyl C2-C8 alkenyl" is each independently unsubstituted or substituted with one to four substituents selected from oxo, halogen, cyano, nitro, C1-C8 alkyl, halogenated C1-C8 alkyl, benzyl, $—OR_{14}$, $—SR_{14}$, $—(CO)OR_{14}$, $—(SO_2)R_{14}$, $—N(R_{14})_2$ or $—O—$(C1-C8 alkyl)-$(CO)OR_{14}$;

$R_3$, $R_4$, $R_5$, $R_{15}$ each independently represent hydrogen, C1-C8 alkyl, C2-C8 alkenyl, C2-C8 alkynyl, C3-C8 cycloalkyl, C3-C8 cycloalkyl C1-C8 alkyl, C3-C8 cycloalkenyl, C3-C8 cycloalkenyl C1-C8 alkyl, heterocyclyl, heterocyclyl C1-C8 alkyl, aryl or aryl C1-C8 alkyl; wherein, the "C1-C8 alkyl", "C2-C8 alkenyl" or "C2-C8 alkynyl" is each independently unsubstituted or substituted with halogen; the "C3-C8 cycloalkyl", "C3-C8 cycloalkyl C1-C8 alkyl", "C3-C8 cycloalkenyl", "C3-C8 cycloalkenyl C1-C8 alkyl", "heterocyclyl", "heterocyclyl C1-C8 alkyl", "aryl" or "aryl C1-C8 alkyl" is each independently unsubstituted or substituted with one to four substituents selected from oxo, halogen, cyano, nitro, C1-C8 alkyl, halogenated C1-C8 alkyl, benzyl, $—OR_{14}$, $—SR_{14}$, $—(CO)OR_{14}$, $—(SO_2)R_{14}$, $—N(R_{14})_2$ or $—O—$(C1-C8 alkyl)-$(CO)OR_{14}$;

$R_{11}$ each independently represents C1-C8 alkyl, C2-C8 alkenyl, C2-C8 alkynyl, C3-C8 cycloalkyl, C3-C8 cycloalkyl C1-C8 alkyl, C3-C8 cycloalkenyl, C3-C8 cycloalkenyl C1-C8 alkyl, phenyl or benzyl; wherein, the "C1-C8 alkyl", "C2-C8 alkenyl" or "C2-C8 alkynyl" is each independently unsubstituted or substituted with halogen; the "phenyl" or "benzyl" is each independently unsubstituted or substituted with one to four substituents selected from halogen, cyano, nitro, C1-C8 alkyl, halogenated C1-C8 alkyl, C1-C8 alkoxycarbonyl, C1-C8 alkylthio, C1-C8 alkylsulfonyl, C1-C8 alkoxy or halogenated C1-C8 alkoxy;

$R_{12}$ each independently represents hydrogen, C1-C8 alkyl, C2-C8 alkenyl, C2-C8 alkynyl, C1-C8 alkoxy, C1-C8 alkylsulfonyl, C3-C8 cycloalkyl, C3-C8 cycloalkyl C1-C8 alkyl, C3-C8 cycloalkenyl or C3-C8 cycloalkenyl C1-C8 alkyl; or the $N(R_{12})_2$ group in $—(CO)N(R_{12})_2$ or $—(SO_2)N(R_{12})_2$ each independently represents heterocyclyl

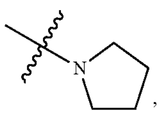, 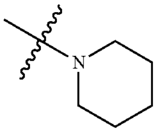 or 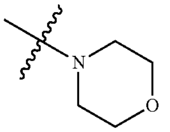

with nitrogen atom at 1-position;

$R_{13}$ each independently represents C1-C8 alkyl, C2-C8 alkenyl, C2-C8 alkynyl, C3-C8 cycloalkyl, phenyl or phenyl substituted with one to four substituents selected from halogen, cyano, nitro, C1-C8 alkyl, halogenated C1-C8 alkyl, C1-C8 alkoxy, halogenated C1-C8 alkoxy, C1-C8 alkoxycarbonyl, C1-C8 alkylthio, C1-C8 alkylsulfonyl or phenoxyl substituted with one to four substituents selected from halogen, cyano, nitro, C1-C8 alkyl, halogenated C1-C8 alkyl, C1-C8 alkoxy or halogenated C1-C8 alkoxy;

$R_{14}$ each independently represents hydrogen, C1-C8 alkyl, halogenated C1-C8 alkyl, phenyl or phenyl substituted with one to four substituents selected from halogen, cyano, nitro, C1-C8 alkyl, halogenated C1-C8 alkyl, C1-C8 alkoxycarbonyl, C1-C8 alkylthio, C1-C8 alkylsulfonyl, C1-C8 alkoxy or halogenated C1-C8 alkoxy.

3. The isoxazoline oxime formate compound according to claim 1, wherein, Y represents halogen, halogenated C1-C6 alkyl, cyano, nitro or amino;

$X_1$, $X_2$, $X_3$ each independently represent hydrogen, halogen, nitro, cyano, thiocyano, hydroxyl, sulfhydryl, carboxyl, sulfonic, formyl, halogenated formyl, azido, C1-C6 alkyl, C2-C6 alkenyl, C2-C6 alkynyl, C3-C6 cycloalkyl, C3-C6 cycloalkyl C1-C6 alkyl, C3-C6 cycloalkenyl, C3-C6 cycloalkenyl C1-C6 alkyl, $—PO(OR')_2$, $—(CO)O—(C1\text{-}C6\ alkyl)—O—N{=}C(R')_2$, —OR", —(CO)R", —SR", —(SO)R", $—(SO_2)R"$, $—Si(R")_3$, —O(CO)R", $—O—(SO_2)R"$, —S(CO)R", $—(SO_2)OR"$, —(CO)OR", —(CO)SR", —(CS)OR", —O(CO)OR", —(CO)(CO)OR", —(CO)O(CO)R", —(CO)O(CO)OR", heterocyclyl, heterocyclyl C1-C6 alkyl, aryl, aryl C1-C6 alkyl, amino, amino C1-C6 alkyl, aminocarbonyl, aminocarbonyl C1-C6 alkyl, aminocarbonyloxy C1-C6 alkyl, aminothiocarbonyloxy C1-C6 alkyl, aminosulfonyl, or aminosulfonyloxy C1-C6 alkyl, or $X_1$ and $X_2$ together form $—CH_2CH_2CH_2—$, $—CH_2CH_2CH_2CH_2—$, $—CH_2CH_2CH_2CH_2CH_2—$, $—OCH_2CH_2—$, $—OCH_2O—$, $—OCH_2CH_2O—$, $—CH_2CH_2OCO—$ or $—CH{=}CH—CH{=}CH—$; wherein, the “C1-C6 alkyl”, “C2-C6 alkenyl” or “C2-C6 alkynyl” is each independently unsubstituted or substituted with one, two or three substituents selected from halogen, cyano, hydroxyl, sulfhydryl, carboxyl, —OR", —(CO)R", —SR", $—(SO_2)R"$, —O(CO)R", $—O—(SO_2)R"$, —(CO)OR" or —O(CO)OR";

the “amino”, “amino C1-C6 alkyl”, “aminocarbonyl”, “aminocarbonyl C1-C6 alkyl”, “aminocarbonyloxy C1-C6 alkyl”, “aminothiocarbonyloxy C1-C6 alkyl”, “aminosulfonyl” or “aminosulfonyloxy C1-C6 alkyl” is each independently unsubstituted or substituted with one or two substituents selected from $—R_{11}$, $—OR_{11}$, $—(CO)R_{11}$, $—(CO)OR_{11}$, $—O(CO)R_{11}$, $—(C1\text{-}C6\ alkyl)\text{-}(CO)OR_{11}$, $—(SO_2)R_1$, $—(SO_2)OR_{11}$, $—(C1\text{-}C6\ alkyl)—(SO_2)R_1$, $—(CO)N(R_{12})_2$ or $—(SO_2)N(R_{12})_2$;

the “C3-C6 cycloalkyl”, “C3-C6 cycloalkyl C1-C6 alkyl”, “C3-C6 cycloalkenyl”, “C3-C6 cycloalkenyl C1-C6 alkyl”, “heterocyclyl”, “heterocyclyl C1-C6 alkyl”, “aryl” or “aryl C1-C6 alkyl” is each independently unsubstituted or substituted with one, two or three substituents selected from oxo, halogen, cyano, nitro, C1-C6 alkyl, halogenated C1-C6 alkyl, benzyl, $—OR_{14}$, $—SR_{14}$, $—(CO)OR_{14}$, $—(SO_2)R_{14}$, $—N(R_{14})_2$ or $—O—(C1\text{-}C6\ alkyl)\text{-}(CO)OR_{14}$;

the “$—CH_2CH_2CH_2—$”, “$—CH_2CH_2CH_2CH_2—$”, “$—CH_2CH_2CH_2CH_2CH_2—$”, “$—CH_2OCH_2—$”, “$—CH_2CH_2OCH_2CH_2—$”, “$—OCH_2CH_2—$”, “$—OCH_2O—$”, “$—OCH_2CH_2O—$”, “$—CH_2CH_2CO—$”, “$—CH_2OCO—$”, “$—CH_2OSO_2—$”, “$—CH_2CH_2OCO—$”, “$—CH{=}CHCOO—$”, “$—CH{=}CH—CH{=}CH—$” or “$—CH_2CH_2OCO—$” is each independently unsubstituted or substituted with halogen;

$X_4$, $X_5$ each independently represent hydrogen, halogen, cyano, nitro, $—(C1\text{-}C6\ alkyl)_n—OR_1S$, $—(C1\text{-}C6\ alkyl)_n\text{-}SR_{15}$, $—(C1\text{-}C6\ alkyl)_n\text{-}(CO)R_{15}$, $—(C1\text{-}C6\ alkyl)_n—O(CO)R_{15}$, $—(C1\text{-}C6\ alkyl)_n\text{-}(CO)OR_{15}$, $—(C1\text{-}C6\ alkyl)_n\text{-}(CO)SR_{15}$, aminocarbonyl, C1-C6 alkyl, C2-C6 alkenyl, C2-C6 alkynyl, C3-C6 cycloalkyl, C3-C6 cycloalkyl C1-C6 alkyl, C3-C6 cycloalkenyl, C3-C6 cycloalkenyl C1-C6 alkyl, aryl, aryl C1-C6 alkyl, heterocyclyl or heterocyclyl C1-C6 alkyl, or the $CX_4X_5$ group together forms 5- to 8-membered carbocyclyl or oxygen-, sulfur- or nitrogen-containing heterocyclyl; wherein, the “aminocarbonyl” is unsubstituted or substituted with one or two substituents selected from $—R_{11}$, $—OR_{11}$, $—(CO)R_{11}$, $—(CO)OR_{11}$, $—O(CO)R_{11}$, $—(C1\text{-}C6\ alkyl)\text{-}(CO)OR_{11}$, $—(SO_2)R_{11}$, $—(SO_2)OR_{11}$, $—(C1\text{-}C6\ alkyl)—(SO_2)R_{11}$, $—(CO)N(R_{12})_2$ or $—(SO_2)N(R_{12})_2$; the “C1-C6 alkyl”, “C2-C6 alkenyl” or “C2-C6 alkynyl” is each independently unsubstituted or substituted with halogen; the “C3-C6 cycloalkyl”, “C3-C6 cycloalkyl C1-C6 alkyl”, “C3-C6 cycloalkenyl”, “C3-C6 cycloalkenyl C1-C6 alkyl”, “aryl”, “aryl C1-C6 alkyl”, “heterocyclyl” or “heterocyclyl C1-C6 alkyl” is each independently unsubstituted or substituted with one, two or three substituents selected from oxo, halogen, cyano, nitro, C1-C6 alkyl, halogenated C1-C6 alkyl, benzyl, $—OR_{14}$, $—SR_{14}$, $—(CO)OR_{14}$, $—(SO_2)R_{14}$, $—N(R_{14})_2$ or $—O—(C1\text{-}C6\ alkyl)\text{-}(CO)OR_{14}$, or two adjacent carbon atoms on the ring together with $—OCH_2CH_2$- or $—OCH_2O—$ form a fused ring; the “5- to 8-membered carbocyclyl or oxygen-, sulfur- or nitrogen-containing heterocyclyl” is unsubstituted or substituted with one, two or three substituents selected from C1-C6 alkyl, C1-C6 alkoxycarbonyl or benzyl, or forms a fused ring structure with aryl or heterocyclyl;

$R_1$, $R_2$ each independently represent hydrogen, cyano, C1-C6 alkyl, C2-C6 alkenyl, C2-C6 alkynyl, formyl C1-C6 alkyl, cyano C1-C6 alkyl, amino, amino C1-C6 alkyl, aminocarbonyl, aminocarbonyl C1-C6 alkyl, aminosulfonyl, C3-C6 cycloalkyl, C3-C6 cycloalkyl C1-C6 alkyl, C3-C6 cycloalkenyl, C3-C6 cycloalkenyl C1-C6 alkyl, heterocyclyl, heterocyclyl C1-C6 alkyl, aryl, aryl C1-C6 alkyl, $R_4R_5N—(CO)—NR_3$-,

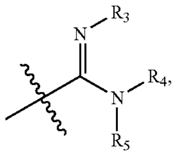

$R_3$—S(O)$_m$—(C1-C6 alkyl)$_n$-, $R_3$—O—(C1-C6 alkyl)$_n$-, $R_3$—(CO)—(C1-C6 alkyl)$_n$-, $R_3$—O—(C1-C6 alkyl)$_n$-(CO)—$R_3$—(CO)—O—(C1-C6 alkyl)$_n$-, $R_3$—S—(CO)—(C1-C6 alkyl)$_n$-, $R_3$—O—(CO)—(C1-C6 alkyl)- or $R_3$—O—(CO)—O—(C1-C6 alkyl)-;

wherein, the “C1-C6 alkyl”, “C2-C6 alkenyl” or “C2-C6 alkynyl” is each independently unsubstituted or substituted with halogen;

the “amino”, “amino C1-C6 alkyl”, “aminocarbonyl”, “aminocarbonyl C1-C6 alkyl” or “aminosulfonyl” is each independently unsubstituted or substituted with one or two substituents selected from —$R_{11}$, —$OR_{11}$, —(CO)$R_{11}$, —(CO)$OR_{11}$, —O(CO)$R_{11}$, —(C1-C6 alkyl)-(CO)$OR_{11}$, —($SO_2$)$R_{11}$, —($SO_2$)$OR_{11}$, —(C1-C6 alkyl)—($SO_2$)$R_1$, —(CO)N($R_{12}$)$_2$ or —($SO_2$)N($R_{12}$)$_2$;

the “C3-C6 cycloalkyl”, “C3-C6 cycloalkyl C1-C6 alkyl”, “C3-C6 cycloalkenyl”, “C3-C6 cycloalkenyl C1-C6 alkyl”, “heterocyclyl”, “heterocyclyl C1-C6 alkyl”, “aryl” or “aryl C1-C6 alkyl” is each independently unsubstituted or substituted with one, two or three substituents selected from oxo, halogen, cyano, nitro, C1-C6 alkyl, halogenated C1-C6 alkyl, benzyl, —$OR_{14}$, —$SR_{14}$, —(CO)$OR_{14}$, —($SO_2$)$R_{14}$, —N($R_{14}$)$_2$ or —O—(C1-C6 alkyl)-(CO)$OR_{14}$;

$R_6$, $R_7$ each independently represent hydrogen, C1-C6 alkyl or halogenated C1-C6 alkyl;

R' each independently represents hydrogen, halogen, C1-C6 alkoxy, C1-C6 alkoxy C1-C6 alkyl, C1-C6 alkyl, C2-C6 alkenyl, C2-C6 alkynyl, C3-C6 cycloalkyl, C3-C6 cycloalkyl C1-C6 alkyl, C3-C6 cycloalkenyl, C3-C6 cycloalkenyl C1-C6 alkyl, aryl, aryl C1-C6 alkyl, heterocyclyl or heterocyclyl C1-C6 alkyl, or the C(R')$_2$ group in —(CO)O—(C1-C6 alkyl)—O—N=C(R')$_2$ together forms a 5- to 6-membered saturated carbocyclyl; wherein, the “C1-C6 alkyl”, “C2-C6 alkenyl” or “C2-C6 alkynyl” is each independently unsubstituted or substituted with halogen; the “C3-C6 cycloalkyl”, “C3-C6 cycloalkyl C1-C6 alkyl”, “C3-C6 cycloalkenyl”, “C3-C6 cycloalkenyl C1-C6 alkyl”, “aryl”, “aryl C1-C6 alkyl”, “heterocyclyl” or “heterocyclyl C1-C6 alkyl” is each independently unsubstituted or substituted with one, two or three substituents selected from oxo, halogen, cyano, nitro, C1-C6 alkyl, halogenated C1-C6 alkyl, benzyl, —$OR_{14}$, —$SR_{14}$, —(CO)$OR_{14}$, —($SO_2$)$R_{14}$, —N($R_{14}$)$_2$ or —O—(C1-C6 alkyl)-(CO)$OR_{14}$;

R" each independently represents C1-C6 alkyl, C2-C6 alkenyl, C2-C6 alkynyl, C3-C6 cycloalkyl, C3-C6 cycloalkyl C1-C6 alkyl, C3-C6 cycloalkenyl, C3-C6 cycloalkenyl C1-C6 alkyl, aryl, aryl C1-C6 alkyl, aryl C2-C6 alkenyl, heterocyclyl, heterocyclyl C1-C6 alkyl or heterocyclyl C2-C6 alkenyl; wherein, the “C1-C6 alkyl”, “C2-C6 alkenyl” or “C2-C6 alkynyl” is each independently unsubstituted or substituted with one, two or three substituents selected from halogen, cyano, tri-C1-C8 alkylsilyl, —$OR_{13}$, —$SR_{13}$, —O(CO)$R_{13}$, —(CO)$R_{13}$, —(CO)$OR_{13}$ or —O(CO)$OR_{13}$; the “C3-C6 cycloalkyl”, “C3-C6 cycloalkyl C1-C6 alkyl”, “C3-C6 cycloalkenyl”, “C3-C6 cycloalkenyl C1-C6 alkyl”, “aryl”, “aryl C1-C6 alkyl”, “aryl C2-C6 alkenyl”, “heterocyclyl”, “heterocyclyl C1-C6 alkyl” or “heterocyclyl C2-C6 alkenyl” is each independently unsubstituted or substituted with one, two or three substituents selected from oxo, halogen, cyano, nitro, C1-C6 alkyl, halogenated C1-C6 alkyl, benzyl, —$OR_{14}$, —$SR_{14}$, —(CO)$OR_{14}$, —($SO_2$)$R_{14}$, —N($R_{14}$)$_2$ or —O—(C1-C6 alkyl)-(CO)$OR_{14}$;

$R_3$, $R_4$, $R_5$, $R_{15}$ each independently represent hydrogen, C1-C6 alkyl, C2-C6 alkenyl, C2-C6 alkynyl, C3-C6 cycloalkyl, C3-C6 cycloalkyl C1-C6 alkyl, C3-C6 cycloalkenyl, C3-C6 cycloalkenyl C1-C6 alkyl, heterocyclyl, heterocyclyl C1-C6 alkyl, aryl or aryl C1-C6 alkyl; wherein, the “C1-C6 alkyl”, “C2-C6 alkenyl” or “C2-C6 alkynyl” is each independently unsubstituted or substituted with halogen; the “C3-C6 cycloalkyl”, “C3-C6 cycloalkyl C1-C6 alkyl”, “C3-C6 cycloalkenyl”, “C3-C6 cycloalkenyl C1-C6 alkyl”, “heterocyclyl”, “heterocyclyl C1-C6 alkyl”, “aryl” or “aryl C1-C6 alkyl” is each independently unsubstituted or substituted with one, two or three substituents selected from oxo, halogen, cyano, nitro, C1-C6 alkyl, halogenated C1-C6 alkyl, benzyl, —$OR_{14}$, —$SR_{14}$, —(CO)$OR_{14}$, —($SO_2$)$R_{14}$, —N($R_{14}$)$_2$ or —O—(C1-C6 alkyl)-(CO)$OR_{14}$;

$R_{11}$ each independently represents C1-C6 alkyl, C2-C6 alkenyl, C2-C6 alkynyl, C3-C6 cycloalkyl, C3-C6 cycloalkyl C1-C6 alkyl, C3-C6 cycloalkenyl, C3-C6 cycloalkenyl C1-C6 alkyl, phenyl or benzyl; wherein, the “C1-C6 alkyl”, “C2-C6 alkenyl” or “C2-C6 alkynyl” is each independently unsubstituted or substituted with halogen; the “phenyl” or “benzyl” is each independently unsubstituted or substituted with one, two or three substituents selected from halogen, cyano, nitro, C1-C6 alkyl, halogenated C1-C6 alkyl, C1-C6 alkoxycarbonyl, C1-C6 alkylthio, C1-C6 alkylsulfonyl, C1-C6 alkoxy or halogenated C1-C6 alkoxy;

$R_{12}$ each independently represents hydrogen, C1-C6 alkyl, C2-C6 alkenyl, C2-C6 alkynyl, C1-C6 alkoxy, C1-C6 alkylsulfonyl, C3-C6 cycloalkyl, C3-C6 cycloalkyl C1-C6 alkyl, C3-C6 cycloalkenyl or C3-C6 cycloalkenyl C1-C6 alkyl; or the N($R_{12}$)$_2$ group in —(CO)N($R_{12}$)$_2$ or —($SO_2$)N($R_{12}$)$_2$ each independently represents heterocyclyl, or

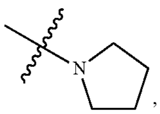
,
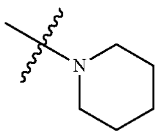
or
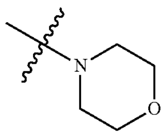

with nitrogen atom at 1-position;

$R_{13}$ each independently represents C1-C6 alkyl, C2-C6 alkenyl, C2-C6 alkynyl, C3-C6 cycloalkyl, phenyl or phenyl substituted with one, two or three substituents selected from halogen, cyano, nitro, C1-C6 alkyl, halogenated C1-C6 alkyl, C1-C6 alkoxy, halogenated C1-C6 alkoxy, C1-C6 alkoxycarbonyl, C1-C6 alkylthio, C1-C6 alkylsulfonyl or phenoxyl substituted with one, two or three substituents selected from halogen, cyano, nitro, C1-C6 alkyl, halogenated C1-C6 alkyl, C1-C6 alkoxy or halogenated C1-C6 alkoxy;

$R_{14}$ each independently represents hydrogen, C1-C6 alkyl, halogenated C1-C6 alkyl, phenyl or phenyl substituted with one, two or three substituents selected from halogen, cyano, nitro, C1-C6 alkyl, halogenated C1-C6 alkyl, C1-C6 alkoxycarbonyl, C1-C6 alkylthio, C1-C6 alkylsulfonyl, C1-C6 alkoxy or halogenated C1-C6 alkoxy.

4. The isoxazoline oxime formate compound according to claim 1, wherein, $X_4$, $X_5$ each independently represent hydrogen, halogen, cyano, nitro, —(C1-C3 alkyl)$_n$—$OR_{15}$, —(C1-C3 alkyl)$_n$-$SR_{15}$, —(C1-C3 alkyl)$_n$-(CO)$R_{15}$, —(C1-C3 alkyl)$_n$—O(CO)$R_{15}$, —(C1-C3 alkyl)$_n$-(CO)$OR_{15}$, —(C1-C3 alkyl)$_n$-(CO)$SR_{15}$, aminocarbonyl, C1-C6 alkyl, C2-C6 alkenyl, C2-C6 alkynyl, C3-C6 cycloalkyl, C3-C6 cycloalkyl C1-C3 alkyl, C3-C6 cycloalkenyl, C3-C6 cycloalkenyl C1-C3 alkyl, aryl, aryl C1-C3 alkyl, heterocyclyl or heterocyclyl C1-C3 alkyl, or the $CX_4X_5$ group together forms a 5- to 8-membered saturated carbocyclyl,

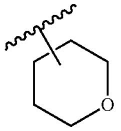 or 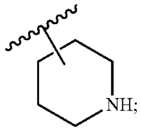

wherein, the "aminocarbonyl" is unsubstituted or substituted with one or two substituents selected from —$R_{11}$, —$OR_{11}$, —(CO)$R_{11}$, —(CO)$OR_{11}$, —O(CO) $R_{11}$, —(C1-C3 alkyl)-(CO)$OR_{11}$, —($SO_2$)$R_1$, —($SO_2$) $OR_{11}$, —(C1-C3 alkyl)—($SO_2$)$R_{11}$, —(CO)N($R_{12}$)$_2$ or —($SO_2$)N($R_{12}$)$_2$; the "C1-C6 alkyl", "C2-C6 alkenyl" or "C2-C6 alkynyl" is each independently unsubstituted or substituted with halogen; the "C3-C6 cycloalkyl", "C3-C6 cycloalkyl C1-C3 alkyl", "C3-C6 cycloalkenyl", "C3-C6 cycloalkenyl C1-C3 alkyl", "aryl", "aryl C1-C3 alkyl", "heterocyclyl" or "heterocyclyl C1-C3 alkyl" is each independently unsubstituted or substituted with one, two or three substituents selected from oxo, halogen, cyano, nitro, C1-C6 alkyl, halogenated C1-C6 alkyl, benzyl, —$OR_{14}$, —$SR_{14}$, —(CO)$OR_{14}$, —($SO_2$)$R_{14}$, —N($R_{14}$)$_2$ or —O—(C1-C3 alkyl)-(CO)$OR_{14}$, or two adjacent carbon atoms on the ring together with —$OCH_2CH_2$- or —$OCH_2O$— form a fused ring; the "5- to 8-membered saturated carbocyclyl,

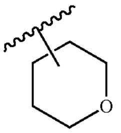 or 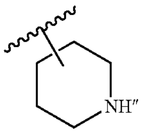

is unsubstituted or substituted with one, two or three substituents selected from C1-C6 alkyl, C1-C6 alkoxycarbonyl or benzyl, or forms a fused ring structure with aryl or thienyl;

$R_{15}$ each independently represents hydrogen, C1-C6 alkyl, C2-C6 alkenyl, C2-C6 alkynyl, C3-C6 cycloalkyl, C3-C6 cycloalkyl C1-C3 alkyl, C3-C6 cycloalkenyl, C3-C6 cycloalkenyl C1-C3 alkyl, heterocyclyl, heterocyclyl C1-C3 alkyl, aryl or aryl C1-C3 alkyl; wherein, the "C1-C6 alkyl", "C2-C6 alkenyl" or "C2-C6 alkynyl" is each independently unsubstituted or substituted with halogen; the "C3-C6 cycloalkyl", "C3-C6 cycloalkyl C1-C3 alkyl", "C3-C6 cycloalkenyl", "C3-C6 cycloalkenyl C1-C3 alkyl", "heterocyclyl", "heterocyclyl C1-C3 alkyl", "aryl" or "aryl C1-C3 alkyl" is each independently unsubstituted or substituted with one, two or three substituents selected from oxo, halogen, cyano, nitro, C1-C6 alkyl, halogenated C1-C6 alkyl, benzyl, —$OR_{14}$, —$SR_{14}$, —(CO)$OR_{14}$, —($SO_2$)$R_{14}$, —N($R_{14}$)$_2$ or —O—(C1-C3 alkyl)-(CO) $OR_{14}$;

$R_{11}$ each independently represents C1-C6 alkyl, C2-C6 alkenyl, C2-C6 alkynyl, C3-C6 cycloalkyl, C3-C6 cycloalkyl C1-C3 alkyl, C3-C6 cycloalkenyl, C3-C6 cycloalkenyl C1-C3 alkyl, phenyl or benzyl; wherein, the "C1-C6 alkyl", "C2-C6 alkenyl" or "C2-C6 alkynyl" is each independently unsubstituted or substituted with halogen; the "phenyl" or "benzyl" is each independently unsubstituted or substituted with one, two or three substituents selected from halogen, cyano, nitro, C1-C6 alkyl, halogenated C1-C6 alkyl, C1-C6 alkoxycarbonyl, C1-C6 alkylthio, C1-C6 alkylsulfonyl, C1-C6 alkoxy or halogenated C1-C6 alkoxy;

$R_{12}$ each independently represents hydrogen, C1-C6 alkyl, C2-C6 alkenyl, C2-C6 alkynyl, C1-C6 alkoxy, C1-C6 alkylsulfonyl, C3-C6 cycloalkyl, C3-C6 cycloalkyl C1-C3 alkyl, C3-C6 cycloalkenyl or C3-C6 cycloalkenyl C1-C3 alkyl; or the N($R_{12}$)$_2$ group in —(CO)N($R_{12}$)$_2$ or —($SO_2$)N($R_{12}$)$_2$ each independently represents heterocyclyl,

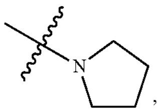, 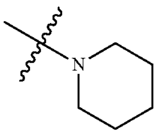 or 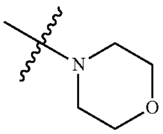

with nitrogen atom at 1-position;

$R_{14}$ each independently represents hydrogen, C1-C6 alkyl, halogenated C1-C6 alkyl, phenyl or phenyl substituted with one, two or three substituents selected from halogen, cyano, nitro, C1-C6 alkyl, halogenated C1-C6 alkyl, C1-C6 alkoxycarbonyl, C1-C6 alkylthio, C1-C6 alkylsulfonyl, C1-C6 alkoxy or halogenated C1-C6 alkoxy.

5. The isoxazoline oxime formate compound according to claim 1, wherein, Y represents chlorine;

Z represents fluorine;

$X_1$, $X_2$, $X_3$ each independently represent hydrogen or C1-C6 alkyl;

$X_4$, $X_5$ each independently represent hydrogen, —(C1-C3 alkyl)$_n$—$OR_{15}$, —(CO)$OR_{15}$, C1-C6 alkyl, C3-C6 cycloalkyl, phenyl or heterocyclyl, or the $CX_4X_5$ group together forms a 5- to 6-membered saturated carbocyclyl; wherein, the "C3-C6 cycloalkyl", "phenyl" or "heterocyclyl" is each independently unsubstituted or substituted with one, two or three substituents selected from C1-C6 alkyl; the "heterocyclyl" is selected from

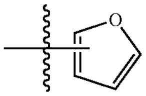 or 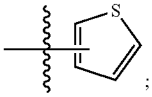;

$Q_1$, $Q_2$, $Q_3$ each independently represent oxygen or sulphur;

$R_1$, $R_2$ each independently represent C1-C6 alkyl;

$R_6$ represents C1-C6 alkyl;

$R_7$ represents halogenated C1-C6 alkyl;

$R_{15}$ each independently represents C1-C6 alkyl.

6. The isoxazoline oxime formate compound according to claim 1, wherein the isoxazoline oxime formate compound is selected from any one in Table 1.

7. The isoxazoline oxime formate compound according to claim 5, wherein Q represents

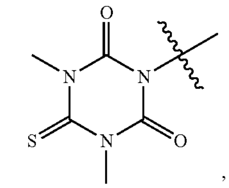
,
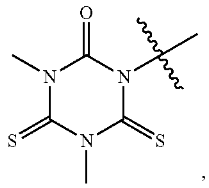
,
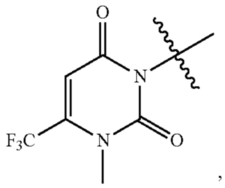
,
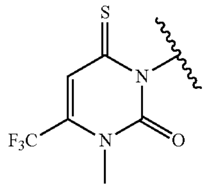
or
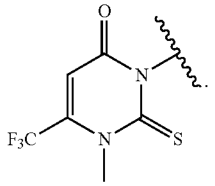

8. The isoxazoline oxime formate compound according to claim 1, wherein Q represents

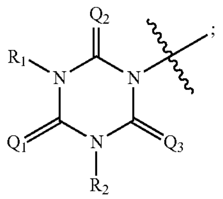

$Q_1$, $Q_2$, $Q_3$ each independently represent oxygen or sulphur;

$R_1$, $R_2$ each independently represent hydrogen, cyano, alkyl, alkenyl, alkynyl, formylalkyl, cyanoalkyl, amino, aminoalkyl, aminocarbonyl, aminocarbonylalkyl, aminosulfonyl, cycloalkyl, cycloalkylalkyl, cycloalkenyl, cycloalkenylalkyl, heterocyclyl, heterocyclylalkyl, aryl, arylalkyl, $R_4R_5N$—(CO)—$NR_3$—,

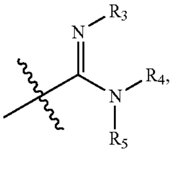

$R_3$—S(O)$_m$-(alkyl)$_n$-, $R_3$—O-(alkyl)$_n$-, $R_3$—(CO)-(alkyl)$_n$-, $R_3$—O-(alkyl)$_n$-(CO)—, $R_3$—(CO)—O-(alkyl)$_n$-, $R_3$—S—(CO)-(alkyl)$_n$-, $R_3$—O—(CO)-alkyl- or $R_3$—O—(CO)—O-alkyl-; wherein, the "alkyl", "alkenyl" or "alkynyl" is each independently unsubstituted or substituted with halogen;

the "amino", "aminoalkyl", "aminocarbonyl", "aminocarbonylalkyl" or "aminosulfonyl" is each independently unsubstituted or substituted with one or two substituents selected from —$R_{11}$, —$OR_{11}$, —(CO)$R_{11}$, —(CO)$OR_1$, —O(CO)$R_{11}$, -alkyl-(CO)$OR_{11}$, —($SO_2$)$R_{11}$, —($SO_2$)$OR_{11}$, -alkyl-($SO_2$)$R_{11}$, —(CO)N($R_{12}$)$_2$ or —($SO_2$)N($R_{12}$)$_2$;

the "cycloalkyl", "cycloalkylalkyl", "cycloalkenyl", "cycloalkenylalkyl", "heterocyclyl", "heterocyclylalkyl", "aryl" or "arylalkyl" is each independently unsubstituted or substituted with at least one substituent selected from oxo, halogen, cyano, nitro, alkyl, halogenated alkyl, benzyl, —$OR_{14}$, —$SR_{14}$, —(CO)$OR_{14}$, —($SO_2$)$R_{14}$, —N($R_{14}$)$_2$ or —O-alkyl-(CO)$OR_{14}$;

$R_3$, $R_4$, $R_5$ each independently represent hydrogen, alkyl, alkenyl, alkynyl, cycloalkyl, cycloalkylalkyl, cycloalkenyl, cycloalkenylalkyl, heterocyclyl, heterocyclylalkyl, aryl or arylalkyl; wherein, the "alkyl", "alkenyl" or "alkynyl" is each independently unsubstituted or substituted with halogen; the "cycloalkyl", "cycloalkylalkyl", "cycloalkenyl", "cycloalkenylalkyl", "heterocyclyl", "heterocyclylalkyl", "aryl" or "arylalkyl" is each independently unsubstituted or substituted with at least one substituent selected from oxo, halogen, cyano, nitro, alkyl, halogenated alkyl, benzyl, —$OR_{14}$, —$SR_{14}$, —(CO)$OR_{14}$, —($SO_2$)$R_{14}$, —N($R_{14}$)$_2$ or —O-alkyl-(CO)$OR_{14}$;

$R_{11}$ each independently represents alkyl, alkenyl, alkynyl, cycloalkyl, cycloalkylalkyl, cycloalkenyl, cycloalkenylalkyl, phenyl or benzyl; wherein, the "alkyl", "alkenyl" or "alkynyl" is each independently unsubstituted or substituted with halogen; the "phenyl" or "benzyl" is each independently unsubstituted or substituted with at least one substituent selected from halogen, cyano, nitro, alkyl, halogenated alkyl, alkoxycarbonyl, alkylthio, alkylsulfonyl, alkoxy or halogenated alkoxy;

$R_{12}$ each independently represents hydrogen, alkyl, alkenyl, alkynyl, alkoxy, alkylsulfonyl, cycloalkyl, cycloalkylalkyl, cycloalkenyl or cycloalkenylalkyl; or the N($R_{12}$)$_2$ group in —(CO)N($R_{12}$)$_2$ or —($SO_2$)N($R_{12}$)$_2$ each independently represents heterocyclyl with nitrogen atom at 1-position;

$R_{14}$ each independently represents hydrogen, alkyl, halogenated alkyl, phenyl or phenyl substituted with at least one substituent selected from halogen, cyano, nitro, alkyl, halogenated alkyl, alkoxycarbonyl, alkylthio, alkylsulfonyl, alkoxy or halogenated alkoxy;

m represents 0, 1 or 2; n independently represents 0 or 1.

9. An herbicidal composition, comprising at least one of the isoxazoline oxime formate compound according to claim 1 in a herbicidally effective amount.

10. The herbicidal composition according to claim 9, which further comprises a formulation auxiliary.

11. A method for preparing the isoxazoline oxime formate compound according to claim 1, comprising the following steps:

subjecting a compound as shown in general formula II and a compound as shown in general formula III to condensation reaction to obtain a compound as shown in general formula I, with the chemical reaction equation shown as follows:

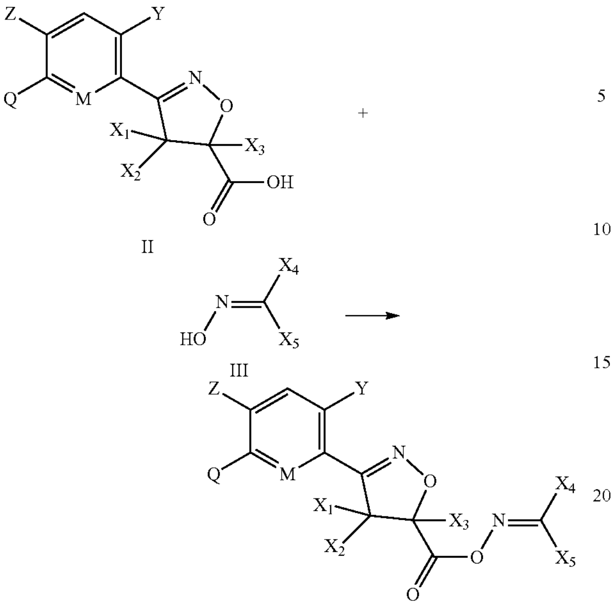

II

III

I wherein, the substituents Q, Y, Z, $X_1$, $X_2$, $X_3$, $X_4$ and $X_5$ are defined according to claim 1.

12. The method for preparing the isoxazoline oxime formate compound according to claim 11, wherein the reaction is carried out under the action of base and condensing agent in the presence of aprotic solvent the condensing agent is PyBop, HATU or HOBt-EDCI; the solvent is one or more mixed solvents selected from dichloromethane, dichloroethane, acetonitrile, N,N-dimethylformamide, N,N-dimethylacetamide, dimethylsulfoxide, tetrahydrofuran, toluene and xylene.

13. The method for preparing the isoxazoline oxime formate compound according to claim 12, wherein the base is one or more selected from triethylamine, trimethylamine, DIPEA and DBU.

14. A method for controlling a weed, comprising applying at least one of the isoxazoline oxime formate compound according to claim 1 in a herbicidally effective amount on a plant or a weed area.

15. A method for controlling a weed, comprising applying the herbicidal composition according to claim 9 in a herbicidally effective amount on a plant or a weed area.

* * * * *